United States Patent
Mirkin et al.

(10) Patent No.: US 11,690,920 B2
(45) Date of Patent: Jul. 4, 2023

(54) GENERAL AND DIRECT METHOD FOR PREPARING OLIGONUCLEOTIDE-FUNCTIONALIZED METAL-ORGANIC FRAMEWORK NANOPARTICLES

(71) Applicant: NORTHWESTERN UNIVERSITY, Evanston, IL (US)

(72) Inventors: Chad A. Mirkin, Wilmette, IL (US); Shunzhi Wang, Evanston, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 534 days.

(21) Appl. No.: 16/629,686

(22) PCT Filed: Jul. 13, 2018

(86) PCT No.: PCT/US2018/042050
§ 371 (c)(1),
(2) Date: Jan. 9, 2020

(87) PCT Pub. No.: WO2019/032241
PCT Pub. Date: Feb. 14, 2019

(65) Prior Publication Data
US 2021/0236651 A1      Aug. 5, 2021

Related U.S. Application Data

(60) Provisional application No. 62/532,241, filed on Jul. 13, 2017.

(51) Int. Cl.
*A61K 47/69*      (2017.01)
*A61K 47/54*      (2017.01)
(Continued)

(52) U.S. Cl.
CPC .......... *A61K 47/6929* (2017.08); *A61K 38/28* (2013.01); *A61K 47/549* (2017.08);
(Continued)

(58) Field of Classification Search
CPC .. A61K 47/6929; A61K 38/28; A61K 47/549; A61K 47/6923; C07F 5/06;
(Continued)

(56) References Cited

U.S. PATENT DOCUMENTS 3,687,808 A    8/1972  Merigan et al.
4,469,863 A    9/1984  Ts et al.
(Continued)

FOREIGN PATENT DOCUMENTS

CN    103212089 A    7/2013
EP    1072679 A2     1/2001
(Continued)

OTHER PUBLICATIONS

Dumont, M. F., et al in Bioconjugate Chem, vol. 23, # 5, pp. 951-957, 2012.*
(Continued)

*Primary Examiner* — Gollamudi S Kishore
(74) *Attorney, Agent, or Firm* — Marshall, Gerstein & Borun LLP

(57) ABSTRACT

The present disclosure generally relates to metal-organic framework nanoparticles containing terminal phosphate-modified oligonucleotides, methods for making the same, and methods of using the same.

34 Claims, 29 Drawing Sheets

Specification includes a Sequence Listing.

αInset: Zr₆O₄(OH)₄ secondary building units (SBU).

(51) Int. Cl.
*A61K 38/28* (2006.01)
*C12N 15/113* (2010.01)
*C07F 5/06* (2006.01)
*C07F 7/00* (2006.01)
*C07F 11/00* (2006.01)
*C07F 15/02* (2006.01)

(52) U.S. Cl.
CPC .............. *C07F 5/06* (2013.01); *C07F 7/003* (2013.01); *C07F 11/00* (2013.01); *C07F 15/02* (2013.01); *C12N 15/113* (2013.01); *C12N 2310/351* (2013.01); *C12N 2320/32* (2013.01)

(58) Field of Classification Search
CPC .......... C07F 7/003; C07F 11/00; C07F 15/02; C12N 15/113; C12N 2310/351; C12N 2320/32; C12N 15/111
See application file for complete search history.

(56) References Cited

U.S. PATENT DOCUMENTS

| | | |
|---|---|---|
| 4,476,301 A | 10/1984 | Imbach et al. |
| 4,845,205 A | 7/1989 | Huynh et al. |
| 4,981,957 A | 1/1991 | Lebleu et al. |
| 5,008,050 A | 4/1991 | Cullis et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,134,066 A | 7/1992 | Rogers et al. |
| 5,166,315 A | 11/1992 | Summerton et al. |
| 5,175,273 A | 12/1992 | Bischofberger et al. |
| 5,177,196 A | 1/1993 | Meyer et al. |
| 5,185,444 A | 2/1993 | Summerton et al. |
| 5,188,897 A | 2/1993 | Suhadolnik et al. |
| 5,194,599 A | 3/1993 | Froehler et al. |
| 5,214,134 A | 5/1993 | Weis et al. |
| 5,216,141 A | 6/1993 | Benner |
| 5,235,033 A | 8/1993 | Summerton et al. |
| 5,264,423 A | 11/1993 | Cohen et al. |
| 5,264,562 A | 11/1993 | Matteucci |
| 5,264,564 A | 11/1993 | Matteucci |
| 5,264,618 A | 11/1993 | Felgner et al. |
| 5,270,163 A | 12/1993 | Gold et al. |
| 5,276,019 A | 1/1994 | Cohen et al. |
| 5,278,302 A | 1/1994 | Caruthers et al. |
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |
| 5,367,066 A | 11/1994 | Urdea et al. |
| 5,393,878 A | 2/1995 | Leumann |
| 5,399,676 A | 3/1995 | Froehler |
| 5,405,938 A | 4/1995 | Summerton et al. |
| 5,405,939 A | 4/1995 | Suhadolnik et al. |
| 5,432,272 A | 7/1995 | Benner |
| 5,434,257 A | 7/1995 | Matteucci et al. |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,502,177 A | 3/1996 | Matteucci et al. |
| 5,514,785 A | 5/1996 | Van et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,555 A | 10/1996 | Froehler et al. |
| 5,567,811 A | 10/1996 | Misiura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci et al. |
| 5,596,091 A | 1/1997 | Switzer |
| 5,597,909 A | 1/1997 | Urdea et al. |
| 5,602,240 A | 2/1997 | Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bischofberger et al. |
| 5,637,459 A | 6/1997 | Burke et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci et al. |
| 5,658,873 A | 8/1997 | Bertsch-Frank et al. |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,700,920 A | 12/1997 | Altmann et al. |
| 5,714,331 A | 2/1998 | Buchardt et al. |
| 5,719,262 A | 2/1998 | Buchardt et al. |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,747 A | 8/1998 | Schally et al. |
| 5,814,666 A | 9/1998 | Green et al. |
| 5,830,653 A | 11/1998 | Froehler et al. |
| 5,955,589 A | 9/1999 | Cook et al. |
| 6,005,096 A | 12/1999 | Matteucci et al. |
| 6,051,698 A | 4/2000 | Janjic et al. |
| 6,239,116 B1 | 5/2001 | Krieg et al. |
| 6,271,209 B1 | 8/2001 | Smith et al. |
| 6,406,705 B1 | 6/2002 | Davis et al. |
| 6,677,153 B2 | 1/2004 | Iversen |
| 7,223,833 B1 | 5/2007 | Nielsen et al. |
| 7,667,004 B2 | 2/2010 | Zhong et al. |
| 7,824,473 B2 | 11/2010 | Mirkin et al. |
| 7,833,992 B2 | 11/2010 | Vargeese et al. |
| 8,507,200 B2 | 8/2013 | Mirkin et al. |
| 8,846,080 B2 | 9/2014 | Biemans et al. |
| 8,933,046 B2 | 1/2015 | Machuy et al. |
| 8,940,310 B2 | 1/2015 | Barrat et al. |
| 9,677,075 B2 | 6/2017 | Mirkin et al. |
| 9,693,957 B2 | 7/2017 | Lin et al. |
| 9,868,955 B2 | 1/2018 | Guiducci et al. |
| 9,901,616 B2 | 2/2018 | Dhar et al. |
| 10,208,310 B2 | 2/2019 | Mader et al. |
| 2002/0172711 A1 | 11/2002 | Martin et al. |
| 2003/0026782 A1 | 2/2003 | Krieg |
| 2003/0044354 A1 | 3/2003 | Carpenter et al. |
| 2003/0147966 A1 | 8/2003 | Franzen et al. |
| 2003/0170162 A1 | 9/2003 | Nayfeh et al. |
| 2004/0014956 A1 | 1/2004 | Woolf et al. |
| 2004/0033197 A1 | 2/2004 | Madar et al. |
| 2004/0053384 A1 | 3/2004 | Sligar et al. |

(56) References Cited

U.S. PATENT DOCUMENTS

| | | |
|---|---|---|
| 2004/0158051 A1 | 8/2004 | Ozkan et al. |
| 2004/0170560 A1 | 9/2004 | Fossheim et al. |
| 2004/0219565 A1 | 11/2004 | Kauppinen et al. |
| 2005/0130167 A1 | 6/2005 | Bao et al. |
| 2006/0014191 A1 | 1/2006 | Lao et al. |
| 2006/0083781 A1 | 4/2006 | Shastri et al. |
| 2006/0292174 A1 | 12/2006 | De et al. |
| 2007/0243136 A1 | 10/2007 | Fisher et al. |
| 2007/0298257 A1 | 12/2007 | Ludwig et al. |
| 2008/0175893 A1 | 7/2008 | Huang et al. |
| 2008/0181928 A1 | 7/2008 | Hakimi-Mehr et al. |
| 2008/0194463 A1 | 8/2008 | Weller et al. |
| 2008/0311182 A1 | 12/2008 | Ferrari et al. |
| 2009/0018028 A1 | 1/2009 | Lindsay et al. |
| 2009/0053169 A1 | 2/2009 | Castillo et al. |
| 2009/0211445 A1 | 8/2009 | Mirkin et al. |
| 2009/0322327 A1 | 12/2009 | Gao |
| 2010/0003317 A1 | 1/2010 | Akinc et al. |
| 2010/0092486 A1 | 4/2010 | Kandimalla et al. |
| 2010/0144848 A1 | 6/2010 | Vogel et al. |
| 2010/0166842 A1 | 7/2010 | Lu et al. |
| 2010/0167290 A1 | 7/2010 | Elghanian et al. |
| 2011/0020242 A1 | 1/2011 | Zheng et al. |
| 2011/0052680 A1 | 3/2011 | Hendrickson et al. |
| 2011/0052697 A1 | 3/2011 | Farokhzad et al. |
| 2011/0159081 A1 | 6/2011 | Biemans et al. |
| 2011/0223257 A1 | 9/2011 | Zhao et al. |
| 2011/0229529 A1 | 9/2011 | Irvine et al. |
| 2011/0237435 A1 | 9/2011 | Ryan |
| 2012/0149843 A1 | 6/2012 | Chien et al. |
| 2012/0282186 A1 | 11/2012 | Mirkin et al. |
| 2013/0028857 A1 | 1/2013 | Gao et al. |
| 2013/0089614 A1 | 4/2013 | Zhang et al. |
| 2013/0123333 A1 | 5/2013 | Mirkin et al. |
| 2013/0149374 A1 | 6/2013 | Lee et al. |
| 2013/0196951 A1 | 8/2013 | Schoenfisch et al. |
| 2013/0217124 A1* | 8/2013 | Mirkin .................. C12N 15/85 435/375 |
| 2013/0252852 A1 | 9/2013 | Pfeiffer et al. |
| 2013/0295129 A1 | 11/2013 | Irvine et al. |
| 2013/0315831 A1 | 11/2013 | Shi et al. |
| 2014/0065425 A1 | 3/2014 | Bogdanov |
| 2015/0111790 A1 | 4/2015 | Ategeka et al. |
| 2016/0068839 A1 | 3/2016 | Mirkin et al. |
| 2016/0108123 A1 | 4/2016 | Freeman et al. |
| 2016/0186178 A1 | 6/2016 | Radovic-Moreno et al. |
| 2016/0194642 A1 | 7/2016 | Gryaznov et al. |
| 2016/0237429 A1 | 8/2016 | Cubillos-Ruiz et al. |
| 2016/0274134 A1 | 9/2016 | Mutharasan et al. |
| 2016/0310425 A1 | 10/2016 | Mirkin et al. |
| 2017/0157048 A1 | 6/2017 | Radovic-Moreno et al. |
| 2018/0072810 A1 | 3/2018 | Afar et al. |
| 2018/0222982 A1 | 8/2018 | Dranoff et al. |

FOREIGN PATENT DOCUMENTS

| | | |
|---|---|---|
| EP | 2162117 A2 | 3/2010 |
| EP | 2399608 A1 | 12/2011 |
| WO | 96/34876 A1 | 11/1996 |
| WO | 97/12896 A1 | 4/1997 |
| WO | 98/39352 A1 | 9/1998 |
| WO | 99/14226 A2 | 3/1999 |
| WO | 03/86280 A2 | 10/2003 |
| WO | 2005/063201 A2 | 7/2005 |
| WO | 2005/063288 A1 | 7/2005 |
| WO | 2007/008463 A2 | 1/2007 |
| WO | 2007/047455 A2 | 4/2007 |
| WO | 2007/064857 A2 | 6/2007 |
| WO | 2007/096134 A1 | 8/2007 |
| WO | 2008/014979 A2 | 2/2008 |
| WO | 2008/151022 A2 | 12/2008 |
| WO | 2008/151049 A2 | 12/2008 |
| WO | 2009/061515 A1 | 5/2009 |
| WO | 2009/073984 A1 | 6/2009 |
| WO | 2009/120887 A2 | 10/2009 |
| WO | 2010/105209 A1 | 9/2010 |
| WO | 2012/055933 A1 | 5/2012 |
| WO | 2012/068470 A2 | 5/2012 |
| WO | 2013/012628 A2 | 1/2013 |
| WO | 2013/049941 A1 | 4/2013 |
| WO | 2013/151771 A1 | 10/2013 |
| WO | 2014/169264 A2 | 10/2014 |
| WO | 2015/013673 A1 | 1/2015 |
| WO | 2015/013675 A1 | 1/2015 |
| WO | 2015/187966 A1 | 12/2015 |
| WO | 2017/020980 A1 | 2/2017 |
| WO | 2017/035278 A1 | 3/2017 |
| WO | 2017/129365 A1 | 8/2017 |
| WO | 2018/067302 A2 | 4/2018 |

OTHER PUBLICATIONS

Lee et al., Silver nanoparticle-oligonucleotide conjugates based on DNA with triple cyclic disulfide moieties, Nano Lett., 7(7):2112-2115 (2007).

Lesieur et al., Size analysis and stability study of lipid vesicles by high-performance gel exclusion chromatography, turbidity. and dynamic light scattering, Analytical Biochemistry, 192(2):334-343 (1991).

Li et al., Combination Delivery of Antigens and CpG by Lanthanides-Based Core-Shell Nanoparticles for Enhanced Immune Response and Dual-Mode Imaging, Advanced Healthcare Materials, 2(10):1309-1313 (2013).

Li et al., Encapsulation of a Nerve Agent Detoxifying Enzyme by a Mesoporous Zirconium Metal-Organic Framework Engenders Thermal and Long-Term Stability, J. Am. Chem. Soc., 138(26):8052-8055 (2016).

Li et al., Hierarchically Engineered Mesoporous Metal-Organic Frameworks toward Cell-free Immobilized Enzyme Systems, Chem, 4(5):1022-1034 (2018).

Li et al., Molecular spherical nucleic acids, PNAS, 115(17):4340-4344 (2018).

Li et al., Nucleolin-targeting liposomes guided by aptamer AS1411 for the delivery of siRNA for the treatment of malignant melanomas, Biomaterials, 35(12):3840-3850 (2014).

Li et al., Reversible and Chemically Programmable Micelle Assembly with DNA Block-Copolymer Amphiphiles, Nano Lett., 4(6):1055-1058 (2004).

Li et al., Synthesis of nanocrystals of Zr-based metal-organic frameworks with csq-net: significant enhancement in the degradation of a nerve agent simulant, Chem. Commun., 51(54):10925-10928 (2015).

Li et al., Thermal stability of DNA functionalized gold nanoparticles, Bioconjugate Chem., 24:1790-1797 (2013).

Li et al., Toward Design Rules for Enzyme Immobilization in Hierarchical Mesoporous Metal-Organic Frameworks, Chem, 1(1):154-169 (2016).

Lian et al., Enzyme—MOF (metal-organic framework) composites, Chem. Soc. Rev., 46(11):3386-3401 (2017).

Lian et al., High efficiency and long-term intracellular activity of an enzymatic nanofactory based on metal-organic frameworks, Nat. Commun., 8(1):1-10 (2017).

Liang et al., Biomimetic mineralization of metal-organic frameworks as protective coatings for biomacromolecules, Nat. Commun., 6:7240 (2015).

Libanati et al., The distribution of the water-soluble inorganic orthophosphate ions within the cell: accumulation in the nucleus. Electron probe microanalysis, J. Cell Biol., 42(3):754-765 (1969).

Lin et al., Gold Nanoparticle Delivery of Modified CpG Stimulates Macrophases and Inhibits Tumor Growth for Enhanced Immunotherapy, Plos One, 8(5):e63550 (2013).

Liu et al., DNA-based micelles: synthesis, micellar properties and size-dependent cell permeability, Chemistry, 16:3791-3797 (2010).

Liu et al., Membrane anchored immunostimulatory oligonucleotides for in vivo cell modification and localized immunotherapy, Angew. Chem. Int. Ed. Engl., 50(31):7052-7055 (2011).

(56) References Cited

OTHER PUBLICATIONS

Liu et al., Novel trypsin-FITC@MOF bioreactor efficiently catalyzes protein digestion, J. Mater. Chem. B., 1(7):928-932 (2013).
Liu et al., Silica nanoparticle supported lipid bilayers for gene delivery, Chem. Commun., 5100-5102 (2009).
Lykourinou et al., Immobilization of MP-11 into a mesoporous metal-organic framework, MP-11@mesoMOF: a new platform for enzymatic catalysis, J. Am. Chem. Soc. 133(27):10382-10385 (2011).
Lytton-Jean et al., Highly Cooperative Behavior of Peptide Nucleic Acid Linked DNA Modified Gold Nanoparticle and Combo Polymer Aggregates, Advanced Materials, 21(6):706-709 (2009).
Macfarlane et al., Nanoparticle superlattice engineering with DNA, Science, 334(6053):204-208 (2011).
Mangsbo et al., Enhanced Tumor Eradication by Combining CTLA-4 or PD-1 Blockage with CpG Therapy, Journal of Immunotherapy, 33(3):225-235 (2010).
Martin et al., Ein neur Zugang zu 2'-O- alkylribonucleosiden and Eigenschaften deren oligonucleotide, Hely. Chim. Acta., 78:486-504 (1995).
Massich et al., Regulating Immune Response Using Polyvalent Nucleic Acid-Gold Nanoparticle Conjugates, Molecular Pharmaceutics, 6(6):1934-1940 (2009).
McAllister et al., Polymeric nanogels produced via inverse microemulsion polymerization as potential gene and antisense delivery agents, J. Am. Chem. Soc., 124:15198-15207 (2002).
McGuire et al., The surface chemistry of metal-organic frameworks, Chem. Commun(Camb), 51(25):5199-5217 (2015).
Mesmaeker et al., Backbone modifications in oligonucleotides and peptide nucleic acid systems, Curr. Opin. in Struct. Biol., 5:343-355 (1995).
Mirkin et al., A DNA-based method for rationally assembling nanoparticles into macroscopic materials, Natur, 382:607-609 (1996).
Mohamed et al., Effect of toll-like receptor 7 and 9 targeted therapy to prevent the development of hepatocellular carcinoma, Liver Int., 35(3):1063-1076 (2015).
Mohamed et al., TLR9 mediates S. aureus killing inside osteoblasts via induction of oxidative stress, BMC Microbiology, 16(article 230):8 (2016).
Mondloch et al., Vapor-phase metalation by atomic layer deposition in a metal-organic framework, J. Am. Chem. Soc., 135(28):10294-10297 (2013).
Morris et al., Nucleic acid-metal organic framework (MOF) nanoparticle conjugates, J. Am. Chem. Soc., 136(20):7261-7264 (2014).
Morris et al., Role of modulators in controlling the colloidal stability and polydispersity of the UiO-66 metal-organic framework, ACS Appl. Mater. Interfaces, 9(39):33413-33418 (2017).
Morris et al., Synthesis, structure, and metalation of two new highly porous zirconium metal-organic frameworks, Inorg. Chem., 51(12):6443-6445 (2012).
Nakayama et al., Structural study of phosphate groups in layered metal phosphates by high-resolution solid-state 31P NMR spectroscopy, J. Mater. Chem., 7:1063-1066 (1997).
Narayan et al., The sequence—specific cellular uptake of spherical nucleic acid nanoparticle conjugates, Small, 11(33):4173-4182 (2015).
Nielsen et al., Sequence—selective recognition of DNA by strand displacement with a thymine—substituted polyamide, Science, 254:1497-500 (1991).
Nikolov et al., Bias-dependent admittance in hybrid bilayer membranes, Langmuir, 22(17):7156-7158 (2006).
Nonglaton et al., New approach to oligonucleotide microarrays using zirconium phosphonate-modified surfaces, J. Am. Chem. Soc., 126(5):1497-1502 (2004).
Nykypanchuk et al., DNA-guided crystallization of colloidal nanoparticles, Nature, 451(7178):549-552 (2008).
O'Brien et al., Universal noble metal nanoparticle seeds realized through iterative reductive growth and oxidative dissolution reactions, J. Am. Chem. Soc., 136(21):7603-7606 (2014).
Ozpolat et al., Nanomedicine based approaches for the delivery of siRNA in cancer, J. Intern. Med., 267(1):44-53 (2010).
Park et al., DNA-programmable nanoparticle crystallization, Nature, 451(7178):553-556 (2008).
Park et al., Size-Controlled Synthesis of Porphyrinic Metal-Organic Framework and Functionalization for Targeted Photodynamic Therapy, J. Am. Chem. Soc., 138(10):3518-3525 (2016).
Patel et al., Scavenger receptors mediate cellular uptake of polyvalent oligonucleotide—functionalized gold nanoparticles, Bioconjugate Chem., 21(12):2250-2256 (2010).
Peter et al., Characterization of suppressive oligodeoxynucleotides that inhibit Toll-like receptor- 9—mediated activation of innate immunity, Immunology, 123(1):118-128 (2008).
Petros et al., Strategies in the design of nanoparticles for therapeutic applications, Nat. Rev. Drug Discovery, 9(8):615-627 (2010).
Pfeiffer et al., Bivalent Cholesterol-Based Coupling of Oligonucleotides to Lipid Membrane Assemblies, J. Am. Chem. Soc., 126:10224-10225 (2004).
Freier et al., The ups and downs of nucleic acid duplex stability: structure-stability studies on chemically-modified DNA:RNA duplexes, Nucl. Acid. Res., 25:4429-4443 (1997).
Frohlich et al., The role of surface charge in cellular uptake and cytotoxicity of medical nanoparticles, Int. J. Nanomed., 7:5577-5591 (2012).
Fu et al., Promises and pitfalls of intracellular delivery of proteins, Bioconjugate Chem., 25(9):1602-1608 (2014).
Ghosh et al., Intracellular delivery of a membrane-impermeable enzyme in active form using functionalized gold nanoparticles, J. Am. Chem. Soc., 132(8):2642-2645 (2010).
Giljohann et al., Gene regulation with polyvalent siRNA-nanoparticle conjugates, J. Am. Chem. Soc., 131(6):2072-2073 (2009).
Gkaniatsou et al., Metal—organic frameworks: a novel host platform for enzymatic catalysis and detection, Mater. Horiz., 4:55-63 (2017).
Grancharov et al., Bio-functionalization of monodisperse magnetic nanoparticles and their use as biomolecular labels in a magnetic tunnel junction based sensor, J. Phys. Chem. B., 109(26):13030-13035 (2005).
Grijalva et al., Oligonucleotide delivery: a patent review (2010-2013), Expert Opin. Ther. Pat., 24(7):801-819 (2014).
Gu et al., Tailoring nanocarriers for intracellular protein delivery, Chem. Soc. Rev., 40(7):3638-3655 (2011).
Gunnarsson et al., Liposome-based chemical barcodes for single molecule DNA detection using imaging mass soectrometry, Nano. Lett., 10:732-737 (2010).
Gunnarsson et al., Single-molecule detection and mismatch discrimination of unlabeled DNA targets, Nano Lett., 8:183-188 (2008).
He et al., DNA-assembled core-satellite upconverting-metal-organic framework nanoparticle superstructures for efficient photodynamic therapy, Small, 13, 1700504 (2017).
He et al., Nanomedicine applications of hybrid nanomaterials built from metal-ligand coordination bonds: Nanoscale metal-organic frameworks and nanoscale coordination polymers, Chem. Rev., 115(19):11079-11108 (2015).
He et al., Nanoscale metal-organic frameworks for the co-delivery of cisplatin and pooled siRNAs to enhance therapeutic efficacy in drug-resistant ovarian cancer cells, J. Am. Chem. Soc., 136(14):5181-5184 (2014).
Hoffman, Green fluorescent protein imaging of tumour growth, metastasis, and angiogenesis in mouse models, Lancet Oncol., 3(9):546-556 (2002).
Hope et al., Generation of multilamellar and unilamellar phospholipid vesicles, Chemistry and Physics of Lipids, 40:89-107 (1986).
Hope et al., Production of large unilamellar vesicles by a rapid extrusion procedure: characterization of size distribution, trapped volume and ability to maintain a membrane potential, Biochim Biophys Acta, Jan. 10, 1985, vol. 812, No. 1, pp. 55-65.
Horcajada et al., Porous metal-organic-framework nanoscale carriers as a potential platform for drug delivery and imaging, Nat. Mater., 9(2):172-178 (2010).
Houot et al., T-cell modulation combined with intratumoral CpG cures lymphoma in a mouse model without the need for chemotherapy, Blood, 113(15):3546-3552 (2009).

(56) References Cited

OTHER PUBLICATIONS

Hurst et al., Maximizing DNA loading on a range of gold nanoparticle sizes, Anal. Chem., 78(24):8313-8318 (2006).
Hwang et al., Amine grafting on coordinatively unsaturated metal centers of MOFs: consequences for catalysis and metal encapsulation, Angew. Chem. Int. Ed. Engl., 47(22):4144-4148 (2008).
International Application No. PCT/US18/42050, International Preliminary Report on Patentability, dated Jan. 23, 2020.
International Application No. PCT/US18/42050, International Search Report and Written Opinion, dated Jan. 15, 2019.
International Preliminary Reporton Patentability, United States Patent Office, PCT/US2014/068429, dated Jun. 7, 2016.
International Search Report and Written Opinion of the International Search Authority, United States Patent Office, PCT/US2014/068429, dated Aug. 10, 2015.
Jahn et al., Microfluidic directed formation of liposomes of controlled size, Langmuir, 23(11):6289-6293 (2007).
Jakobsen et al., Assembly of liposomes controlled by triple helix formation, Bioconjugate Chem., 24:1485-1495 (2013).
Jensen et al., Spherical nucleic acid nanoparticle conjugates as an RNAi-based therapy for glioblastoma, Sci. Trans. Med., 5:209ra152 (2013).
Jiang et al., Pore surface engineering with controlled loadings of functional groups via click chemistry in highly stable metal-organic frameworks, J. Am. Chem. Soc., 134(36):14690-14693 (2012).
Jiang et al., Size-controlled synthesis of MIL-101(Cr) nanoparticles with enhanced selectivity for $CO_2$ over $N_2$†, Crystengcomm., 13:6916-6919 (2011).
Jones et al., Nanomaterials programmable materials and the nature of the DNA bond, Science, 347(6224):1260901 (2015).
Kahn et al., Stimuli-responsive DNA-functionalized metal-organic frameworks (MOFs), Adv. Mater., 29(6):1602782 (2017).
Kandimalla et al., Secondary structures in CpG oligonucleotides affect immunostimulatory activity, Biochemical and Biophysical Research Communications, 306:948-953 (2003).
Kasuya et al., Bio-nanocapsule-liposome conjugates for in vivo pinpoint drug and gene delivery, Methods Enzymol., 464:147-166 (2009).
Katz, The reversible reaction of sodium thymonucleate and mercuric chloride, J. Am. Chem. Soc., 74(9):2238-2245 (1951).
Kelly et al., Targeted liposomal drug delivery to monocytes and macrophages, Journal of Drug Delivery, Article ID 727241:1-11 (2011).
Kelty et al., High-throughput synthesis and characterization of nanocrystalline porphyrinic zirconium metal-organic frameworks, Chem. Commun(Camb), 52(50):7854-7857 (2016).
Kim et al., Cationic solid lipid nanoparticles reconstituted from low density lipoprotein components for delivery of siRNA, Mol. Pharm., 5(4):622-631 (2008).
Kim et al., Effect of bovine serum albumin on the stability of methotrexate—encapsulated liposomes, Arch. Pharmacal Res, 14:336-341 (1991).
Kopylov et al., Combinatorial Chemistry of Nucleic Acids: SELEX, Molecular Biology, 34(6):940-954 (2000).
Kopylov, Combinatorial Chemistry of Nucleic Acids: Selex, Molekulyarnaya Biologiya, 34(6):1097-1113 (2000).
Kosturko et al., The crystal and molecular structure of a 2:1 complex of 1-methylthymine-mercury (II), Biochemistry, 13(19):3949-3952 (1974).
Kreig, Toll-like receptor 9 (TLR9) agonists in the treatment of cancer, Oncogene, 27:116-167 (2008).
Kroschwitz ed., The Concise Encyclopedia of Polymer Science and Engineering, John Wiley & Sons, 858-9 (1990).
Kumar et al., High-yield synthesis and optical response of gold nanostars, Nanotechnology, 19(1):015606 (2008).
Langer et al., Designing materials for biology and medicine, Nature, 428(6982):487-492 (2004).
Laouini et al., Preparation, characterization and applications of liposomes: state of the art, Journal of colloid science and biotechnology, 1:148-168 (2012).

Lawrence et al., Supercharging proteins can impart unusual resilience, J. Am. Chem. Soc., 129(33):10110-2 (2007).
Leader et al., Protein therapeutics: a summary and pharmacological classification, Nat. Rev. Drug Discovery, 7(1):21-39 (2008).
Lee et al., Imageable Antigen-Presenting Gold Nanoparticle Vaccines for Effective Cancer Immunotherapy In vivo, Angewandte Chemie International Edition, 51(35):8800-8805 (2012).
Pfeiffer et al., Quantification of oligonucleotide modifications of small unilamellar lipid vesicles, Anal. Chem., 78:7493-7498 (2006).
Prigodich et al., Nano-flares for mRNA regulation and detection, ACS Nano, 3(8):2147-2152 (2009).
Radovic-Moreno et al., Immunomodulatory spherical nucleic acids, Proc. Natl. Acad. Sci. U.S.A., 112(13):3892-3897 (2015).
Roder et al., Multifunctional nanoparticles by coordinative aelf-assembly of his-tagged units with metal-organic frameworks, J. Am. Chem. Soc., 139(6):2359-2368 (2017).
Rosi et al., Nanostructures in biodiagnostics, Chem. Rev., 105(4):1547-1562 (2005).
Rosi et al., Oligonucleotide—modified gold nanoparticles for intracellular gene regulation, Science, 312(5776):1027-1030 (2006).
Ruyra et al., Synthesis, culture medium stability, and in vitro and in vivo zebrafish embryo toxicity of metal-organic framework nanoparticles, Chem., 21(6):2508-2518 (2015).
Sanghvi, Chapter 15, Antisense research and applications, Ed. S. T. Crooke and B. Lebleu, CRC Press, 289-302 (1993).
Schwarze et al., In vivo protein transduction: delivery of a biologically active protein into the mouse, Science, 285:1569-1572 (1999).
Seferos et al., Locked nucleic acid-nanoparticle conjugates, ChemBioChem, 8:1230-1232 (2007).
Seferos et al., Nano-flares: probes for transfection and mRNA detection in living cells, J. Am. Chem. Soc., 129(50):15477-15479 (2007).
Seferos et al., Polyvalent DNA nanoparticle conjugates stabilize nucleic acids, Nano Lett., 9(1):308-311 (2009).
Senior et al., Stability of small unilamellar liposomes in serum and clearance from the circulation: the effect of the phosoholipid and cholesterol components. Life Sci., 30:2123-2136 (1982).
Shearer et al., Defect engineering: tuning the porosity and composition of the metal-organic framework UiO-66 via modulated synthesis, Chem. Mater., 28(11):3749-3761 (2016).
Shih et al., Trypsin-immobilized metal-organic framework as a biocatalyst in proteomics analysis, Chempluschem., 77(11):982-986 (2012).
Sindoro et al., Colloidal-sized metal-organic frameworks: synthesis and applications, Acc. Chem. Res., 47(2):459-469 (2014).
Sokolova et al., The use of calcium phosphate nanoparticles encapsulating Toll-like receptor ligands and the antigen hemagglutinin to induce dendritic cell maturation and T cell activation, Biomaterials, 31:5627-5633 (2010).
Stengel et al., Determinants for Membrane Fusion Induced by Cholesterol-Modified DNA Zippers, J. Phvs. Chem. B., 112:8264-74 (2008).
Stengel et al., DNA-Induced Programmable Fusion of Phospholipid Vesicles, J. Am. Chem. Soc., 129:9584-5 (2007).
Sulkowski et al., The influence of temperature, cholesterol content and pH on liposome stability, J. Mol. Struct., 744-747:737-747 (2005).
Switaj et al., CpG Immunostimulatory Oligodeoxynucleotide 1826 Enhances Antitumor Effect of Interleukin 12 Gene-Modified Tumor Vaccine in a Melanoma Model in Mice, Clinical Cancer Research, 10:4165-4175 (2004).
Taylor-Pashow et al., Postsynthetic modifications of iron-carboxylate nanoscale metal-organic frameworks for imaging and drug delivery, J. Am. Chem. Soc., 131(40):14261-14263 (2009).
Thomas, The Interaction of $HgCl_2$ with Sodium Thymonucleate, J. Am. Chem. Soc., 76(23):6032-6034 (1954).
Tincer et al., Immunostimulatory activity of polysccharidepoly (I:C) nanoparticles, Biomaterial., 32(18):4275-4282 (2011).
Torchilin, Intracellular delivery of protein and peptide therapeutics, Drug Discovery Today: Technol., 5(2-3):e95-e103 (2008).
Tuerk et al., Systematic evolution of ligands by exponential enrichment: RNA ligands to bacteriophage T4 DNA polymerase, Science, 249(4968):505-510 (1990).

(56) References Cited

OTHER PUBLICATIONS

Versluis et al., In situ modification of plain liposomes with lipidated coiled coil forming peptides induces membrane fusion, J. Am. Chem. Soc., 135:8057-8062 (2013).
Wang et al., Colloidal crystal engineering with metal-organic framework nanoparticles and DNA, Nat. Commun., 11(1):2495 (2020).
Wang et al., DNA-Functionalized Metal-Organic Framework Nanoparticles for Intracellular Delivery of Proteins, J. Am. Chem. Soc., 141(6):2215-2219 (2019).
Wang et al., General and direct method for preparing oligonucleotide-functionalized metal-organic framework nanoparticles, J. Am. Chem. Soc., 139(29):9827-9830 (2017).
Wang et al., Surface-specific functionalization of nanoscale metal—organic frameworks, Angew. Chem. Int. Ed. Engl., 54(49):14738-14742 (2015).
Wei et al., Polyvalent Immunostimulatory Nanoagents with Self-Assembled CpG Oligonucleotide—Conjugated Gold Nanoparticles, Angewandte Chemie International Edition, 51(5):1202-1206 (2012).
West et al., Recognition and signaling by toll-like receptors, Annu. Rev. Cell Dev. Biol., 22:409-37 (2006).
Whitehead et al., Knocking down barriers: advances in siRNA delivery, Nat. Rev. Drug. Discov., 8:129-138 (2009).
Willis et al., Liposome-Anchored Vascular Endothelial Growth Factor Aptamers, Bioconjugate Chem., 9:573-582 (1998).
Wilson et al., pH-Responsive Nanoparticle Vaccines for Dual-Delivery of Antigens and Immunostimulatory Oligonucleotides, ACS NANO, 7(5):3912-3925 (2013).
Wu et al., DNA aptamer-micelle as an efficient detection/delivery vehicle toward cancer cells, Proc. Natl. Acad. Sci. USA., 107(1):5-10 (2010).
Xing et al., Selective delivery of an anticancer drug with aptamer-functionalized liposomes to breast cancer cells in vitro and in vivo, J. Mater. Chem. B., 1:5288-5297 (2013).
Xu et al., Protein encapsulation in unilamellar liposomes: high encapsulation efficiency and a novel technique to assess lipid-protein interaction, Pharm. Res., 29(7):1919-1931 (2012).
Yamane et al., On the complexing of desoxyribonucleic acid (DNA) by mercuric Ion1, J. Am. Chem. Soc., 83(12):2599-2607 (1961).
Yan et al., Aptamers and aptamer targeted delivery, RNA Biol., 6(3):316-320 (2009).
Yin et al., Supramolecular self-assembled nanoparticles mediate oral delivery of therapeutic TNF-? siRNA against systemic inflammation, Anaew. Chem. Int. Ed. Enal., 125(22):5757-5761 (2013).
Young et al., Hollow spherical nucleic acids for intracellular gene regulation based upon biocompatible silica shells, Nano Lett., 12(7):3867-3871 (2012).
Zhang et al., A general approach to DNA-programmable atom equivalents, Nat. Mater., 12(8):741-746 (2013).
Zhang et al., An amine-functionalized metal-organic framework as a sensing platform for DNA detection, Chem. Commun(Camb), 50(81):12069-12072 (2014).
Zhang et al., An extremely stable and orthogonal DNA base pair with a simplified three-carbon backbone, J. Am. Chem. Soc., 127(1):74-75 (2005).
Zhang et al., Antibody-linked spherical nucleic acids for cellular targeting, J. Am. Chem. Soc., 134:16488-91 (2012).
Zhang et al., Informational Liposomes: Complexes Derived from Cholesteryl-conjugated Oligonucleotides and Liposomes, Tetrahedron Letters, 37(35):6243-6246 (1996).
Zhang et al., Metal-organic-framework-supported immunostimulatory oligonucleotides for enhanced immune response and imaging, Chem Commun., 53(11):1840-1843 (2017).
Zhang et al., PowerBLAST: a new network BLAST application for interactive or automated sequence analysis and annotation, Genome Res., 7(6):649-656 (1997).
Agbasi-Porter et al., Transcription inhibition using oligonucleotide-modified gold nanoparticles, Bioconiugate Chem., 17(5):1178-83 (2006).

Alemdaroglu et al., DNA block copolymer micelles—A combinatorial tool for cancer tanotechnology, Advanced materials, 20:899 (2008).
Ali et al., Vaccines combined with immune checkpoint antibodies promote cytotoxic T-cell activity and tumor eradication, Cancer Immunology Research, 4(2):95-100 (2016).
Alivisatos et al., Organization of 'nanocrystal molecules' using DNA, Nature, 382(6592):609-611 (1996).
Altschul et al., Basic local alignment search tool, J. Mol. Biol., 215(3):403-410 (1990).
Andrews et al., Conjugation of lipid and CpG-containing oligonucleotide yields an efficient method for liposome incorporation, bioconjugate Chem., 22:1279-1286 (2011).
Auyeung et al., Transitioning DNA-engineered nanoparticle superlattices from solution to the solid state, Adv. Mater., 24(38):5181-5186 (2012).
Baati et al., In depth analysis of the in vivo toxicity of nanoparticles of porous iron(iii) metal-organic frameworks†, Chem. Sci., 4:1597-1607 (2013).
Bae et al., Targeted drug delivery to tumors: myths, reality and possibility, J. Control Release, 153(3):198-205 (2011).
Banchelli et al., Phospholipid membranes decorated by cholesterol-based oligonucleotides as soft hybrid nanostructures, J. Phys. Chem. B., 112:10942-10952 (2008).
Banga et al., Liposomal spherical nucleic acids, J. Am. Chem. Soc., 136(28):9866-9869 (2014).
Bergman et al., Surface plasmon amplification by stimulated emission of radiation: quantum generation of coherent surface plasmons in nanosystems, Phys. Rev. Lett., 90(2):027402 (2003).
Bouderault et al., Nanoscale tools to selectively destroy cancer cells, Chem. Commun., (18):2118-2120 (2008).
Briley et al., In Nanomaterials for Biomedicine; American Chemical Society, 1119:1-20 (2012).
Brodin et al., DNA-mediated cellular delivery of functional enzymes, J. Am. Chem. Soc., 137(47):14838-14841 (2015).
Brodin et al., DNA-mediated engineering of multicomponent enzyme crystals, Proc. Natl. Acad. Sci. U.S.A., 112(15):4564-4569 (2015).
Bunge et al., Lipophilic oligonucleotides spontaneously insert into lipid membranes, bind complementary DNA strands, and sequester into lipid-disordered domains, Langmuir, Mar. 17, 2007, vol. 23, No. 8, pp. 4455-4464.
Burgess, Liposome preparation—Avanti(Registered) Polar Lipids, Sigma-Aldrich, 3 pages (1998).
Cagdas et al., Liposomes as potential drug carrier systems for drug delivery, In Application of Nanotechnology in Drug Delivery, Chapter 1, 51 pages (2014).
Cai et al., An electrochemical DNA hybridization detection assay based on a silver nanoparticle label, Analyst., 127(6):803-808 (2002).
Calabrese et al., Biocompatible infinite-coordination-polymer nanoparticle-nucleic-acid conjugates for antisense gene regulation, Angew. Chem. Int. Ed. Engl., 54(2):476-480 (2015).
Cao et al., Immobilization of bacillus subtilis lipase on a Cu-BTC based hierarchically porous metal-organic framework material: a biocatalyst for esterification, Dalton Trans., 45(16):6998-7003 (2016).
Cao et al., Reversible cell-specific drug delivery with aptamer-functionalized liposomes, Angew. Chem. Int. Ed., 48:6494-6498 (2009).
Capaccioli et al., Cationic lipids improve antisense oligonucleotide uptake and prevent degradation in cultured cells and inhuman serum, Biochem. Biophys. Res. Commun., 197(2):818-825 (1993).
Cavka et al., A new zirconium inorganic building brick forming metal organic frameworks with exceptional stability, J. Am. Chem. Soc., 130(42):13850-13851 (2008).
Chen et al., Acid-resistant mesoporous metal-organic framework toward oral insulin delivery: protein encapsulation, protection, and release, J. Am. Chem. Soc., 140(17):5678-5681 (2018).
Chien et al., DNA-nanoparticle micelles as supramolecular fluorogenic substrates enabling catalytic signal amplification and detection by DNAzyme probes, Chem. Commun., 47:167-169 (2011).
Chinnathambi et al., Binding mode of CpG oligodeoxynucleotides to nanoparticles regulates bifurcated cytokine induction via Toll-like receptor 9, Scientific Reports, 2(534):1-9 (2012).

(56) References Cited

OTHER PUBLICATIONS

Cho et al., Targeted delivery of siRNA-generating DNA nanocassettes using multifunctional nanoparticles, Small 9(11):1964-1973 (2013).

Cho et al., Therapeutic nanoparticles for drug delivery in cancer, Clin. Cancer Res., 14(5):1310-1316 (2008).

Choi et al., Mechanism for the endocytosis of spherical nucleic acid nanoparticle conjugates, Proc. Natl. Acad. Sci. U.S.A., 110(19):7625-7630 (2013).

Cook, Medicinal chemistry of antisense oligonucleotides-future opportunities, Anti-Cancer Drug Design, 6(6):585-607 (1991).

Cottrell, The strengths of chemical bonds; Butterworth scientific publications: London, 310 (1954).

Crawford et al., Peptide aptamers: tools for biology and drug discovery, Briefings in Functional Genomics and Proteomics, 2(1):72-79 (2003).

Cronican et al., Potent delivery of functional proteins into Mammalian cells in vitro and in vivo using a supercharged protein, ACS Chem. Biol., 5(8):747-752 (2010).

Cutler et al., Polyvalent nucleic acid nanostructures, J. Am. Chem. Soc., 133(24):9254-9257 (2011).

Cutler et al., Polyvalent oligonucleotide iron oxide nanoparticle "click" conjugates, Nano Lett., 10(4):1477-1480 (2010).

Cutler et al., Spherical nucleic acids, J. Am. Chem. Soc., 134(3):1376-1391 (2012).

D'Astolfo et al., Efficient intracellular delivery of native proteins, Cell, 161(3):674-690 (2015).

Dave et al., Programmable assembly of DNA-functionalized liposomes by DNA, ACS Nano, 5(2):1304-1312 (2011).

Desnick et al., Enzyme replacement and enhancement therapies: lessons from lysosomal disorders, Nat. Rev. Genet., 3(12):954-966 (2002).

Doonan et al., Metal-organic frameworks at the biointerface: Synthetic strategies and applications, Acc. Chem. Res., 50(6):1423-1432 (2017).

Dua et al., Liposome: Methods of Preparation and Applications, International Journal of Pharmaceutical Studies and Research, 3(2):14-20 (2012).

Englisch et al., Chemically Modified Oligonucleotides as Probes and Inhibitors, Angew. Chem. Int. Ed., 30(6):613-629 (1991).

European Application No. 14883485, European Search Report and Opinion, dated May 9, 2017.

European Application No. 18845192.6, European Search Report and Opinion, dated Mar. 2, 2021.

Farokhzad et al., Nanomedicine: developing smarter therapeutic and diagnostic modalities, Drug Delivery Rev., 58(14):1456-1459 (2006).

Feng et al., Stable metal-organic frameworks containing single-molecule traps for enzyme encapsulation, Nat. Commun., 6:5979 (2015).

Feng et al., Zirconium-metalloporphyrin PCN-222: mesoporous metal-organic frameworks with ultrahigh stability as biomimetic catalysts, Angew. Chem. Int. Ed. Engl., 51(41):10307-10310 (2012).

Ferrari, Cancer nanotechnology: opportunities and challenges, Nature Reviews Cancer, 5:161-171 (2005).

* cited by examiner

αInset: $Zr_6O_4(OH)_4$ secondary building units (SBU).

SEQUENCE LISTING

<160> NUMBER OF SEQ ID NOS: 14

<210> SEQ ID NO 1
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: AuNP-bound assembly strand
<220> FEATURE:
<221> NAME/KEY: misc_feature
<222> LOCATION: (1)..(1)
<223> OTHER INFORMATION: HS-(Spacer)2

<400> SEQUENCE: 1
ttgttaatat gagtcgtt                                                 18

<210> SEQ ID NO 2
<211> LENGTH: 18
<212> TYPE: DNA
<213> ORGANISM: Artificial Sequence
<220> FEATURE:
<223> OTHER INFORMATION: Synthetic Polynucleotide

```
<220> FEATURE:
<221> NAME/KEY: misc_feature
<223> OTHER INFORMATION: AgNP-bound assembly strnd
<220> FEATURE:
<221> NAME/KEY: misc_feature
<222> LOCATION: (1)..(1)
<223> OTHER INFORMATION: (DS3)-(Spacer)2

<400> SEQUENCE: 2
ttgttaatat gagtcgtt                                                  18

<210> SEQ ID NO 3
<211> LENGTH: 25
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: AuNP=melt strand

<400> SEQUENCE: 3
aaggaaattc ttaaatattc gtctt                                          25

<210> SEQ ID NO 4
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: MOF-bound Strand
<220> FEATURE:
<221> NAME/KEY: misc_feature
<222> LOCATION: (1)..(1)
<223> OTHER INFORMATION: Phosphate-(Spacer)2

<400> SEQUENCE: 4
aacgactcat attaacaa                                                  18

<210> SEQ ID NO 5
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: MOF-bound complementary Strand
<220> FEATURE:
<221> NAME/KEY: misc_feature
<222> LOCATION: (1)..(1)
<223> OTHER INFORMATION: Phosphate-(Spacer)2

<400> SEQUENCE: 5
ttgttaatat gagtcgtt                                                  18

<210> SEQ ID NO 6
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: MOF-dye loading strand
<220> FEATURE:
<221> NAME/KEY: misc_feature
<222> LOCATION: (1)..(1)
<223> OTHER INFORMATION: Phosphate-(Spacer)2
```

```
<220> FEATURE:
<221> NAME/KEY: misc_feature
<222> LOCATION: (18)..(18)
<223> OTHER INFORMATION: Tamra

<400> SEQUENCE: 6
aacgactcat attaacaa                                                    18

<210> SEQ ID NO 7
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: MOF-dye loading strand #2
<220> FEATURE:
<221> NAME/KEY: misc_feature
<222> LOCATION: (1)..(1)
<223> OTHER INFORMATION: Phosphate-(Spacer)2
<220> FEATURE:
<221> NAME/KEY: misc_feature
<222> LOCATION: (18)..(18)
<223> OTHER INFORMATION: Cy5

<400> SEQUENCE: 7
aacgactcat attaacaa                                                    18

<210> SEQ ID NO 8
<211> LENGTH: 1
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: MOF-CPR-T
<220> FEATURE:
<221> NAME/KEY: misc_feature
<222> LOCATION: (1)..(1)
<223> OTHER INFORMATION: Phosphate

<400> SEQUENCE: 8 t                                                                       1

<210> SEQ ID NO 9
<211> LENGTH: 2
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: MOF-CPR-T2
<220> FEATURE:
<221> NAME/KEY: misc_feature
<222> LOCATION: (1)..(1)
<223> OTHER INFORMATION: Phosphate

<400> SEQUENCE: 9 tt                                                                      2

<210> SEQ ID NO 10
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
```

-continued

<223> OTHER INFORMATION: MOF-CPR-T20
<220> FEATURE:
<221> NAME/KEY: misc_feature
<222> LOCATION: (1)..(1)
<223> OTHER INFORMATION: Phosphate

<400> SEQUENCE: 10
tttttttttt tttttttttt                                           20

<210> SEQ ID NO 11
<211> LENGTH: 25
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: MOF-melt strand

<400> SEQUENCE: 11
ttccttattg ttaatatgag tcgtt                                     25

<210> SEQ ID NO 12
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: AzideNP-bound assembly strand
<220> FEATURE:
<221> NAME/KEY: misc_feature
<222> LOCATION: (1)..(1)
<223> OTHER INFORMATION: DBCO-TEG-(Spacer)2

<400> SEQUENCE: 12
ttgttaatat gagtcgtt                                             18

<210> SEQ ID NO 13
<211> LENGTH: 40
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: polyG
<220> FEATURE:
<221> NAME/KEY: misc_feature
<222> LOCATION: (40)..(40)
<223> OTHER INFORMATION: phosphate

<400> SEQUENCE: 13
dggtdggtdg gtdggtdggt dggtdggtdg gtdggtdggt                     40

<210> SEQ ID NO 14
<211> LENGTH: 40
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: polyG-dye
<220> FEATURE:
<221> NAME/KEY: misc_feature
<222> LOCATION: (1)..(1)
<223> OTHER INFORMATION: Tamra-dT
<220> FEATURE:
<221> NAME/KEY: misc_feature

```
<222> LOCATION: (40)..(40)
<223> OTHER INFORMATION: phosphate

<400> SEQUENCE: 14
dggtdggtdg gtdggtdggt dggtdggtdg gtdggtdggt                40
```

GENERAL AND DIRECT METHOD FOR PREPARING OLIGONUCLEOTIDE-FUNCTIONALIZED METAL-ORGANIC FRAMEWORK NANOPARTICLES

CROSS-REFERENCE TO RELATED APPLICATIONS

This is a U.S. National Phase of International Application No. PCT/US2018/042050, filed Jul. 13, 2018, which claims priority to U.S. Provisional Application No. 62/532,241, filed Jul. 13, 2017.

STATEMENT OF GOVERNMENT SUPPORT

This invention was made with government support under FA9550-14-1-0274 awarded by the Air Force Office of Scientific Research; W911NF-15-1-0151 awarded by the Army Research Office; DMR1121262 awarded by the National Science Foundation; and U54 CA199091 awarded by the National Institutes of Health. The government has certain rights in the invention.

INCORPORATION BY REFERENCE OF MATERIALS SUBMITTED ELECTRONICALLY

This application contains, as a separate part of the disclosure, a Sequence Listing in computer readable form (Filename: 2017-128_Seqlisting.txt; Size: 4,923 bytes; Created: Jul. 12, 2018), which is incorporated by reference in its entirety.

FIELD OF THE INVENTION

The present disclosure generally relates to metal-organic framework nanoparticles containing terminal phosphate-modified oligonucleotides, methods for making the same, and methods of using the same.

BACKGROUND

It is known that DNA is a versatile and powerful ligand for modifying nanomaterials by virtue of its programmable and sequence-specific interactions.[1-3] For example, by densely functionalizing DNA onto spherical nanoparticles (NPs), one can orient the oligonucleotides (3'-5' or 5'-3') and generate spherical nucleic acid-nanoparticle conjugates (SNAs),[4] which exhibit unusual biological properties that have enabled a variety of applications in research and medicine. Indeed, many biodiagnostic systems and therapeutic lead compounds for as gene regulation are now based upon SNAs.[5,6] In addition, they have become the central building blocks for crystal engineering approaches based upon the concept of DNA-programmable assembly.[7-9] Thus far, several approaches have been developed for modifying noble metal,[1,2,10] oxide,[11] quantum dot nanoparticles with DNA.[12] However, there are no general ways for directly modifying MOF nanoparticles with oligonucleotides in a preferential end-on manner. Indeed, all previous approaches have utilized either nonspecific interactions such as electrostatic adsorption and van der Waals interactions,[13,14] or required a coupling agent that is necessarily immobilized on the particle surface prior to functionalization with DNA,[15,16] rendering less control and generality.

SUMMARY

Herein, a general strategy for functionalizing MOF nanoparticles with oligonucleotides at high density is provided. Using terminal phosphate-modified oligonucleotides, the dense coordinatively unsaturated metal sites (CUS) on a MOF nanoparticle surface can be chemically addressed.[17-21] Solid-state nuclear magnetic resonance (SSNMR) spectroscopy and powder X-ray diffraction (PXRD) confirm that the DNA-functionalization of MOFs occurs by metal-phosphate coordination and that the structural integrity and porosity of the MOF architecture are preserved postmodification (FIG. 1). As proof-of-concept of generality, this approach was extended to a series of nine different MOFs, featuring four metal nodes (Zr, Fe, Cr, Al) and four different organic linkers.

Accordingly, in some aspects the disclosure provides an oligonucleotide-functionalized metal-organic framework (MOF) nanoparticle, wherein the oligonucleotide is a terminal phosphate-modified oligonucleotide and the phosphate forms a metal-phosphate bond with the metal ion of the MOF nanoparticle. In some embodiments, the MOF nanoparticle comprises zirconium (Zr), chromium (Cr), iron (Fe), and/or aluminum (Al). In further embodiments, the MOF comprises UiO-66, UiO-67-bpy, UiO68-$N_3$/PCN-58, PCN-222/MOF-545, PCN-223, PCN-224, MIL-101 (Al), MIL-101 (Fe), or MIL-101(Cr).

In some embodiments, the terminal phosphate-modified oligonucleotide has a phosphate group on its 3' end. In further embodiments, the terminal phosphate-modified oligonucleotide has a phosphate group on its 5' end. In some embodiments, a nanoparticle of the disclosure further comprises an agent selected from the group consisting of a peptide, a protein, a nanoparticle, an antibody, a small molecule, and a combination thereof, wherein the agent is encapsulated in the nanoparticle.

In some embodiments, the terminal phosphate-modified oligonucleotide comprises a $(GGT)_n$ nucleotide sequence, wherein n is 2-20. In further embodiments, density of terminal phosphate-modified oligonucleotide on the surface of the MOF nanoparticle is from about 2 pmol/$cm^2$ to about 24 pmol/$cm^2$. In some embodiments, the MOF nanoparticle comprises a plurality of terminal phosphate-modified oligonucleotides on its surface and at least one oligonucleotide regulates gene expression. In some embodiments, the at least one terminal phosphate-modified oligonucleotide is an antisense oligonucleotide. In further embodiments, the terminal phosphate-modified oligonucleotide is RNA. In still further embodiments, the RNA is small interfering RNA (siRNA).

In some aspects, the disclosure provides a method of making an oligonucleotide-functionalized MOF nanoparticle of the disclosure, comprising (a) mixing a metal ion and a multi-dentate ligand to form the MOF nanoparticle; and (b) contacting the MOF nanoparticle with a plurality of the terminal phosphate-modified oligonucleotides, thereby producing the oligonucleotide-functionalized MOF nanoparticle, such that the phosphate groups of the terminal phosphate-modified oligonucleotides associate with coordinatively unsaturated metal sites (CUS) on the MOF nanoparticle surface via a metal-phosphate bond. In some embodiments, the multi-dentate ligand comprises 2, 3, or 4 coordinating functional groups. In further embodiments, the multi-dentate ligand is a bi-dentate ligand. In still further embodiments, the multi-dentate ligand is a tri-dentate ligand. In some embodiments, the multi-dentate ligand comprises at least one carboxylate functional group. In some embodiments, the multi-dentate ligand comprises at least one heterocyclic group having at least one ring nitrogen. In further embodiments, the multi-dentate ligand comprises formic acid, acetic acid, oxalic acid, propanoic acid, butanedioic acid, (E)-butenedioic acid, benzene-1,4-dicarboxylic acid, benzene-1,3-dicarboxylic acid, benzene-1,3,5-tricarboxylic acid, 2-amino-1,4-benzenedicarboxylic acid, 2-bromo-1,4-benzenedicarboxylic acid, biphenyl-4,4'-dicarboxylic acid, biphenyl-3,3',5,5'-tetracarboxylic acid, biphenyl-3,4',5-tricarboxylic acid, 2,5-dihydroxy-1,4-benzenedicarboxylic acid, 1,3,5-tris(4-carboxyphenyl)benzene, (2E, 4E)-hexa-2,4-dienedioic acid, 1,4-naphthalenedicarboxylic acid, pyrene-2,7-dicarboxylic acid, 4,5,9,10-tetrahydropyrene-2,7-dicarboxylic acid, aspartic acid, glutamic acid, adenine, 4,4'-bypiridine, pyrimidine, pyrazine, pyridine-4-carboxylic acid, pyridine-3-carboxylic acid, imidazole, 1H-benzimidazole, 2-methyl-1H-imidazole, or a mixture thereof. In some embodiments, the multi-dentate ligand comprises terephthalic acid ($H_2BDC$), 2,2'-bipyridine-5,5'-dicarboxylic acid ($H_2BPY$), 2',5'-bis(azidomethyl)-[1,1':4', 1''-terphenyl]-4,4''-dicarboxylic acid, ($H_2TPDC-N_3$), 4,4', 4'',4'''-porphyrin tetrabenzoic acid ($H_2TCPP$), or a combination thereof. In further embodiments, the metal ion comprises a 12-connect $Zr_3$ cluster, a 6-connect $Zr_3$ cluster, a 8-connect $Zr_3$ cluster, a $Cr_3$ cluster, a $Fe_3$ cluster, a $Al_3$ cluster, or a combination thereof. In still further embodiments, the method further comprises the step, prior to step (b), of contacting the MOF nanoparticle with the agent thereby encapsulating the agent in the nanoparticle. In some embodiments, the method further comprises step (d): adding a salt solution to the oligonucleotide-functionalized MOF nanoparticle, wherein step (d) is after step (c). In some embodiments, the salt solution is added to a final concentration of 0.5 M. In yet further embodiments, the method further comprises step (e): contacting the oligonucleotide-functionalized MOF nanoparticle with one or more nanoparticles, wherein each of the one or more nanoparticles comprises an oligonucleotide that is sufficiently complementary to hybridize to the oligonucleotide on the surface of the oligonucleotide-functionalized MOF nanoparticle, and wherein step (e) is after step (d).

In some aspects a method of inhibiting expression of a gene is provided comprising hybridizing a target polynucleotide encoding the gene with one or more oligonucleotides complementary to all or a portion of the target polynucleotide, the oligonucleotide being the terminal phosphate-modified oligonucleotide of a nanoparticle of the disclosure, wherein hybridizing between the target polynucleotide and the terminal phosphate-modified oligonucleotide occurs over a length of the target polynucleotide with a degree of complementarity sufficient to inhibit expression of the gene product. In some embodiments, expression of the gene product is inhibited in vivo. In some embodiments, expression of the gene product is inhibited in vitro.

In some aspects, the disclosure provides a method for up-regulating activity of a toll-like receptor (TLR) comprising contacting a cell having the TLR with a nanoparticle of the disclosure. In some embodiments, the terminal phosphate-modified oligonucleotide comprises a TLR agonist. In further embodiments, the TLR is chosen from the group consisting of toll-like receptor 1 (TLR1), toll-like receptor 2 (TLR2), toll-like receptor 3 (TLR3), toll-like receptor 4 (TLR4), toll-like receptor 5 (TLR5), toll-like receptor 6 (TLR6), toll-like receptor 7 (TLR7), toll-like receptor 8 (TLR8), toll-like receptor 9 (TLR9), toll-like receptor 10 (TLR10), toll-like receptor 11 (TLR11), toll-like receptor 12 (TLR12), and toll-like receptor 13 (TLR13). In some embodiments, the method is performed in vitro. In some embodiments, the method is performed in vivo.

DETAILED DESCRIPTION

Figure 1:
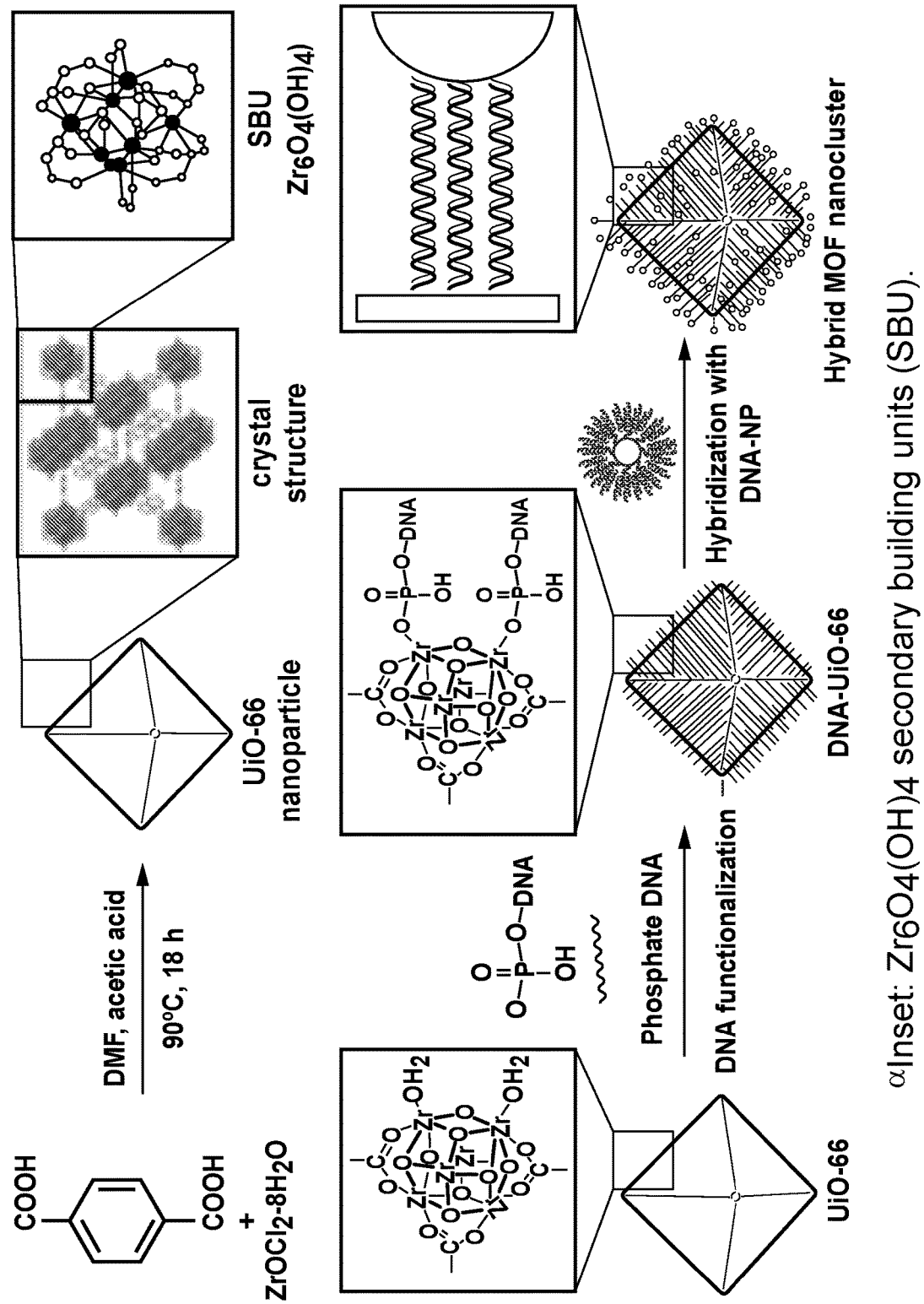
FIG. 1 depicts (a) Schematic representation of solvothermal synthesis of UiO-66 MOF nanoparticles$^a$; (b) DNA modification of MOFs, utilizing terminal phosphate-modified DNA and subsequent sequence-specific assembly of MOF-NP core-satellite hybrid architectures.

Metal-organic frameworks (MOFs) are a class of modular, crystalline, and porous materials that hold promise for storage and transport of chemical cargoes. Though MOFs have been studied in bulk forms, ways of deliberately manipulating the external surface functionality of MOF nanoparticles are less developed. A generalizable approach to modify their surfaces would allow one to impart chemical functionality onto the particle surface that is independent of the bulk MOF structure. Moreover, the use of a chemically programmable ligand, such as an oligonucleotide (e.g., DNA), would allow for the manipulation of interparticle interactions. Herein, a coordination chemistry-based strategy for the surface functionalization of the external metal nodes of MOF nanoparticles with terminal phosphate-modified oligonucleotides is provided. The external surfaces of nine distinct archetypical MOF particles containing four different metal species (Zr, Cr, Fe, and Al) were successfully functionalized with oligonucleotides, illustrating the generality of this strategy. By taking advantage of the programmable and specific interactions of oligonucleotides, 11 distinct MOF particle-inorganic particle core-satellite clusters were synthesized. In these hybrid nanoclusters, the relative stoichiometry, size, shape, and composition of the building blocks can all be independently controlled. The present disclosure provides access to a new set of oligonucleotide-nanoparticle conjugates, which are useful as programmable material building blocks and as probes for measuring and manipulating intracellular processes.

Directly supplementing functional proteins via intracellular delivery remains a challenge due to their inherent instability outside their native environments, their large size, and charged surfaces. The synthesis of oligonucleotide-MOF nanoparticle (MOF NP) conjugates for the effective intracellular delivery of proteins is also provided herein. The straightforward two-step preparation of such delivery vehicles was realized by encapsulating proteins inside the mesoporous channels of two water stable zirconium MOF NPs, NU-1000 and PCN-222/MOF-545, followed by phosphate terminated oligonucleotide surface functionalization. Insulin was chosen as the model protein for this system. High protein loading (approximately 40 wt %) and a 10-fold enhancement of cellular uptake was achieved using this strategy, as compared to that of the native protein itself. The 3D oligonucleotide shell not only stabilized MOF NPs in colloids but also enhanced their cellular internalization with no appreciable cytotoxicity. This approach can be generalized to facilitate the delivery of a variety of proteins as biological probes or potential therapeutics.

Proteins play key roles in many life processes. Intracellular delivery of active proteins is attractive for many potential biomedical applications,[47] including evaluation of metabolic pathways,[48] regulation of cellular processes,[3] and therapeutics for protein deficiency diseases.[50-52] During the past decades, a series of techniques has been developed to facilitate protein internalization by live cells, such as the use of transfection agents, nanocarriers,[53-55] and extensive protein surface modifications.[56-59] Although each strategy has its own merit, many suffer from notable cytotoxicity, reduced protein activity, or low delivery payload, rendering limited chemical stability and delivery efficiency.[60] Recently, MOFs have emerged as a class of promising materials for the immobilization and storage of functional proteins, due to their mesoporous and stable framework structures, which lead to advantageous properties including high protein loading capacity, and significantly improved thermal and chemical stability for efficient enzymatic catalyses.[61-67] Comparatively, the intracellular delivery of proteins with MOF NPs is less explored,[68-70] partially due to their often poor colloidal stability and positively charged surface,[71-72] rendering limited cellular uptake efficiency and unfavorable bioavailability.[73-76] Therefore, the development of an effective approach to reduce MOF NP aggregation, minimize positive charge induced cytotoxicity, and facilitate its intracellular delivery is highly desirable.[77-78]

Figure 26:
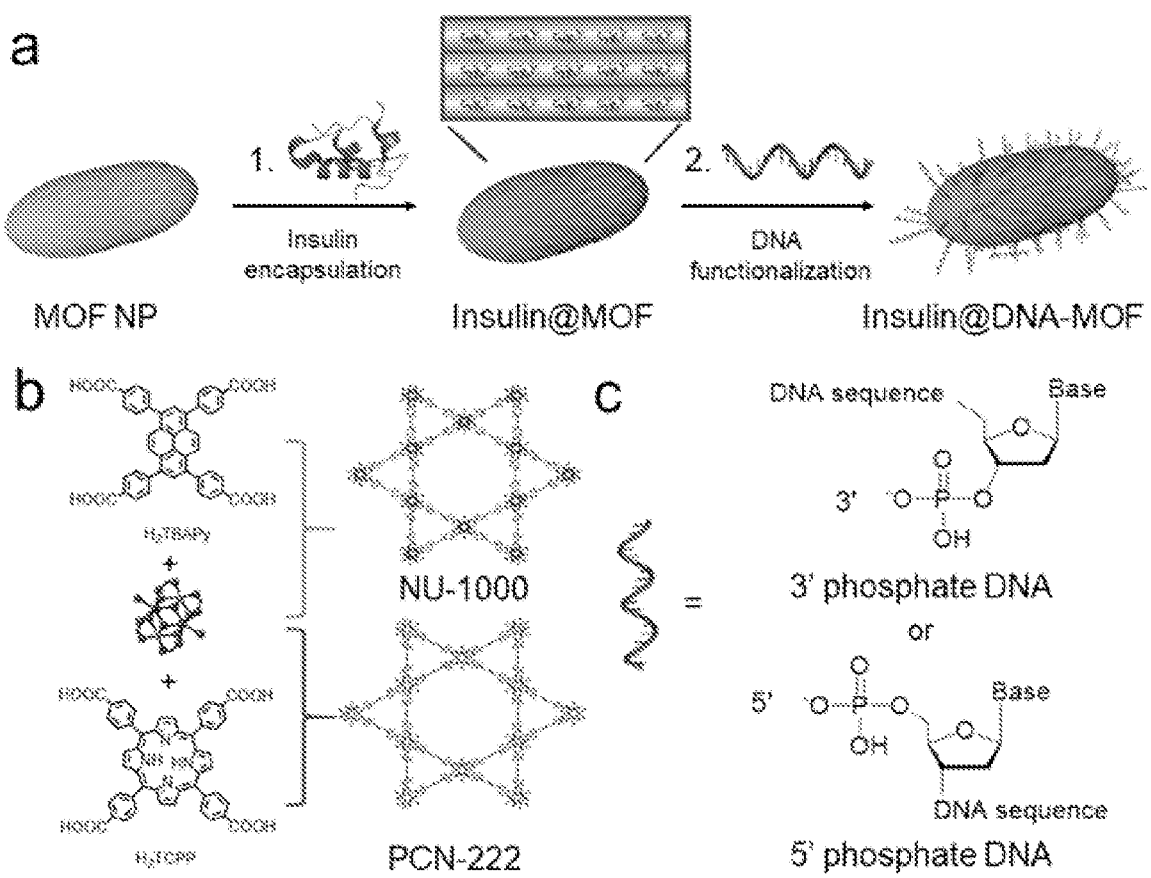
FIG. 26 depicts (a) a schematic illustration of insulin encapsulation in the mesoporous channels of MOF NPs followed by surface functionalization using terminal phosphate-modified DNA. (b) Crystal structures of two mesoporous Zr MOFs: NU-1000 and PCN-222/MOF-545 and their respective organic linkers. (c) Terminal phosphate modified nucleic acid (3' or 5') used.

Spherical nucleic acid (SNA)-NP conjugates,[79] which are synthesized from NPs densely functionalized with a plurality oligonucleotides, exhibit the unique ability to effectively enter cells without the use of cationic or viral transfections.[80] The densely packed oligonucleotides are recognized by cell surface scavenger receptors and facilitate nanoparticle uptake via caveolin-mediated endocytosis.[81-82] Importantly, a variety of SNA-NP conjugates have been synthesized with different core compositions,[59,77,83-85] exhibiting advantageous properties in intracellular diagnostic,[86] gene regulation,[87] and immunomodulatory strategies.[88] Herein, a straightforward strategy to synthesize oligonucleotide-MOF NP conjugates for intracellular delivery of proteins is provided (FIG. 26a).

It is noted here that, as used in this specification and the appended claims, the singular forms "a," "an," and "the" include plural reference unless the context clearly dictates otherwise.

It is also noted that the term "about" as used herein is understood to mean approximately.

Nucleic Acid-Metal Organic Framework (MOF) Nanoparticle Conjugates

Metal-organic frameworks (MOFs) are 1, 2, or 3-dimensional microporous materials containing metals/metal ions coordinated to organic ligands. As used herein, MOFs include infinite coordination polymers (ICPs), including, but not limited to, the ICPs disclosed in US Patent Application Publication No. 2009/0211445, which is incorporated herein by reference in its entirety.

The present disclosure provides a nanoparticle comprising a MOF and a plurality of oligonucleotides attached to a surface of the metal-organic framework. The MOF comprises (1) a metal and (2) a multi-dentate ligand. In some embodiments, the ligand is an organic ligand. The multi-dentate ligands have at least two functional groups that each coordinate to a different metal atom to form the MOF. The MOF can comprise a plurality of the same multi-dentate ligand or a combination/mixture of two or more multi-dentate ligands. The multi-dentate ligand can comprise two or more (e.g., 2, 3, 4) coordinating functional groups such as carboxylate functional groups (COOH or COO$^-$), or heterocyclic groups having at least 1 ring nitrogen (e.g., pyridyl, pyrimidinyl, pyrazinyl, imidazolyl). In some cases, the multi-dentate ligand comprises 2, 3, or 4 carboxylate functional groups. In some cases, the multi-dentate ligand comprises at least 1 carboxylate functional group and at least 1 heterocyclic group—e.g., a pyrazolate, imidazolate, or tetrazolate. Examples of multi-dentate ligands include formic acid, acetic acid, oxalic acid, propanoic acid, butanedioic acid, (E)-butenedioic acid, benzene-1,4-dicarboxylic acid, benzene-1,3-dicarboxylic acid, benzene-1,3,5-tricarboxylic acid, 2-amino-1,4-benzenedicarboxylic acid, 2-bromo-1,4-benzenedicarboxylic acid, biphenyl-4,4'-dicarboxylic acid, biphenyl-3,3',5,5'-tetracarboxylic acid, biphenyl-3,4',5-tricarboxylic acid, 2,5-dihydroxy-1,4-benzenedicarboxylic acid, 1,3,5-tris(4-carboxyphenyl)benzene, (2E,4E)-hexa-2,4-dienedioic acid, 1,4-naphthalenedicarboxylic acid, pyrene-2,7-dicarboxylic acid, 4,5,9,10-tetrahydropyrene-2,7-dicarboxylic acid, aspartic acid, glutamic acid, adenine, 4,4'-bypiridine, pyrimidine, pyrazine, pyridine-4-carboxylic acid, pyridine-3-carboxylic acid, imidazole, 1H-benzimidazole, and 2-methyl-1H-imidazole. In some cases, the multi-dentate ligand comprises terephthalic acid ($H_2BDC$), 2,2'-bipyridine-5,5'-dicarboxylic acid ($H_2BPY$), 2',5'-bis(azidomethyl)-[1,1':4',1''-terphenyl]-4,4''-dicarboxylic acid ($H_2TPDC-N_3$), or 4,4',4'',4'''-porphyrin tetrabenzoic acid ($H_2TCPP$). In some cases, the multi-dentate ligand is terephthalic acid ($H_2BDC$), 2,2'-bipyridine-5,5'-dicarboxylic acid ($H_2BPY$), 2',5'-bis(azidomethyl)-[1,1':4',1''-terphenyl]-4,4''-dicarboxylic acid ($H_2TPDC-N_3$), 4,4',4'',4'''-porphyrin tetrabenzoic acid ($H_2TCPP$), 1,2,4,5-tetrakis(4-carboxyphenyl)benzene, 1,3,5-tris(4'-carboxy[1,1'-biphenyl]-4-yl)benzene, 1,3,5-tris(4-carboxyphenyl)benzene, 2,5-dihydroxyterephthalic acid, 2,6-naphthalenedicarboxylic acid, 2-hydroxyterephthalic acid, 2-methylimidazole, 3,3',5,5'-tetracarboxydiphenylmethane, 4,4',4''-s-triazine-2,4,6-triyl-tribenzoic acid, 9,10-anthracenedicarboxylic acid, biphenyl-3,3',5,5'-tetracarboxylic acid, biphenyl-3,4',5-tricarboxylic acid, imidazole, terephthalic acid (i.e., 1,4-benzenedicarboxylic acid), trimesic acid, [1,1':4',1'' ]terphenyl-3,3',5,5'-tetracarboxylic acid, or combinations thereof.

In various embodiments, the MOF forms a nanoparticle core and the oligonucleotides form a layer attached to an outer surface of the core. In various embodiments, the metal-organic framework has a three-dimensional structure. In various embodiments, the oligonucleotides are attached to the metal-organic framework at a terminus of the oligonucleotide. In various embodiments one terminus of the oligonucleotide is attached to a surface of the metal-organic framework and the other terminus of the oligonucleotide is oriented away from (or distal to) the surface of the metal-organic framework. In various embodiments, a linking group is covalently attached to both the metal-organic framework and the oligonucleotide.

In some embodiments, the metal of the MOF nanoparticle comprises a plurality of metal ions. In some cases, the MOF comprises a plurality of the same metal ion, while in others the MOF comprises a combination/mixture of different metal ions. Contemplated metal ions include zirconium (Zr), chromium (Cr), iron (Fe), aluminum (Al), and mixtures thereof. In some embodiments, the MOF comprises UiO-66, UiO-67-bpy, UiO68-$N_3$/PCN-58, PCN-222/MOF-545, PCN-223, PCN-224, MIL-101 (Al), MIL-101 (Fe), or MIL-101(Cr). Suitable metal ions include, but are not limited to, a 12-connect $Zr_3$ cluster, a 6-connect $Zr_3$ cluster, a 8-connect $Zr_3$ cluster, a $Cr_3$ cluster, a $Fe_3$ cluster, a $Al_3$ cluster, or a combination thereof.

In various aspects, the present disclosure provides a method of inhibiting expression of a gene product encoded by a target oligonucleotide comprising contacting the target oligonucleotide with a nanoparticle as described herein under conditions sufficient to inhibit expression of the gene product. In some embodiments, expression of the gene product is inhibited in vivo. In some embodiments, expression of the gene product is inhibited in vitro. In various embodiments, expression of the gene product is inhibited by at least about 5% relative to expression of the gene product in the absence of contacting the target oligonucleotide with the nanoparticle, for example, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, and/or at least about 95%. In various aspects, the present disclosure also provides a method of detecting a target molecule comprising contacting the target molecule with a nanoparticle as described herein, wherein contact between the target molecule and the nanoparticle results in a detectable change. In some embodiments, the detecting is in vitro. In some embodiments, the detecting is in vivo.

Oligonucleotides

Oligonucleotides contemplated by the present disclosure include DNA, RNA, modified forms and combinations thereof as defined herein. Accordingly, oligonucleotide comprises DNA. In some embodiments, the DNA is double stranded, and in further embodiments the DNA is single stranded. In further aspects, the oligonucleotide comprises RNA, and in still further aspects, the oligonucleotide comprises double stranded RNA, and in a specific embodiment, the double stranded RNA is a small interfering RNA (siRNA). The term "RNA" includes duplexes of two separate strands, as well as single stranded structures. Single stranded RNA also includes RNA with secondary structure. In some aspects, RNA having a hairpin loop in contemplated.

The oligonucleotides used in the MOFs disclosed herein are terminal phosphate-modified oligonucleotides, such that the phosphate forms a metal-phosphate bond with the metal ion of the MOF nanoparticle. In some embodiments, the terminal phosphate-modified oligonucleotide has a phosphate group on its 3' end. In some embodiments, the terminal phosphate-modified oligonucleotide has a phosphate group on its 5' end.

In some embodiments, the terminal phosphate-modified oligonucleotide comprises a $(GGT)_n$ nucleotide sequence, wherein n is 2-20. In further embodiments, n is or is at least 2, is or is at least 3, is or is at least 4, is or is at least 5, is or is at least 6, is or is at least 7, is or is at least 8, is or is at least 9, is or is at least 10, is or is at least 11, is or is at least 12, is or is at least 13, is or is at least 14, is or is at least 15, is or is at least 16, is or is at least 17, is or is at least 18, is or is at least 19, or is 20. In further embodiments, n is less than 3, less than 4, less than 5, less than 6, less than 7, less than 8, less than 9, less than 10, less than 11, less than 12, less than 13, less than 14, less than 15, less than 16, less than 17, less than 18, less than 19, or is less than 20.

In some aspects, the oligonucleotide is comprised of a sequence that is sufficiently complementary to a target sequence of an oligonucleotide such that hybridization of the oligonucleotide that is part of the MOF and the target oligonucleotide takes place. The oligonucleotide in various aspects is single stranded or double stranded, as long as the double stranded molecule also includes a single strand sequence that hybridizes to a single strand sequence of the target oligonucleotide. In some aspects, hybridization of the oligonucleotide that is part of the MOF can form a triplex structure with a double-stranded target oligonucleotide. In another aspect, a triplex structure can be formed by hybridization of a double-stranded oligonucleotide that is part of the MOF to a single-stranded target oligonucleotide. Further description of triplex oligonucleotide complexes is found in PCT/US2006/40124, which is incorporated herein by reference in its entirety.

A "oligonucleotide" is understood in the art to comprise individually polymerized nucleotide subunits. The term "nucleotide" or its plural as used herein is interchangeable with modified forms as discussed herein and otherwise known in the art. In certain instances, the art uses the term "nucleobase" which embraces naturally-occurring nucleotide, and non-naturally-occurring nucleotides which include modified nucleotides. Thus, nucleotide or nucleobase means the naturally occurring nucleobases adenine (A), guanine (G), cytosine (C), thymine (T) and uracil (U). Non-naturally occurring nucleobases include, for example and without limitations, xanthine, diaminopurine, 8-oxo-N6-methyladenine, 7-deazaxanthine, 7-deazaguanine, N4,N4-ethanocytosin, N',N'-ethano-2,6-diaminopurine, 5-methylcytosine (mC), 5-(C3-C6)-alkynyl-cytosine, 5-fluorouracil, 5-bromouracil, pseudoisocytosine, 2-hydroxy-5-methyl-4-triazolopyridine, isocytosine, isoguanine, inosine and the "non-naturally occurring" nucleobases described in Benner et al., U.S. Pat. No. 5,432,272 and Susan M. Freier and Karl-Heinz Altmann, 1997, Nucleic Acids Research, vol. 25: pp 4429-4443. The term "nucleobase" also includes not only the known purine and pyrimidine heterocycles, but also heterocyclic analogues and tautomers thereof. Further naturally and non-naturally occurring nucleobases include those disclosed in U.S. Pat. No. 3,687,808 (Merigan, et al.), in Chapter 15 by Sanghvi, in Antisense Research and Application, Ed. S. T. Crooke and B. Lebleu, CRC Press, 1993, in Englisch et al., 1991, Angewandte Chemie, International Edition, 30: 613-722 (see especially pages 622 and 623, and in the Concise Encyclopedia of Polymer Science and Engineering, J. I. Kroschwitz Ed., John Wiley & Sons, 1990, pages 858-859, Cook, Anti-Cancer Drug Design 1991, 6, 585-607, each of which are hereby incorporated by reference in their entirety). In various aspects, oligonucleotides also include one or more "nucleosidic bases" or "base units" which are a category of non-naturally-occurring nucleotides that include compounds such as heterocyclic compounds that can serve like nucleobases, including certain "universal bases" that are not nucleosidic bases in the most classical sense but serve as nucleosidic bases. Universal bases include 3-nitropyrrole, optionally substituted indoles (e.g., 5-nitroindole), and optionally substituted hypoxanthine. Other desirable universal bases include, pyrrole, diazole or triazole derivatives, including those universal bases known in the art.

Modified nucleotides are described in EP 1 072 679 and WO 97/12896, the disclosures of which are incorporated herein by reference. Modified nucleotides include without limitation, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F- adenine, 2-amino-adenine, 8-azaguanine and 8-azaadenine, 7-deazaguanine and 7-deazaadenine and 3-deazaguanine and 3-deazaadenine. Further modified bases include tricyclic pyrimidines such as phenoxazine cytidine (1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzox-azin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified bases may also include those in which the purine or pyrimidine base is replaced with other heterocycles, for example, 7-deaza-adenine, 7-deazaguanosine, 2-aminopyridine and 2-pyridone. Additional nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., 1991, Angewandte Chemie, International Edition, 30: 613, and those disclosed by Sanghvi, Y. S., Chapter 15, Antisense Research and Applications, pages 289-302, Crooke, S. T. and Lebleu, B., ed., CRC Press, 1993. Certain of these bases are useful for increasing the binding affinity and include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are, in certain aspects combined with 2'-O-methoxyethyl sugar modifications. See, U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; 5,750,692 and 5,681,941, the disclosures of which are incorporated herein by reference.

Methods of making oligonucleotides of a predetermined sequence are well-known. See, e.g., Sambrook et al., Molecular Cloning: A Laboratory Manual (2nd ed. 1989) and F. Eckstein (ed.) Oligonucleotides and Analogues, 1st Ed. (Oxford University Press, New York, 1991). Solid-phase synthesis methods are preferred for both polyribonucleotides and polydeoxyribonucleotides (the well-known methods of synthesizing DNA are also useful for synthesizing RNA). Polyribonucleotides can also be prepared enzymatically. Non-naturally occurring nucleobases can be incorporated into the oligonucleotide, as well. See, e.g., U.S. Pat. No. 7,223,833; Katz, J. Am. Chem. Soc., 74:2238 (1951); Yamane, et al., J. Am. Chem. Soc., 83:2599 (1961); Kosturko, et al., Biochemistry, 13:3949 (1974); Thomas, J. Am. Chem. Soc., 76:6032 (1954); Zhang, et al., J. Am. Chem. Soc., 127:74-75 (2005); and Zimmermann, et al., J. Am. Chem. Soc., 124:13684-13685 (2002).

The MOFs disclosed herein generally comprise oligonucleotides from about 5 nucleotides to about 100 nucleotides in length. More specifically, MOFs disclosed herein comprise oligonucleotides that are about 5 to about 90 nucleotides in length, about 5 to about 80 nucleotides in length, about 5 to about 70 nucleotides in length, about 5 to about 60 nucleotides in length, about 5 to about 50 nucleotides in length, about 5 to about 45 nucleotides in length, about 5 to about 40 nucleotides in length, about 5 to about 35 nucleotides in length, about 5 to about 30 nucleotides in length, about 5 to about 25 nucleotides in length, about 5 to about 20 nucleotides in length, about 5 to about 15 nucleotides in length, about 5 to about 10 nucleotides in length, and all oligonucleotides intermediate in length of the sizes specifically disclosed to the extent that the oligonucleotide is able to achieve the desired result. Accordingly, oligonucleotides of 5, 6, 7, 8, 9, 10, 11, 12, 13, 14, 15, 16, 17, 18, 19, 20, 21, 22, 23,24,25,26,27,28,29, 30, 31, 32, 33, 34,35, 36, 37, 38, 39,40,41,42,43,44,45,46,47, 48,49,50,51,52,53,54, 55,56,57,58,59,60, 61, 62, 63, 64, 65, 66,67,68, 69,70,71,72, 73,74,75,76,77,78,79,80,81,82,83,84,85,86,87,88,89, 90, 91,92,93, 94, 95, 96, 97, 98, 99, 100 or more nucleotides in length are contemplated.

Oligonucleotides, as defined herein, also includes aptamers. The production and use of aptamers is known to those of ordinary skill in the art. In general, aptamers are nucleic acid or peptide binding species capable of tightly binding to and discreetly distinguishing target ligands (Yan et al., RNA Biol. 6(3) 316-320 (2009), incorporated by reference herein in its entirety). Aptamers, in some embodiments, may be obtained by a technique called the systematic evolution of ligands by exponential enrichment (SELEX) process (Tuerk et al., Science 249:505-10 (1990), U.S. Pat. Nos. 5,270,163, and 5,637,459, each of which is incorporated herein by reference in their entirety). General discussions of nucleic acid aptamers are found in, for example and without limitation, Nucleic Acid and Peptide Aptamers: Methods and Protocols (Edited by Mayer, Humana Press, 2009) and Crawford et al., Briefings in Functional Genomics and Proteomics 2(1): 72-79 (2003). Additional discussion of aptamers, including but not limited to selection of RNA aptamers, selection of DNA aptamers, selection of aptamers capable of covalently linking to a target protein, use of modified aptamer libraries, and the use of aptamers as a diagnostic agent and a therapeutic agent is provided in Kopylov et al., Molecular Biology 34(6): 940-954 (2000) translated from Molekulyarnaya Biologiya, Vol. 34, No. 6, 2000, pp. 1097-1113, which is incorporated herein by reference in its entirety. In various aspects, an aptamer is between 10-100 nucleotides in length.

In various aspects, the methods include use of an oligonucleotide which is 100% complementary to the target oligonucleotide, i.e., a perfect match, while in other aspects, the oligonucleotide is at least (meaning greater than or equal to) about 95% complementary to the target oligonucleotide over the length of the oligonucleotide, at least about 90%, at least about 85%, at least about 80%, at least about 75%, at least about 70%, at least about 65%, at least about 60%, at least about 55%, at least about 50%, at least about 45%, at least about 40%, at least about 35%, at least about 30%, at least about 25%, at least about 20% complementary to the target oligonucleotide over the length of the oligonucleotide to the extent that the oligonucleotide is able to achieve the desired of inhibition of a target gene product. It will be understood by those of skill in the art that the degree of hybridization is less significant than a resulting detection of the target oligonucleotide, or a degree of inhibition of gene product expression.

Oligonucleotide Density

MOFs as provided herein have a density of the oligonucleotide on the surface of the MOF. In some aspects, the resistance of the oligonucleotide to degradation and/or the uptake of MOFs by a cell is influenced by the density of oligonucleotides associated with the MOF surface. As described in PCT/US2008/65366, incorporated herein by reference in its entirety, a higher density of oligonucleotides on the surface of an oligonucleotide functionalized nanoparticle is associated with an increased uptake of nanoparticles by a cell.

A surface density adequate to make the MOF stable and the conditions necessary to obtain it for a desired combination of MOF and oligonucleotides can be determined empirically. Broadly, the smaller the oligonucleotide that is used, the higher the surface density of that oligonucleotide can be. Generally, a surface density of at least 1 pmol/cm$^2$ will be adequate to provide stable MOF compositions. In some aspects, the surface density is at least 10 pmol/cm$^2$. Methods are also provided wherein the oligonucleotide is present in a MOF at a surface density of at least 2 pmol/cm$^2$, at least 3 pmol/cm$^2$, at least 4 pmol/cm$^2$, at least 5 pmol/cm$^2$, at least 6 pmol/cm$^2$, at least 7 pmol/cm$^2$, at least 8 pmol/cm$^2$, at least 9 pmol/cm$^2$, at least 10 pmol/cm$^2$, at least about 15 pmol/cm$^2$, at least about 20 pmol/cm$^2$, at least about 25 pmol/cm$^2$, at least about 30 pmol/cm$^2$, at least about 35 pmol/cm$^2$, at least about 40 pmol/cm$^2$, at least about 45 pmol/cm$^2$, at least about 50 pmol/cm$^2$, at least about 55 pmol/cm$^2$, at least about 60 pmol/cm$^2$, at least about 65 pmol/cm$^2$, at least about 70 pmol/cm$^2$, at least about 75 pmol/cm$^2$, at least about 80 pmol/cm$^2$, at least about 85 pmol/cm$^2$, at least about 90 pmol/cm$^2$, at least about 95 pmol/cm$^2$, at least about 100 pmol/cm$^2$, at least about 125 pmol/cm$^2$, at least about 150 pmol/cm$^2$, at least about 175 pmol/cm$^2$, at least about 200 pmol/cm$^2$, at least about 250 pmol/cm$^2$, at least about 300 pmol/cm$^2$, at least about 350 pmol/cm$^2$, at least about 400 pmol/cm$^2$, at least about 450 pmol/cm$^2$, at least about 500 pmol/cm$^2$, at least about 550 pmol/cm$^2$, at least about 600 pmol/cm$^2$, at least about 650 pmol/cm$^2$, at least about 700 pmol/cm$^2$, at least about 750 pmol/cm$^2$, at least about 800 pmol/cm$^2$, at least about 850 pmol/cm$^2$, at least about 900 pmol/cm$^2$, at least about 950 pmol/cm$^2$, at least about 1000 pmol/cm$^2$ or more. Methods are also provided wherein the oligonucleotide is present in a MOF at a surface density of less than 2 pmol/cm$^2$, less than 3 pmol/cm$^2$, less than 4 pmol/cm$^2$, less than 5 pmol/cm$^2$, less than 6 pmol/cm$^2$, less than 7 pmol/cm$^2$, less than 8 pmol/cm$^2$, less than 9 pmol/cm$^2$, less than 10 pmol/cm$^2$, less than about 15 pmol/cm$^2$, less than about 20 pmol/cm$^2$, less than about 25 pmol/cm$^2$, less than about 30 pmol/cm$^2$, less than about 35 pmol/cm$^2$, less than about 40 pmol/cm$^2$, less than about 45 pmol/cm$^2$, less than about 50 pmol/cm$^2$, less than about 55 pmol/cm$^2$, less than about 60 pmol/cm$^2$, less than about 65 pmol/cm$^2$, less than about 70 pmol/cm$^2$, less than about 75 pmol/cm$^2$, less than about 80 pmol/cm$^2$, less than about 85 pmol/cm$^2$, less than about 90 pmol/cm$^2$, less than about 95 pmol/cm$^2$, less than about 100 pmol/cm$^2$, less than about 125 pmol/cm$^2$, less than about 150 pmol/cm$^2$, less than about 175 pmol/cm$^2$, less than about 200 pmol/cm$^2$, less than about 250 pmol/cm$^2$, less than about 300 pmol/cm$^2$, less than about 350 pmol/cm$^2$, less than about 400 pmol/cm$^2$, less than about 450 pmol/cm$^2$, less than about 500 pmol/cm$^2$, less than about 550 pmol/cm$^2$, less than about 600 pmol/cm$^2$, less than about 650 pmol/cm$^2$, less than about 700 pmol/cm$^2$, less than about 750 pmol/cm$^2$, less than about 800 pmol/cm$^2$, less than about 850 pmol/cm$^2$, less than about 900 pmol/cm$^2$, less than about 950 pmol/cm$^2$, or less than about 1000 pmol/cm$^2$.

It is contemplated that the density of oligonucleotides in a MOF modulates specific biomolecule and/or non-biomolecule interactions with the oligonucleotide on the surface and/or with the MOF itself. Under various conditions, some polypeptides may be prohibited from interacting with oligonucleotides that are part of a MOF based on steric hindrance caused by the density of oligonucleotides. In aspects where interaction of oligonucleotides with a biomolecule and/or non-biomolecule that are otherwise precluded by steric hindrance is desirable, the density of oligonucleotides in the MOF is decreased to allow the biomolecule and/or non-biomolecule to interact with the oligonucleotide.

It is also contemplated that oligonucleotide surface density modulates the stability of the oligonucleotide associated with the MOF. Thus, in one embodiment, a MOF comprising an oligonucleotide is provided wherein the oligonucleotide has a half-life that is at least substantially the same as the half-life of an identical oligonucleotide that is not part of a MOF. In other embodiments, the oligonucleotide associated with the MOF has a half-life that is about 5% greater to about 1,000,000-fold greater or more than the half-life of an identical oligonucleotide that is not part of a MOF.

Methods of Detecting a Target Oligonucleotide

The disclosure provides methods of detecting a target molecule comprising contacting the target molecule with a composition as described herein. The contacting results, in various aspects, in regulation of gene expression as provided by the disclosure. In another aspect, the contacting results in a detectable change, wherein the detectable change indicates the detection of the target molecule. Detection of the detectable label is performed by any of the methods described herein, and the detectable label can be on a molecule that is part of a MOF, or can be on the target molecule.

Methods of Inhibiting Gene Expression

Additional methods provided by the disclosure include methods of inhibiting expression of a gene product expressed from a target oligonucleotide comprising contacting the target oligonucleotide with a composition as described herein, wherein the contacting is sufficient to inhibit expression of the gene product. Inhibition of the gene product results from the hybridization of a target oligonucleotide with a composition of the disclosure.

It is understood in the art that the sequence of an oligonucleotide that is part of a MOF need not be 100% complementary to that of its target oligonucleotide in order to specifically hybridize to the target oligonucleotide. Moreover, an oligonucleotide that is part of a MOF may hybridize to a target oligonucleotide over one or more segments such that intervening or adjacent segments are not involved in the hybridization event (for example and without limitation, a loop structure or hairpin structure). The percent complementarity is determined over the length of the oligonucleotide that is part of the MOF. For example, given a MOF comprising an oligonucleotide in which 18 of 20 nucleotides of the oligonucleotide are complementary to a 20 nucleotide region in a target oligonucleotide of 100 nucleotides total length, the oligonucleotide that is part of the MOF would be 90 percent complementary. In this example, the remaining noncomplementary nucleotides may be clustered or interspersed with complementary nucleotides and need not be contiguous to each other or to complementary nucleotides. Percent complementarity of an oligonucleotide that is part of a MOF with a region of a target oligonucleotide can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7, 649-656).

Methods for inhibiting gene product expression include those wherein expression of the target gene product is inhibited by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or 100% compared to gene product expression in the absence of a MOF comprising an oligonucleotide. In other words, methods provided embrace those which result in essentially any degree of inhibition of expression of a target gene product.

The degree of inhibition is determined in vivo from a body fluid sample or from a biopsy sample or by imaging techniques well known in the art. Alternatively, the degree of inhibition is determined in vitro in a cell culture assay, generally as a predictable measure of a degree of inhibition that can be expected in vivo resulting from use of a composition as described herein. It is contemplated by the disclosure that the inhibition of a target oligonucleotide is used to assess the effects of the inhibition on a given cell. By way of non-limiting examples, one can study the effect of the inhibition of a gene product wherein the gene product is part of a signal transduction pathway. Alternatively, one can study the inhibition of a gene product wherein the gene product is hypothesized to be involved in an apoptotic pathway.

It will be understood that any of the methods described herein can be used in combination to achieve a desired result. For example and without limitation, methods described herein can be combined to allow one to both detect a target oligonucleotide as well as regulate its expression. In some embodiments, this combination can be used to quantitate the inhibition of target oligonucleotide expression over time either in vitro or in vivo. The quantitation over time is achieved, in one aspect, by removing cells from a culture at specified time points and assessing the relative level of expression of a target oligonucleotide at each time point. A decrease in the amount of target oligonucleotide as assessed, in one aspect, through visualization of a detectable label, over time indicates the rate of inhibition of the target oligonucleotide.

Thus, determining the effectiveness of a given oligonucleotide to hybridize to and inhibit the expression of a target oligonucleotide, as well as determining the effect of inhibition of a given oligonucleotide on a cell, are aspects that are contemplated.

Agents

In some aspects, the disclosure contemplates an oligonucleotide-functionalized MOF nanoparticle further comprising an agent. In various embodiments, the agent is a peptide, a protein, a nanoparticle (for example and without limitation, a noble metal, a metal oxide, or a quantum dot) an antibody, a small molecule, or a combination thereof. In any of the embodiments of the disclosure, the agent is encapsulated in the nanoparticle. Methods of encapsulating an agent in a nanoparticle are generally known in the art[94-95] and are described herein (see, e.g., Example 2).

An "agent" as used herein means any compound useful for therapeutic or diagnostic purposes. The term as used herein is understood to include any compound that is administered to a patient for the treatment or diagnosis of a condition.

Protein therapeutic agents include, without limitation peptides, enzymes, structural proteins, receptors and other cellular or circulating proteins as well as fragments and derivatives thereof, the aberrant expression of which gives rise to one or more disorders. Therapeutic agents also include, as one specific embodiment, chemotherapeutic agents. Therapeutic agents also include, in various embodiments, a radioactive material.

In various aspects, protein therapeutic agents include cytokines or hematopoietic factors including without limitation IL-1 alpha, IL-1 beta, IL-2, IL-3, IL-4, IL-5, IL-6, IL-11, colony stimulating factor-1 (CSF-1), M-CSF, SCF, GM-CSF, granulocyte colony stimulating factor (G-CSF), interferon-alpha (IFN-alpha), consensus interferon, IFN-beta, IFN-gamma, IL-7, IL-8, IL-9, IL-10, IL-12, IL-13, IL-14, IL-15, IL-16, IL-17, IL-18, erythropoietin (EPO), thrombopoietin (TPO), angiopoietins, for example Ang-1, Ang-2, Ang-4, Ang-Y, the human angiopoietin-like polypeptide, vascular endothelial growth factor (VEGF), angiogenin, bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, bone morphogenic protein receptor IA, bone morphogenic protein receptor IB, brain derived neurotrophic factor, ciliary neurotrophic factor, ciliary neutrophic factor receptor, cytokine-induced neutrophil chemotactic factor 1, cytokine-induced neutrophil, chemotactic factor 2a, cytokine-induced neutrophil chemotactic factor 2, p endothelial cell growth factor, endothelin 1, epidermal growth factor, epithelial-derived neutrophil attractant, fibroblast growth factor 4, fibroblast growth factor 5, fibroblast growth factor 6, fibroblast growth factor 7, fibroblast growth factor 8, fibroblast growth factor 8b, fibroblast growth factor 8c, fibroblast growth factor 9, fibroblast growth factor 10, fibroblast growth factor acidic, fibroblast growth factor basic, glial cell line-derived neutrophic factor receptor α1, glial cell line-derived neutrophic factor receptor α2, growth related protein, growth related protein a, growth related protein p, growth related protein y, heparin binding epidermal growth factor, hepatocyte growth factor, hepatocyte growth factor receptor, insulin-like growth factor I, insulin-like growth factor receptor, insulin-like growth factor II, insulin-like growth factor binding protein, keratinocyte growth factor, leukemia inhibitory factor, leukemia inhibitory factor receptor α, nerve growth factor nerve growth factor receptor, neurotrophin-3, neurotrophin-4, placenta growth factor, placenta growth factor 2, platelet-derived endothelial cell growth factor, platelet derived growth factor, platelet derived growth factor A chain, platelet derived growth factor AA, platelet derived growth factor AB, platelet derived growth factor B chain, platelet derived growth factor BB, platelet derived growth factor receptor α, platelet derived growth factor receptor β, pre-B cell growth stimulating factor, stem cell factor receptor, TNF, including TNF0, TNF1, TNF2, transforming growth factor α, transforming growth factor β, transforming growth factor β1, transforming growth factor β1.2, transforming growth factor β2, transforming growth factor β3, transforming growth factor β5, latent transforming growth factor β1, transforming growth factor β binding protein I, transforming growth factor β binding protein II, transforming growth factor β binding protein III, tumor necrosis factor receptor type I, tumor necrosis factor receptor type II, urokinase-type plasminogen activator receptor, vascular endothelial growth factor, and chimeric proteins and biologically or immunologically active fragments thereof. Examples of biologic agents include, but are not limited to, immuno-modulating proteins such as cytokines, monoclonal antibodies against tumor antigens, tumor suppressor genes, and cancer vaccines. Examples of interleukins that may be used in conjunction with the compositions and methods of the present invention include, but are not limited to, interleukin 2 (IL-2), and interleukin 4 (IL-4), interleukin 12 (IL-12). Other immuno-modulating agents other than cytokines include, but are not limited to bacillus Calmette-Guerin, levamisole, and octreotide.

In various embodiments, therapeutic agents described in U.S. Pat. No. 7,667,004 (incorporated by reference herein in its entirety) are contemplated for use in the compositions and methods disclosed herein and include, but are not limited to, alkylating agents, antibiotic agents, antimetabolic agents, hormonal agents, plant-derived agents, and biologic agents.

Examples of alkylating agents include, but are not limited to, bischloroethylamines (nitrogen mustards, e.g. chlorambucil, cyclophosphamide, ifosfamide, mechlorethamine, melphalan, uracil mustard), aziridines (e.g. thiotepa), alkyl alkone sulfonates (e.g. busulfan), nitrosoureas (e.g. carmustine, lomustine, streptozocin), nonclassic alkylating agents (altretamine, dacarbazine, and procarbazine), platinum compounds (e.g., carboplastin, cisplatin and platinum (IV) (Pt (IV))).

Examples of antibiotic agents include, but are not limited to, anthracyclines (e.g. doxorubicin, daunorubicin, epirubicin, idarubicin and anthracenedione), mitomycin C, bleomycin, dactinomycin, plicatomycin. Additional antibiotic agents are discussed in detail below.

Examples of antimetabolic agents include, but are not limited to, fluorouracil (5-FU), floxuridine (5-FUdR), methotrexate, leucovorin, hydroxyurea, thioguanine (6-TG), mercaptopurine (6-MP), cytarabine, pentostatin, fludarabine phosphate, cladribine (2-CDA), asparaginase, imatinib mesylate (or GLEEVEC®), and gemcitabine.

Examples of hormonal agents include, but are not limited to, synthetic estrogens (e.g. diethylstibestrol), antiestrogens (e.g. tamoxifen, toremifene, fluoxymesterol and raloxifene), antiandrogens (bicalutamide, nilutamide, flutamide), aromatase inhibitors (e.g., aminoglutethimide, anastrozole and tetrazole), ketoconazole, goserelin acetate, leuprolide, megestrol acetate and mifepristone.

Examples of plant-derived agents include, but are not limited to, vinca alkaloids (e.g., vincristine, vinblastine, vindesine, vinzolidine and vinorelbine), podophyllotoxins (e.g., etoposide (VP-16) and teniposide (VM-26)), camptothecin compounds (e.g., 20(S) camptothecin, topotecan, rubitecan, and irinotecan), taxanes (e.g., paclitaxel and docetaxel).

Chemotherapeutic agents contemplated for use include, without limitation, alkylating agents including: nitrogen mustards, such as mechlor-ethamine, cyclophosphamide, ifosfamide, melphalan and chlorambucil; nitrosoureas, such as carmustine (BCNU), lomustine (CCNU), and semustine (methyl-CCNU); ethylenimines/methylmelamine such as thriethylenemelamine (TEM), triethylene, thiophosphoramide (thiotepa), hexamethylmelamine (HMM, altretamine); alkyl sulfonates such as busulfan; triazines such as dacarbazine (DTIC); antimetabolites including folic acid analogs such as methotrexate and trimetrexate, pyrimidine analogs such as 5-fluorouracil, fluorodeoxyuridine, gemcitabine, cytosine arabinoside (AraC, cytarabine), 5-azacytidine, 2,2'-difluorodeoxycytidine, purine analogs such as 6-mercaptopurine, 6-thioguanine, azathioprine, 2'-deoxycoformycin (pentostatin), erythrohydroxynonyladenine (EHNA), fludarabine phosphate, and 2-chlorodeoxyadenosine (cladribine, 2-CdA); natural products including antimitotic drugs such as paclitaxel, vinca alkaloids including vinblastine (VLB), vincristine, and vinorelbine, taxotere, estramustine, and estramustine phosphate; epipodophylotoxins such as etoposide and teniposide; antibiotics such as actimomycin D, daunomycin (rubidomycin), doxorubicin, mitoxantrone, idarubicin, bleomycins, plicamycin (mithramycin), mitomycinC, and actinomycin; enzymes such as L-asparaginase; biological response modifiers such as interferon-alpha, IL-2, G-CSF and GM-CSF; miscellaneous agents including platinum coordination complexes such as cisplatin, Pt(IV) and carboplatin, anthracenediones such as mitoxantrone, substituted urea such as hydroxyurea, methylhydrazine derivatives including N-methylhydrazine (MIH) and procarbazine, adrenocortical suppressants such as mitotane (o,p'-DDD) and aminoglutethimide; hormones and antagonists including adrenocorticosteroid antagonists such as prednisone and equivalents, dexamethasone and aminoglutethimide; progestin such as hydroxyprogesterone caproate, medroxyprogesterone acetate and megestrol acetate; estrogen such as diethylstilbestrol and ethinyl estradiol equivalents; antiestrogen such as tamoxifen; androgens including testosterone propionate and fluoxymesterone/ equivalents; antiandrogens such as flutamide, gonadotropin-releasing hormone analogs and leuprolide; and non-steroidal antiandrogens such as flutamide.

Chemotherapeutics also include, but are not limited to, an anti-PD-1 antibody, alkylating agents, angiogenesis inhibitors, antibodies, antimetabolites, antimitotics, antiproliferatives, antivirals, aurora kinase inhibitors, apoptosis promoters (for example, Bcl-2 family inhibitors), activators of death receptor pathway, Bcr-Abl kinase inhibitors, BiTE (Bi-Specific T cell Engager) antibodies, antibody drug conjugates, biologic response modifiers, Bruton's tyrosine kinase (BTK) inhibitors, cyclin-dependent kinase inhibitors, cell cycle inhibitors, cyclooxygenase-2 inhibitors, DVDs, leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPs), intercalating antibiotics, kinase inhibitors, kinesin inhibitors, Jak2 inhibitors, mammalian target of rapamycin inhibitors, microRNAs, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics (e.g., cisplatin), polo-like kinase (Plk) inhibitors, phosphoinositide-3 kinase (PI3K) inhibitors, proteasome inhibitors, purine analogs, pyrimidine analogs, receptor tyrosine kinase inhibitors, retinoids/deltoids plant alkaloids, topoisomerase inhibitors, ubiquitin ligase inhibitors, and the like, as well as combinations of one or more of these agents. Additional chemotherapeutics are disclosed in U.S. Patent Application Publication No. 2018/0072810, incorporated by reference herein in its entirety.

In some embodiments, agents include small molecules. The term "small molecule," as used herein, refers to a chemical compound, for instance a peptidometic that may optionally be derivatized, or any other low molecular weight organic compound, either natural or synthetic. Such small molecules may be a therapeutically deliverable substance or may be further derivatized to facilitate delivery.

By "low molecular weight" is meant compounds having a molecular weight of less than 1000 Daltons, typically between 300 and 700 Daltons. Low molecular weight compounds, in various aspects, are about 100, about 150, about 200, about 250, about 300, about 350, about 400, about 450, about 500, about 550, about 600, about 650, about 700, about 750, about 800, about 850, about 900, or about 1000 Daltons.

Immune Regulation

Toll-like receptors (TLRs) are a class of proteins, expressed in sentinel cells, that plays a key role in regulation of innate immune system. The mammalian immune system uses two general strategies to combat infectious diseases. Pathogen exposure rapidly triggers an innate immune response that is characterized by the production of immunostimulatory cytokines, chemokines and polyreactive IgM antibodies. The innate immune system is activated by exposure to Pathogen Associated Molecular Patterns (PAMPs) that are expressed by a diverse group of infectious microorganisms. The recognition of PAMPs is mediated by members of the Toll-like family of receptors. TLR receptors, such as TLR 4, TLR 8 and TLR 9 that response to specific oligonucleotide are located inside special intracellular compartments, called endosomes. The mechanism of modulation of TLR 4, TLR 8 and TLR9 receptors is based on DNA-protein interactions.

Synthetic immunostimulatory oligonucleotides that contain CpG motifs that are similar to those found in bacterial DNA stimulate a similar response of the TLR receptors. Therefore immunomodulatory oligonucleotides have various potential therapeutic uses, including treatment of immune deficiency and cancer.

Down regulation of the immune system would involve knocking down the gene responsible for the expression of the Toll-like receptor. This antisense approach involves use of a metal-organic framework (MOF) nanoparticle functionalized with specific antisense oligonucleotide sequences to knock out the expression of any toll-like protein.

Accordingly, in some embodiments, methods of utilizing a MOF nanoparticle of the disclosure for modulating toll-like receptors are disclosed. The method either up-regulates or down-regulates the Toll-like-receptor through the use of a TLR agonist or a TLR antagonist, respectively. The toll-like receptors modulated include toll-like receptor 1, toll-like receptor 2, toll-like receptor 3, toll-like receptor 4, toll-like receptor 5, toll-like receptor 6, toll-like receptor 7, toll-like receptor 8, toll-like receptor 9, toll-like receptor 10, toll-like receptor 11, toll-like receptor 12, and toll-like receptor 13. In some embodiments, the method comprises contacting a cell having a toll-like receptor with oligonucleotide-functionalized MOF nanoparticle, wherein the terminal-phosphate-modified oligonucleotide comprises a TLR agonist. In further embodiments, the TLR is chosen from the group consisting of toll-like receptor 1 (TLR1), toll-like receptor 2 (TLR2), toll-like receptor 3 (TLR3), toll-like receptor 4 (TLR4), toll-like receptor 5 (TLR5), toll-like receptor 6 (TLR6), toll-like receptor 7 (TLR7), toll-like receptor 8 (TLR8), toll-like receptor 9 (TLR9), toll-like receptor 10 (TLR10), toll-like receptor 11 (TLR11), toll-like receptor 12 (TLR12), and toll-like receptor 13 (TLR13). In various embodiments, the TLR is modulated in vitro. In some embodiments, the TLR is modulated in vivo.

EXAMPLES

MOF nanoparticles are synthesized and solvent exchanged with DMF (3 times) and water (3 times) to remove excess metal ions and organic ligands. The crystallinity and crystallite size of MOF nanoparticle are determined by powder x-ray diffraction (PXRD) and transmission electron microscopy respectively (TEM). Next, phosphate modified nucleic acids are synthesized on a DNA synthesizer employing chemically modified phosphoramidites at either the 3' or 5' ends of the oligonucleotides. All oligonucleotides are deprotected under conditions recommended by the manufacturer and purified by reverse phase high performance liquid chromatography (HPLC). Characterization and determination of concentrations are determined by matrix assisted laser desorption ionization (MALDI-TOF) mass spectrometry and UV-Vis spectroscopy, respectively. Excess phosphate terminated nucleic acid (approximately 100 nmol) was added to MOF NP colloids (approximately 2 pmol), and then left on a shaker to incubate overnight. Then, a salt-aging procedure, slow addition of 2 M sodium chloride solution to the reaction mixture to reach a final concentration of 0.5 M, is used to screen the negatively charged oligomers and achieve a high density of surface-immobilized oligonucleotides. Excess oligonucleotides were removed by centrifugation (5×5000 rpm, 10 min), followed by resuspension of the DNA-MOF nanoparticle conjugates in water. The DNA surface coverage on MOF nanoparticle is determined by inductively coupled plasma atomic emission spectroscopy (ICP-AES) and UV-visible spectroscopy (UV-vis). First, the surface area of MOF nanoparticle can be calculated based on geometric approximation and radius/edge length obtained from TEM. Second, the number of metal atoms per particle can be calculated for a given size MOF based on crystallographic information. Finally, the molar concentration of MOF nanoparticle sample is obtained by ICP-AES analysis of the metal contents of MOF sample.

Example 1

Materials

All reagents unless otherwise stated were obtained from commercial sources and were used without further purification. All oligonucleotides used in this work were synthesized on a solid-support MM12 synthesizer with reagents purchased from Glen Research. The water used in all experiments was ultrapure deionized (DI) grade (18.2 M-cm resistivity), obtained from a Milli-Q Biocel system (Millipore, Billerica, Mass., USA).

Methods

Synthesis and Characterization of MOF Nanoparticle

Synthesis of 9 MOF Nanoparticles

UiO-66. UiO-66 was synthesized via solvothermal reaction conditions. 1,4-benzenedicarboxylic acid (50 mg, 0.30 mmol) was dissolved in 1 mL of N,N-dimethylformamide (DMF). In a separate vial, zirconyl chloride octahydrate (21 mg, 0.066 mmol) was dissolved in 3 mL of DMF. The two solutions were mixed together in a 10 mL scintillation vial, and 2.0 mL acetic acid was added to the reaction mixture. After brief sonication, the solution was heated at 90° C. for 18 hours to yield UiO-66 nanoparticles.

UiO-67-bpy. UiO-67-bpy was synthesized via a similar method. Biphenyl-4,4'-dicarboxylic acid (150 mg, 0.6 mmol) was added to 20 mL of DMF, resulting in a white suspension. In a separate vial, zirconyl chloride octahydrate (105 mg, 0.33 mmol) was dissolved in 3 mL of DMF. The two fractions were mixed together in a 25 mL scintillation vial, and 2.5 mL acetic acid was added to the reaction mixture. After brief sonication, the suspension was heated at 90° C. for 18 hours to yield UiO-67-bpy.

UiO-68-azide/PCN-58. 2',5'-bis(azidomethyl)-[1,1':4',1''-terphenyl]-4,4''-dicarboxylic acid (TPDC-2CH2N3) was synthesized according to a literature reported method.[33] In a 10 mL scintillation vial, TPDC-2CH2N3 (100 mg, 0.075 mmol) was added to 1 mL of DMF. In a separate vial, zirconyl chloride octahydrate (21 mg, 0.066 mmol) was dissolved in 3 mL of DMF. The two fractions were mixed together in a 10 mL scintillation vial, and 240 µL acetic acid was added to the reaction mixture. The suspension was heated at 90° C. for 18 hours.

PCN-222/MOF-545. The synthesis of PCN-222/MOF-545 nanocrystal was based on a literature reported method with minor modifications.[34] Zirconyl chloride octahydrate (37.5 mg, 0.116 mmol) and tetrakis(4-carboxyphenyl)-porphyrin (6.5 mg, 0.0082 mmol) were dissolved in DMF (16.25 mL) in a 22 mL borosilicate vial with a Teflon-lined cap. Dichloroacetic acid (0.25 mL, 3.0 mmol) was added, and the resulting solution was heated at 130° C. for 18 hours to afford dark purple rod-shaped nanocrystals and a yellow mother liquor. The nanocrystals were collected by centrifugation (15000 rpm, 5 minutes), followed by solvent exchange with DMF.

PCN-223. The synthesis of PCN-223 nanocrystals was based on a literature reported method with minor modifications.[34] In a 10 mL scintillation vial, 5,10, 15, 20-Tetrakis (4-carboxyphenyl)porphyrin ($H_2$TCPP, 5.2 mg, 0.007 mmol), zirconyl chloride octahydrate (9.8 mg, 0.03 mmol), and acetic acid (0.4 mL) in 3 mL of DMF were ultrasonically dissolved and heated at 90° C. for 18 hours. After the reaction was complete, PCN-223 nanoparticles were collected by centrifugation, followed by washing with fresh DMF for 3 times.

PCN-224. The synthesis of PCN-224 nanocrystal was based on a literature-reported method with minor modifications.[35] In a 25 mL scintillation vial, 5,10, 15, 20-Tetrakis (4-carboxyphenyl) porphyrin (10 mg, 0.013 mmol), zirconyl chloride octahydrate (30 mg, 0.093 mmol), and benzoic acid (300 mg, 2.4 mmol) in 10 mL of DMF were dissolved and the mixture was stirred (300 rpm) at 90° C. (oil bath) for 5 hours. After the reaction was done, PCN-224 nanoparticles were collected by centrifugation (12000 rpm, 30 min), followed by washing with fresh DMF for 3 times.

MIL-101-Cr. The synthesis of MIL-101-Cr nanocrystals was based on a literature reported method with minor modifications.[36] Terephthalic acid ($H_2$BDC, 55 mg 0.33 mmol) and chromium nitrate nonahydrate ($Cr(NO_3)_3 \cdot 9H_2$, 132 mg, 0.33 mmol) were dissolved in 10 mL of water. The resulting suspension was stirred for 1 hour at room temperature then heated under autogenous pressure at 180° C. for 8 hours in a Teflon-lined autoclave. After cooling to room temperature, the mixture was filtered to remove the recrystallized terephthalic acid. The product was isolated from the filtrate as a green powder following centrifugation at 7000 rpm for 15 minutes, and then washed three times with ethanol.

MIL-101-Fe. MIL-101 (Fe) $Fe_3O(H_2O)_2Cl(BDC)_3$ nanoparticles were synthesized using a previously reported microwave heating method.[37] Specifically, 57.5 mg (0.346 mmol) of terephthalic acid and 93.5 mg (0.346 mmol) of $FeCl_3 \cdot H_2O$ were dissolved in 15 mL of DMF. The solution was placed in a HP500 microwave vessel, and sealed. The reaction was then rapidly heated to 150° C. (within 30 seconds), and was held at this temperature for 10 minutes. After cooling to room temperature, the particles were isolated by centrifuging, and were washed with DMF and ethanol. After cooling to room temperature, the nanoparticles were isolated by centrifugation and washed with DMF to remove the excess reactants.

MIL-101-Al. For the synthesis of MIL-101 (Al) nanocrystals, 45 mg (0.27 mmol) of terephthalic acid were dissolved in 5 mL of DMF. In a separate vial, 120 mg (0.5 mmol) of $AlCl_3 \cdot 6H_2O$ was added to 5 mL of DMF, to which 5 mL of terephthalic acid DMF solution was added. After brief sonication, the suspension was left at room temperature overnight to fully dissolve. 500 µL of acetic acid was added to the solution and then heated at 110° C. in a conventional oven for 18 hours. After cooling to room temperature, the particles were isolated by centrifugation and washed with DMF and ethanol to remove the excess reactants.

Powder X-Ray Diffraction

The crystallinity of the synthesized MOF nanoparticles and DNA functionalized MOF nanoparticles conjugates were confirmed by powder X-ray diffraction (PXRD). Powder X-ray diffraction patterns were collected on Rigaku Smartlab instrument (Tokyo, Japan) with a 2θ=0.05° scan rate over 2.5-30° range at 45 kV and 160 mA.

Transmission Electron Microscopy and Scanning Electron Microscopy

MOF nanoparticles were analyzed using a Hitachi HD-2300 scanning transmission electron microscope in either SE or TE modes with an accelerating voltage of 200 kV. Samples were dispersed onto TEM grids by drop-casting a dilute solution containing MOF crystals or MOF-DNA conjugates directly onto TEM grids. The average crystal size for each synthesis was determined by measuring the edge length of more than 100 crystals from multiple syntheses under analogous synthetic conditions.

Synthesis of Oligonucleotides

Oligonucleotides were synthesized using a Mermaid MM12 DNA synthesizer (Bio Automation) on a standard CPG solid phase support. All oligonucleotides were deprotected under conditions recommended by the manufacturer and purified by reverse phase high performance liquid chromatography (HPLC). Characterization and determination of concentrations were determined by matrix assisted laser desorption ionization (MALDI-TOF) mass spectrometry and UV-Vis spectroscopy, respectively. A complete list of oligonucleotides synthesized can be found in Table 1.

TABLE 1

DNA sequences used in this study.

| # | Sequence Name | Sequence |
|---|---|---|
| | | Thiolated Strands |
| 1 | AuNP-bound assembly strand | 5'-HS-(Spacer)$_2$-TTGTTAATATGAGTCGTT-3' |
| 2 | AgNP-bound assembly strand | 5'-(DS)$_3$-(Spacer)$_2$-TTGTTAATATGAGTCGTT-3' |
| 3 | AuNP-melt strand | 5'-AAGGAA-A-TTCTTAAATATTCGTCTT-3' |
| | | Terminal Phosphate Strands |
| 4 | MOF-bound strand | 5'-Phosphate-(Spacer)$_2$-AACGACTCATATTAACAA-3' |
| 5 | MOF-bound complementary strand | 5'-Phosphate-(Spacer)$_2$-TTGTTAATATGAGTCGTT-3' |
| 6 | MOF-dye loading strand | 5'-Phosphate-(Spacer)$_2$-AACGACTCATATTAACAA-Tamra-3' |
| 7 | MOF-dye loading strand #2 | 5'-Phosphate-(Spacer)$_2$-AACGACTCATATTAACAA-Cy5-3' |
| 8 | MOF-CPR-T | 5'-Phosphate-T-3' |
| 9 | MOF-CPR-T2 | 5'-Phosphate-TT-3' |
| 10 | MOF-CPR-T20 | 5-Phosphate-TTTTTTTTTTTTTTTTTTTT-3 |
| 11 | MOF-melt strand | 5'-TTCCTT-A-TTGTTAATATGAGTCGTT-3' |
| | | Strained alkyne strands |
| 12 | AzideNP-bound assembly strand | 5'-DBCO-TEG-(Spacer)$_2$-TTGTTAATATGAGTCGTT-3' |

All modified phosphoramidites are manufactured by Glen Research.
1. "Spacer" refers to the 18-O-Dimethoxytritylhexaethyleneglycol, 1-[(2-cyanoethyl)-(N,N-diisopropyl)]-phosphoramidite (Spacer phosphoramidite 18).
2. "DS" refers to the 3-Dimethoxytrityloxy-2-(3-((R)-α-ipoamido)propanamido)propyl-1-O-(2-cyanoethyl)-(N,N-diisopropyl)-phosphoramidite (Dithiol serinol phosphoramidite).
3. "HS" refers to the 1-O-Dimethoxytrityl-hexyl-disulfide, 1'-[(2-cyanoethyl)-(N,N-diisopropyl)]-phosphoramidite (Thiol-modifier C6 S—S).
4. "5' Phosphate" refers to [3-(4,4'-Dimethoxytrityloxy)-2,2-dicarboxyethyl]propyl-(2-cyanoethyl)-(N,N-diisopropyl)-phosphoramidite (Chemical phosphorylation reagent II).
5. "3' Phosphate" refers to 3-(4,4'-Dimethoxytrityloxy)-2,2-(dicarboxymethylamido)propyl-1-O-succinoyl-long chain alkylamino-CPG (3'-CPR II CPG)
6. "Tamra" refers to 1-Dimethoxytrityloxy-3-[O—(N-carboxy-(Tetramethyl-rhodamine)-3-aminopropyl)]-propyl-2-O-succinoyl-ong chain alkylamino-CPG (3'-Tamra CPG).
7. "DBCO-TEG" refers to 10-(6-oxo-6-(dibenzo[b,f]azacyclooct-4-yn-1-yl)-capramido-N-ethyl)-O-triethyleneglycol-1-[(2-cyanoethyl)-(N,N-diisopropyl)]-phosphoramidite (5'-DBCO-TEG phosphoramidite).

DNA Functionalization of Nanoparticles

DNA functionalization of MOF nanoparticles. In a typical DNA functionalization experiment, excess phosphate terminated nucleic acid (approximately 100 nmol) was added to MOF NP colloids (approximately 2 pmol), and then left on a shaker to incubate overnight (as described herein). Then, sodium chloride was slowly added to the solution to a final concentration of 0.5 M, which reduces electrostatic repulsion between negatively charged neighboring oligonucleotide strands, allowing one to achieve high surface densities of DNA. Excess oligonucleotides were removed by centrifugation (5×5000 rpm, 10 minutes), followed by resuspension of the DNA-nanoMOF conjugates in water.

DNA functionalization of silver and gold nanoparticles. Citrate-capped spherical gold and silver nanoparticles (Ted Pella) were used as received with no further modification. Anisotropic gold nanoparticles were synthesized according to procedures that are detailed extensively elsewhere.[38,39]

DNA-functionalization of AuNPs with thiol-modified oligonucleotides was carried out according to procedures that are detailed extensively elsewhere.[40] Briefly, 100 nmol of the AuNP-bound assembly strand (Sequence 1) were treated with a solution of 100 mM dithiothreitol (DTT, pH=8) for approximately 1 hour and subsequently purified using Nap-5 size exclusion columns (GE Healthcare) to remove remaining DTT. The surfactant Tween-20 was added to the solution of AuNPs to bring the final surfactant concentration to 0.01 vol %, followed by the addition of the purified thiolated DNA (approximately 4-5 nmol per O.D. of AuNPs). A 5M solution of sodium chloride (NaCl) was slowly added to the nanoparticle solution over the next several hours in a "salt aging" process to increase the density of DNA on the particle surface by shielding against electrostatic repulsion between strands. After bringing the final salt concentration to 0.5 M NaCl, the particles were allowed to sit overnight, followed by purification by three rounds of centrifugation (4000-15000 rpm; times varied from 10-60 minutes depending on the nanoparticle size), removal of supernatant, and resuspension of the nanoparticle pellet in Nanopure water (18.2 MΩ, Millipore) to remove any unreacted DNA, salt, and surfactant. After removal of the supernatant following the final round of centrifugation, salt was added to the purified particles to bring the final concentration once more to 0.2 M NaCl, which is the salt concentration at which all the subsequent assembly reactions took place.

DNA functionalization of iron oxide nanoparticles. DNA-functionalization of iron oxide and cadmium selenide nanoparticles via click chemistry was carried out according to procedures that are detailed elsewhere.[41] Briefly, hydrophobic nanoparticles were first phase transferred to the aqueous phase by surface modification with a layer of amphiphilic polymer coating. In a typical polymer coating process, the solution of azide functionalized poly-maleic anhydride-alt-1-octadecene (N$_3$-PMAO) in chloroform at an initial concentration of polymer monomer units equal to 0.2 M was added into a solution of nanocrystals dissolved in chloroform, at a concentration of approximately 0.1 μM. The ratio of polymer monomer units per nm$^2$ of nanocrystal surface needed to be at least approximately 100 to achieve full coverage of the particles. Then the mixture was heated to approximately 50° C. for 2 minutes with gentle shaking. After cooling to room temperature, the solvent was slowly evaporated by rotary evaporation, resulting in a thin film at the bottom of the flask. Sodium borate buffer (75 mM, pH=9) was added to transfer the nanoparticles into aqueous solution. To remove excess $N_3$-PMAO, sucrose gradient centrifugation was applied. The purified nanoparticles were then functionalized with excess purified DBCO-DNA (#12, azideNP-bound assembly strand). A 5M solution of sodium chloride (NaCl) was slowly added to the nanoparticle solution over the next several hours in a "salt aging" process to increase the density of DNA on the particle surface by shielding against electrostatic repulsion between strands.

Dye loading experiments. In a 5 mL screw vial, Cy5-DNA (sequence 7) functionalized UiO-66 NP was immersed in 50 mM fluoroscein solution (1 mL), and it was kept standing at 25° C. for 24 h. The crystal was collected by centrifugation (10,000 rpm, 40° C., 5 min) and then washed by water, and this cycle was repeated 10 times.

Figure 15:
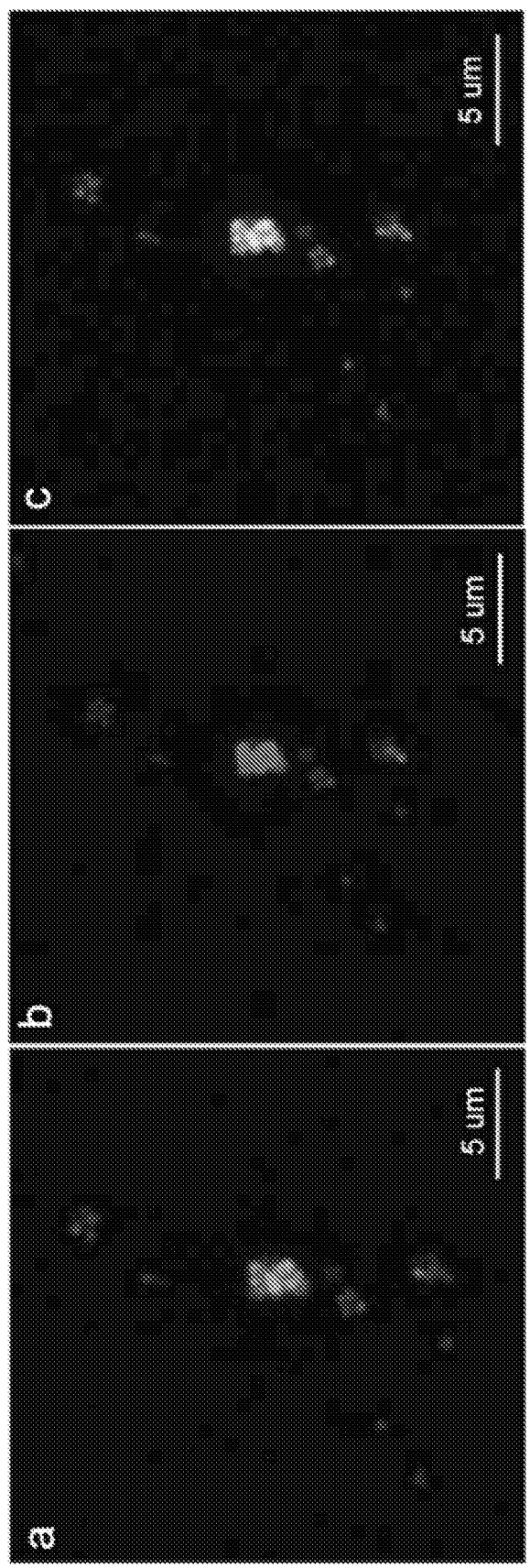
FIG. 15 shows confocal microscopy images of fluorescein encapsulated Cy5-DNA-UiO-66 (a) Cy5 channel, (b) fluorescein channel, (c) merged image.

Confocal fluorescence microscopy. Confocal fluorescence microscopy was performed on a Nikon A1R+ confocal laser microscope system to verify that the external surface of MOF nanoparticles could be functionalized with Cy5-labeled DNA and subsequently encapsulated with fluorescein. Due to the small size of the nanoparticles, photo-bleaching significantly limits the intensity of laser excitation that can be used. Consequently, the cross-sectional image exhibits low brightness. However, one can still clearly see the colocalization of Cy5 and fluorescein (FIG. 15), suggesting that the internal pores of the MOF nanoparticles are still accessible post-DNA functionalization.

Quantification of DNA Surface Coverage

UV-Vis spectroscopy (UV-Vis). UV-Vis spectroscopy was performed on a Cary 5000 (Agilent) UV-Vis spectrometer fitted with a temperature stage. One centimeter (cm) quartz optical cells were utilized to make measurements. The surface coverages of DNA on the MOF nanoparticle-DNA conjugates were determined by UV-Vis, utilizing a dye labeled DNA sequence #6.

Inductively Coupled Plasma-Atomic Emission Spectroscopy (ICP-AES). The DNA coverage of each MOF was quantified based on the nanoparticle surface area and NP molar concentration. With the radius/edge length of each MOF NP obtained from TEM, the surface area of each nanoparticle was calculated based on geometric approximations: octahedron for UiO-66, UiO-67-bpy, UiO-68-N3, and MIL-101(Fe); sphere for PCN-224, MIL-101(Cr) and MIL-101(Al); rod for PCN-222; ellipsoid for PCN-223). The molar concentration of each MOF NP sample was obtained by ICP-AES analysis of the metal contents of these MOF samples in addition to crystallographic information, based on which the number of metal atoms per particle can be calculated for a given size MOF NP. ICP-AES analysis was carried out on a Thermo iCap 7600 ICP-OES instrument with an automated sample changer. MOF samples were dispersed in DMF (1 mL), and 10 µl of the MOF sample was added to HNO3 (990 µl). The samples were heated at 60° C. for 15 h to fully digest the MOF. Unknown samples were prepared with an internal multi-element standard and compared to a standard curve generated.

$^{31}P\{^1H\}$ magic angle spinning solid state nuclear magnetic resonance spectroscopy. $^{31}P\{^1H\}$ Magic Angle Spinning (MAS) NMR spectroscopy was performed on a Varian 400 MHz VNMRS system (512 scans, 5 s recycle time, and 10,000 Hz spin rate) to directly investigate the bonding between the phosphate moiety of DNA and metal clusters.

Characterization of MOF-NP Core-Satellite Nanoclusters

Silica encapsulation of MOF-NP core-satellite nanoclusters. Immobilization of MOF-NP core-satellite nanoclusters from colloidal solution to the solid-state was achieved by silica encapsulation.[42] Briefly, N-trimethoxysilylpropyl-N,N,N-trimethylammonium chloride (TMSPA) (2 µL, 7.2 pmol) was added in large excess (relative to the number of DNA phosphate backbone) to the nanoclusters in 1 mL 0.2 M NaCl solution and the mixture was allowed to stir for approximately 30 minutes before the addition of triethoxysilane (TEOS) (4 µL, 21.7 µmol). The suspension was vigorously stirred for 20 minutes at room temperature, followed by purification to remove excess silica by three rounds of centrifugation and resuspension in water. For TEM, the silica-encapsulated nanoclusters were resuspended in water and drop-cast onto a TEM grid.

Figure 13:
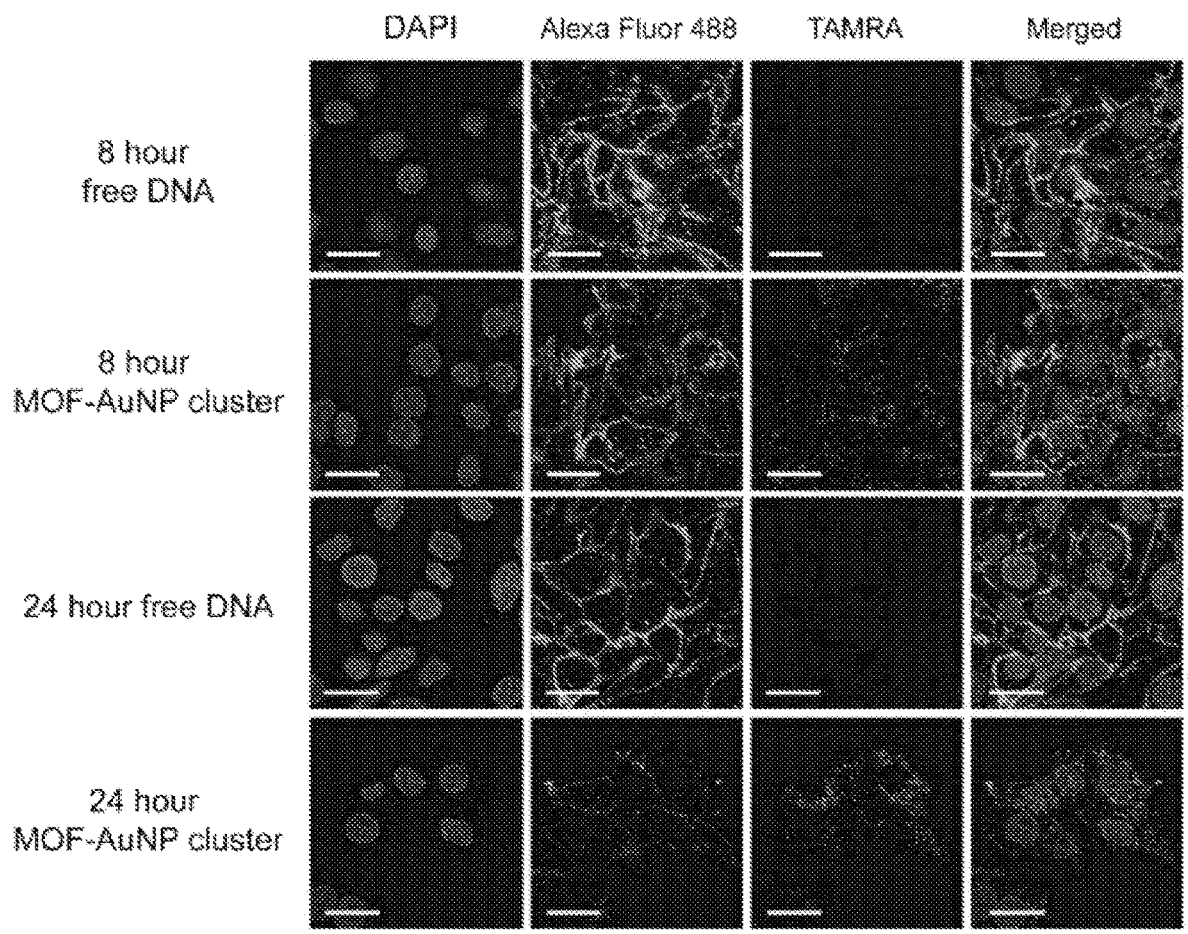
FIG. 13 shows that MOF-NP nanoclusters show enhanced cellular uptake capability as compared to that of single strand DNA. Fluorescence micrograph of SK-OV-3 cells incubated with different forms of nucleic acid: (1) hybridized nanoclusters synthesized with 225 nm UiO-66 (labeled with Tamra-DNA) and 20 nm AuNP, and (2) dye labeled single strand DNA at a total DNA concentration of 1×10$^{-6}$ M for 8 hours and 24 hours, respectively. Scale bars=10 μm.

Cell Culture, Cell Uptake, and Cell Cytotoxicity Studies of MOF-AuNP Nanoclusters Cell culture and uptake experiments. The cellular cytotoxicity and uptake properties of MOF-NP hybrid nanocluster were assessed. Specifically, Tamra phosphoramidite labeled DNA was synthesized and functionalized on 225 nm UiO-66 nanocrystals as a fluorescent label, which was then hybridized with 20 nm AuNP to form Tamra-MOF-AuNP nanoclusters. Human ovarian cancer cells (SK-OV-3) in a McCoy's 5A medium were incubated with different forms of nucleic acids: first, 100 µL of a suspension of MOF-AuNP nanocluster; second, 100 µL of equivalent amount of dye labeled free Tamra-DNA strand. Cell filamentous actin (F-actin) were stained with Alexa Fluor 488 Phalloidin, and all non-absorbed particles were removed from cells by washing with HEPES buffer solution. The enrichment of MOF-AuNP nanocluster in cellular vesicles over time was demonstrated by confocal laser scanning microscopy (FIG. 13), where strong accumulation of the nanocluster in cellular vesicle was observed as compared to an equivalent amount of single strand dye-labeled DNA.

MTT assay. Cell viability of SK-OV-3 cells after incubation with different amounts of MOF-AuNP nanoclusters for 24 hours was evaluated by MTT assay as well as a cell viability test, which showed that negligible cytotoxicity or anti-proliferative effects on the cells. Briefly, SK-OV-3 cells were seeded in a 96-well cell culture plate in McCoy's 5A medium at a density of $5 \times 10^4$ cells/mL with 10% fetal bovine serum (FBS) and 5% $CO_2$ at 37° C. for 24 hours. Afterwards, the culture medium was replaced by 200 µL of McCoy's 5A medium containing the carbon dots at different doses and cultured for another 8 hours or 24 hours. Then, 10 µL of 5 mg/mL MTT solution was added to each cell well. The cells were further incubated for 4 hours, followed by removal of the culture medium with MTT, and then 100 µL of DMSO was added. The resulting mixture was shaken for 15 min at room temperature. The absorbance of MTT at 492 nm was measured on an automatic ELISA analyzer (SPR-960). Each experiment was conducted by 5 times and the average data were presented.

Results/Discussion

Figure 2:
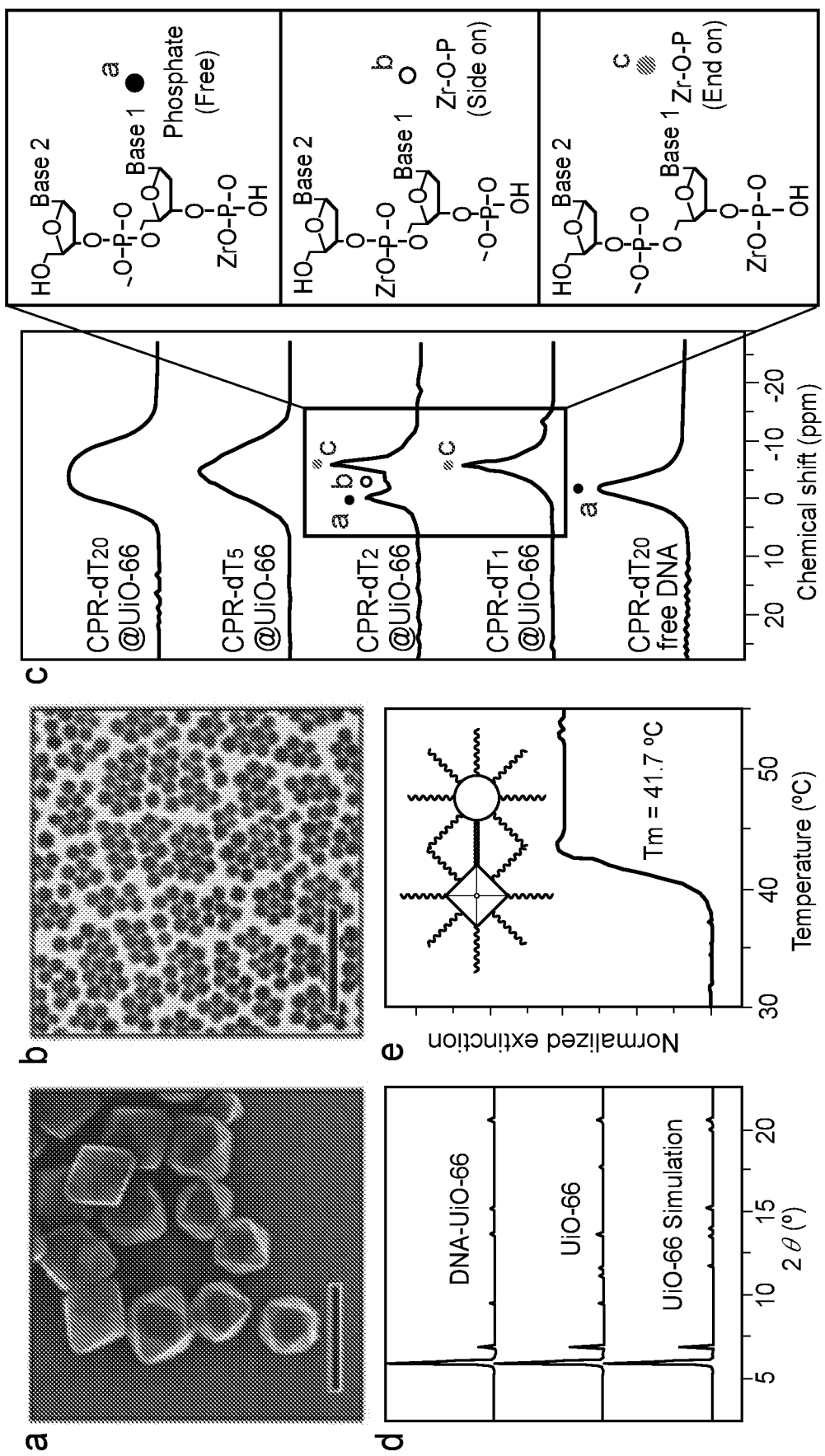
FIG. 2 depicts the characterization of DNA functionalized MOF nanoparticles: (a) SEM of UiO-66 and (b) TEM images of DNA functionalized UiO66. (c) 31P{1H} SSNMR spectra of phosphate functionalized oligonucleotide. Inset: three phosphorus resonances corresponding to unbound phosphodiester (blue), side on Zr bound phosphodiester (gray) and Zr bound terminal phosphate (red). (d) PXRD of simulated UiO-66 (black), 225 nm UiO-66 before (red) and after (blue) DNA functionalization. (e) Melting transition of MOF and 50 nm gold nanoparticle aggregates assembled with complementary DNA. Scale bar=500 nm in panel a and 2 μm in panel b.

For the initial study, UiO-66 was chosen due to its high stability and extensively characterized structure.[22] UiO-66 was synthesized under solvothermal conditions, using acetic acid to modulate crystallite size, resulting in 225±35 nm (edge length) octahedral nanoparticles. The crystallinity and crystallite size of UiO-66 were determined by PXRD and scanning electron microscopy (SEM), respectively (FIG. 2a,d). Next, phosphate-modified nucleic acids were synthesized on a DNA synthesizer employing chemically modified phosphoramidites at either the 3' or 5' ends of the oligonucleotide. In a typical DNA-MOF particle functionalization experiment, excess oligonucleotide was added to a colloidal suspension of MOF nanoparticles, and subsequently incubated overnight (as described herein). A salt-aging procedure was used to screen the negatively charged oligomers and achieve a high density of surface-immobilized oligonucleotides. Transmission electron microscopy (TEM) images and PXRD verified the shapes and crystallinity of the particles were preserved post-DNA modification (FIG. 2b,d).

To confirm the immobilization of nucleic acids on the MOF nanoparticle surface, the interaction between terminal phosphate-functionalized DNA and Zr-based SBUs was probed using $^{31}P\{^1H\}$ magic angle spinning (MAS) solid-state NMR spectroscopy (FIG. 2c). Oligo-T sequences, synthesized with a chemical phosphorylation reagent (CPR), with lengths of one base ("CPR-$T_1$"), two bases ("CPR-$T_2$"), and 20 bases ("CPR-$T_{20}$") were synthesized and chemically adsorbed onto MOF nanoparticles. As shown in FIG. 2c, narrow phosphorus resonances centered at −0.3 ppm correspond to unbound phosphate in the free nucleic acid samples. In the CPR-$T_1$@UiO66 case, Zr-phosphate bond formation was verified by a 4.8 ppm upfield shift in the phosphorus resonance from −0.3 to −5.1 ppm.[23] In the CPR-$T_2$@UiO-66 case, three resonances were observed and assigned to the P atom of the unbound phosphodiester (−0.2 ppm), the Zr—O—P (phosphodiester, −2.8 ppm), and Zr—O—P (terminal phosphate) resonance at −5.9 ppm (FIG. 2c inset). The data suggested immobilization can occur two ways: end on and/or side on where both phosphates can bond with the Zr-rich surface. The significant peak intensity difference between two Zr—O—P modes (terminal phosphate versus phosphodiester) is due to the increased affinity of the terminal phosphate for the Zr centers as compared to that of the internal phosphodiester; this difference is primarily due to the increased steric hindrance felt by the internal phosphodiester and is in agreement with previous reports studying Zr-phosphate interactions, but not in the context of MOFs.[24] For CPRdT$_{20}$@ UiO-66, significant chemical shift broadening upon surface functionalization is observed. This change was attributed to the increased ratio of backbone to terminal phosphates, a distinct chemical environment for each backbone phosphate, and the greater degrees of freedom accessible for the longer oligonucleotide strand. Together, these data supported the conclusion the terminal phosphate moiety of DNA coordinates to the previously solvent-bound Zr sites on the external surface of the MOF nanoparticles.

The extent of DNA coverage on the MOF surface was determined by inductively coupled plasma atomic emission spectroscopy (ICP-AES) and UV-visible spectroscopy (UV-vis). The surface area and Zr atoms per particle for UiO-66 were calculated based on a geometric approximation of the crystallite size, shape, and structure (as described herein). To quantify the DNA surface coverage, Tamra dye-labeled DNA was used to modify UiO-66 particles. The absorption of Tamra at 556 nm was measured to determine that the average DNA loading on UiO-66 was 17±6 pmol/cm$^2$, which correlates with the phosphorus and Zr concentrations measured by ICP-AES (as described herein). The DNA surface coverage realized in this study is about two times higher than a report using a ligand strut modification approach.[15] The high DNA surface coverage was also confirmed by a thermal melting analysis of aggregates formed from DNA-functionalized UiO-66 nanoparticles and gold NPs (diameter=50 nm) with complementary DNA, a property that is characteristic of particles with high DNA surface coverages.[1]

Figure 3:
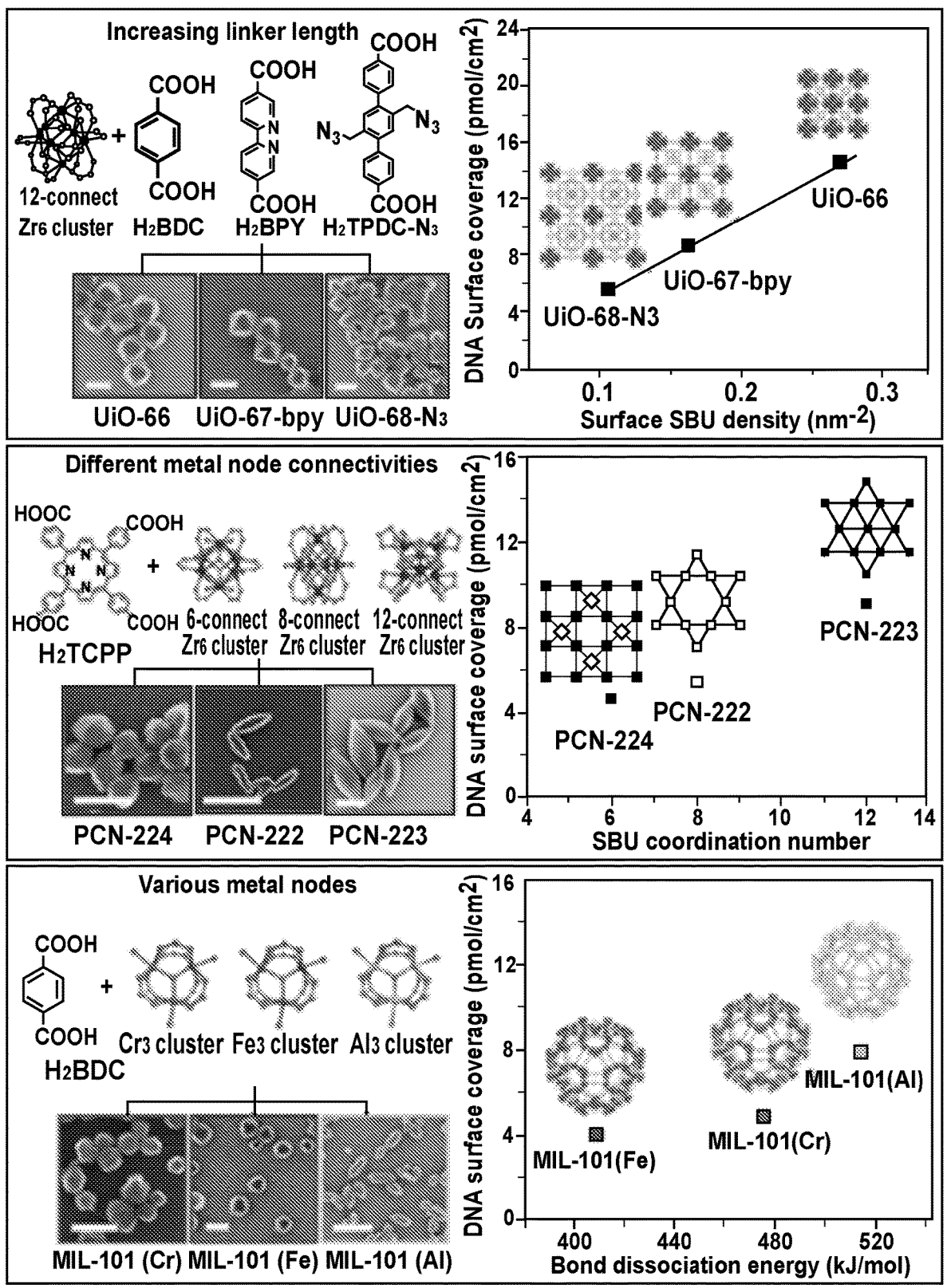
FIG. 3 shows the library of nine MOFs synthesized and further functionalized with DNA. To systematically investigate factors affecting DNA surface coverage, (a) organic linker length, (b) metal node connectivity, and (c) type of metal cluster were independently and deliberately varied and DNA surface coverage was plotted against surface SBU density, SBU coordination number, and M-O bond dissociation energy. Scale bar=200 nm.
Figure 4:
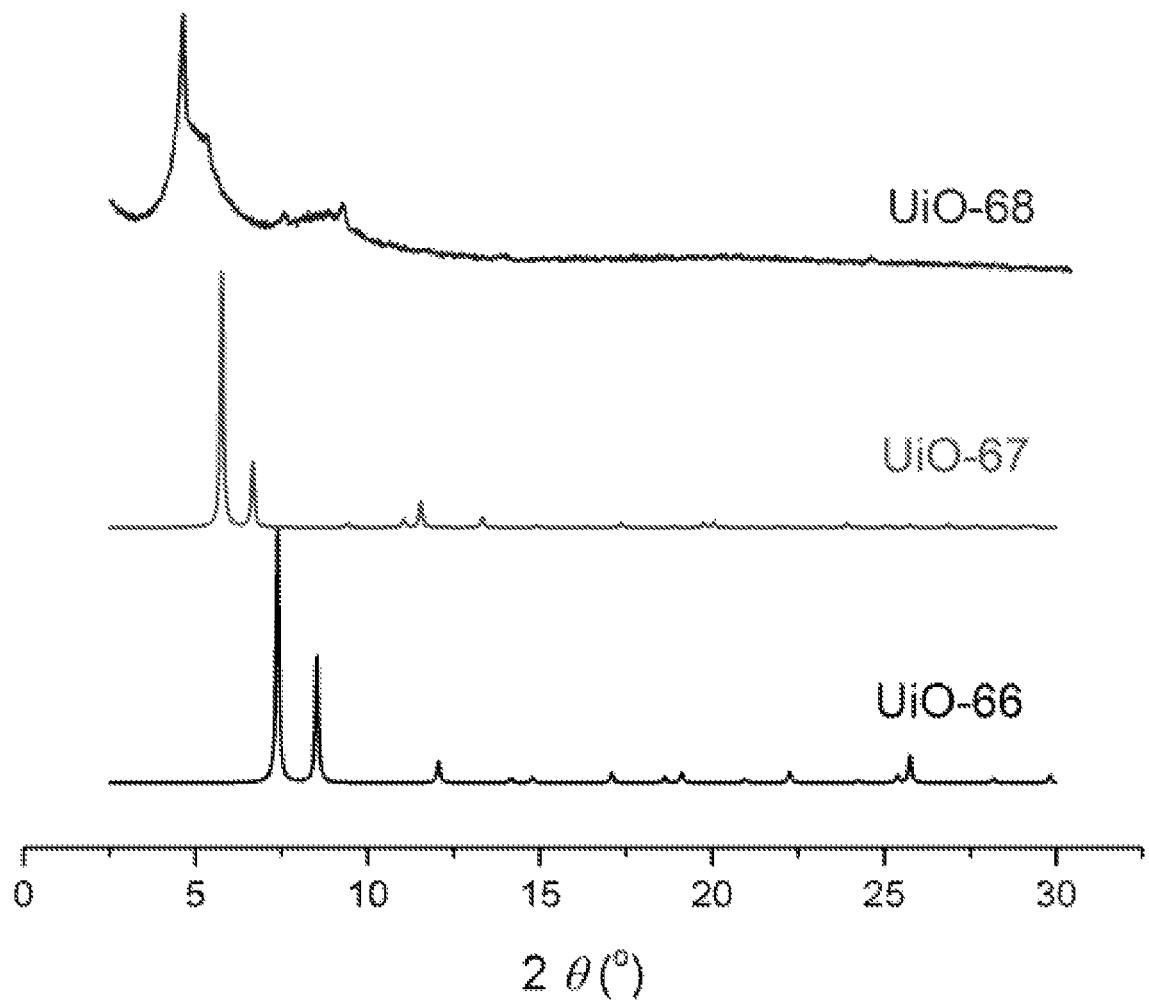
FIG. 4 depicts PXRD spectra of UiO-66, UiO-67-bpy and UiO-68-$N_3$.
Figure 5:
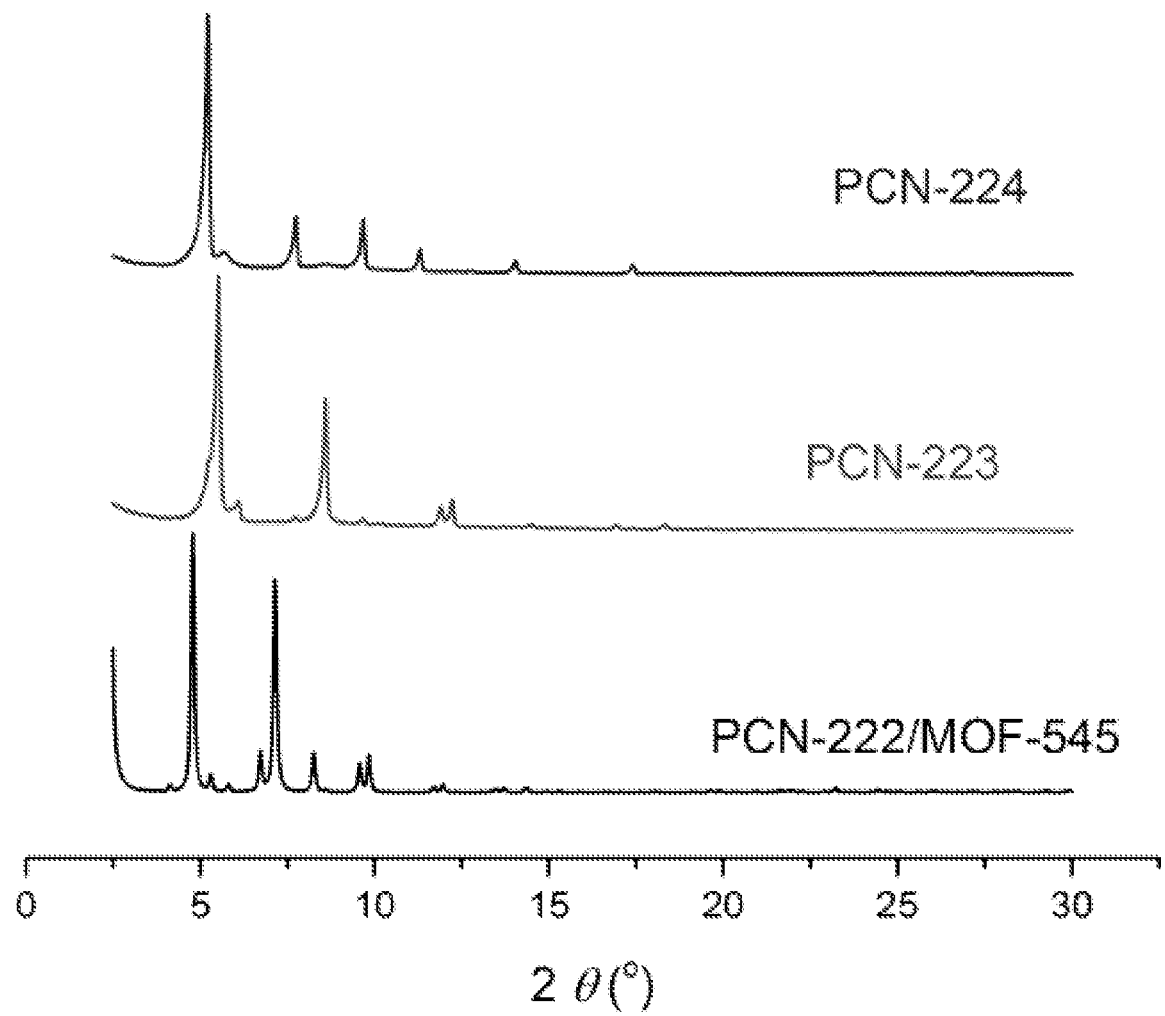
FIG. 5 shows PXRD spectra of PCN-222, PCN-223 and PCN-224.
Figure 6:
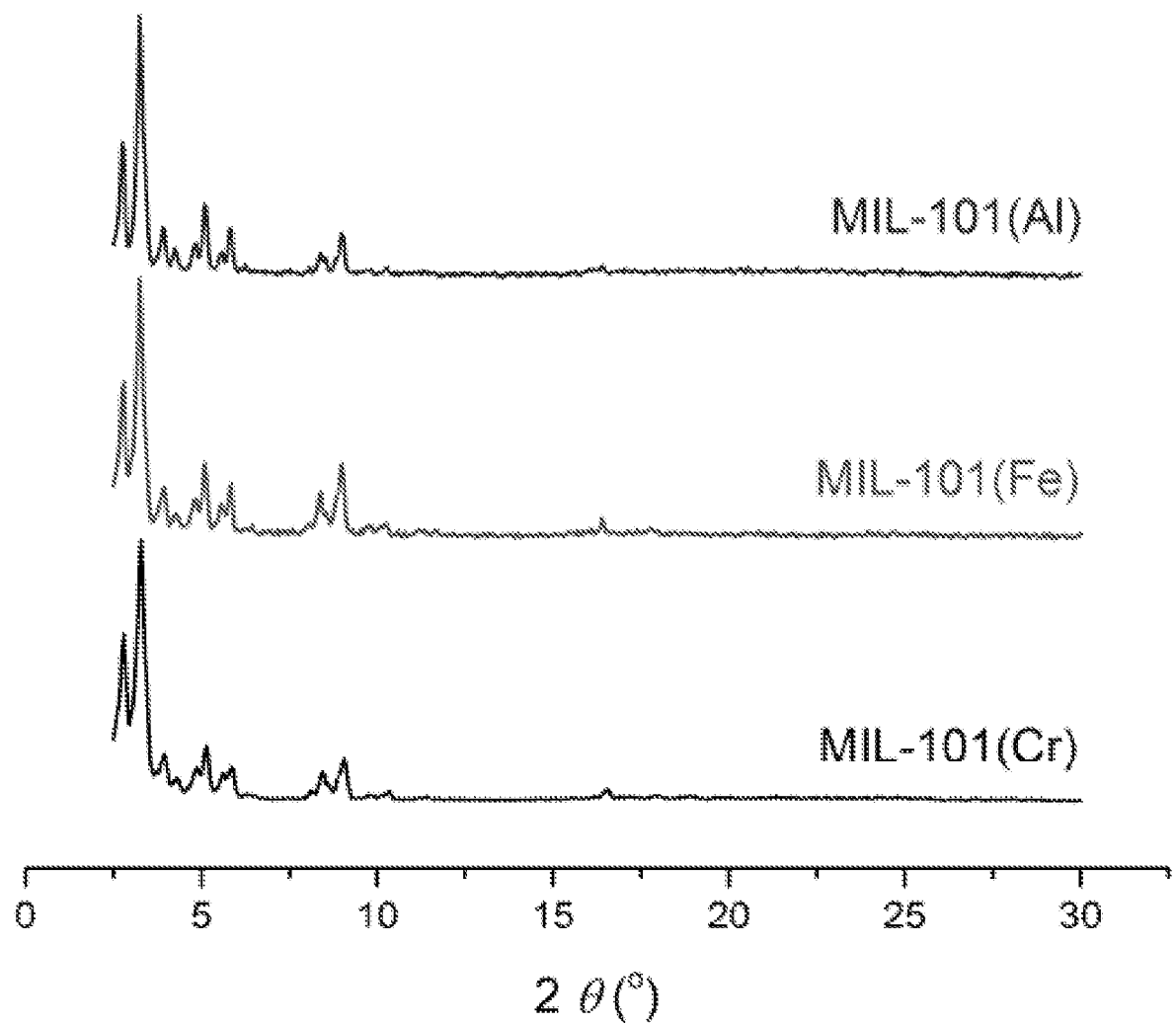
FIG. 6 shows PXRD spectra of MIL-101(Cr), MIL-101 (Fe) and MIL-101(Al).
Figure 7:
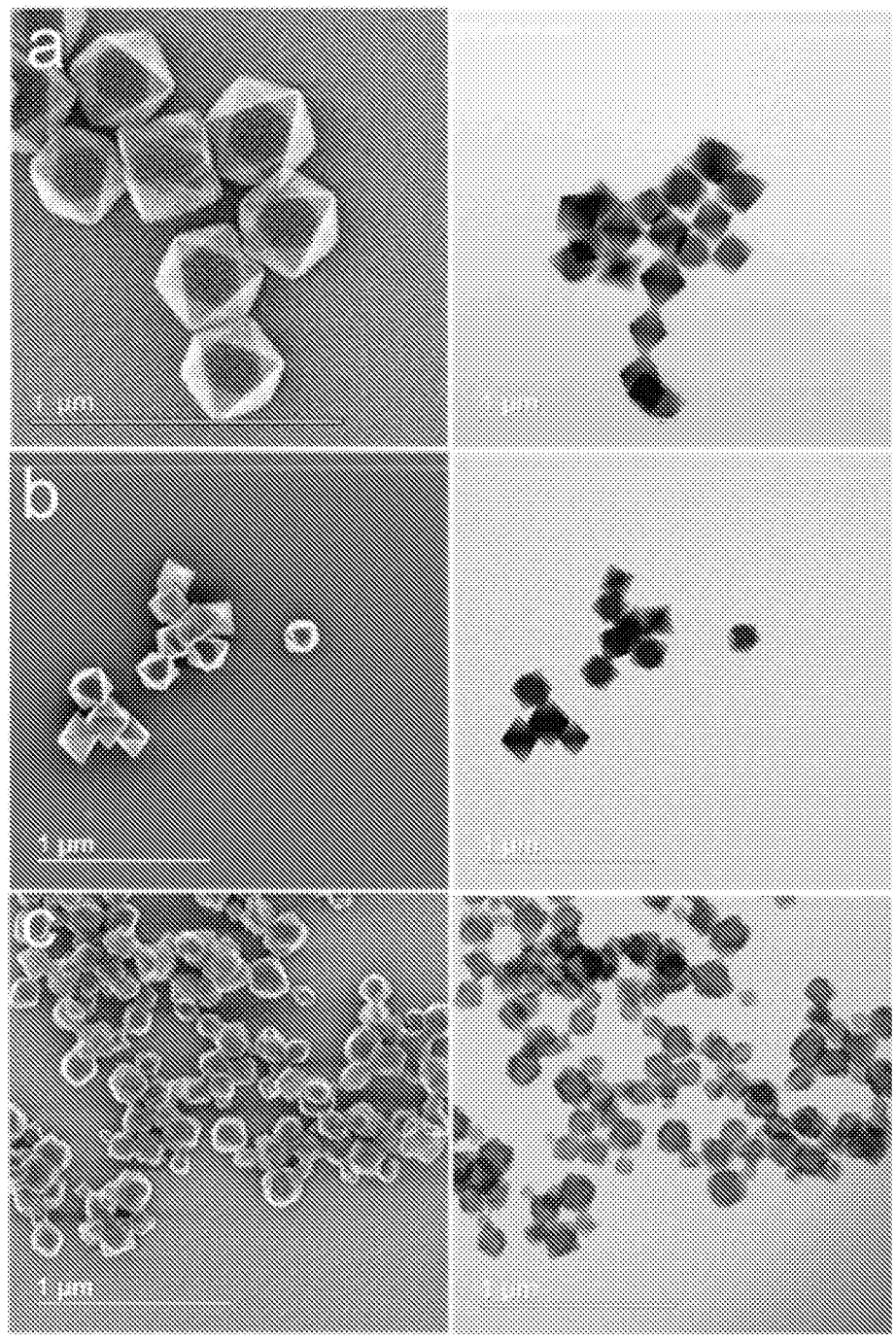
FIG. 7 shows SEM and TEM images of (a) UiO-66 (225±35 nm); (b) UiO-67-bpy (173±19 nm); and (c) UiO-68-$N_3$/PCN-58 (148±39 nm).
Figure 8:
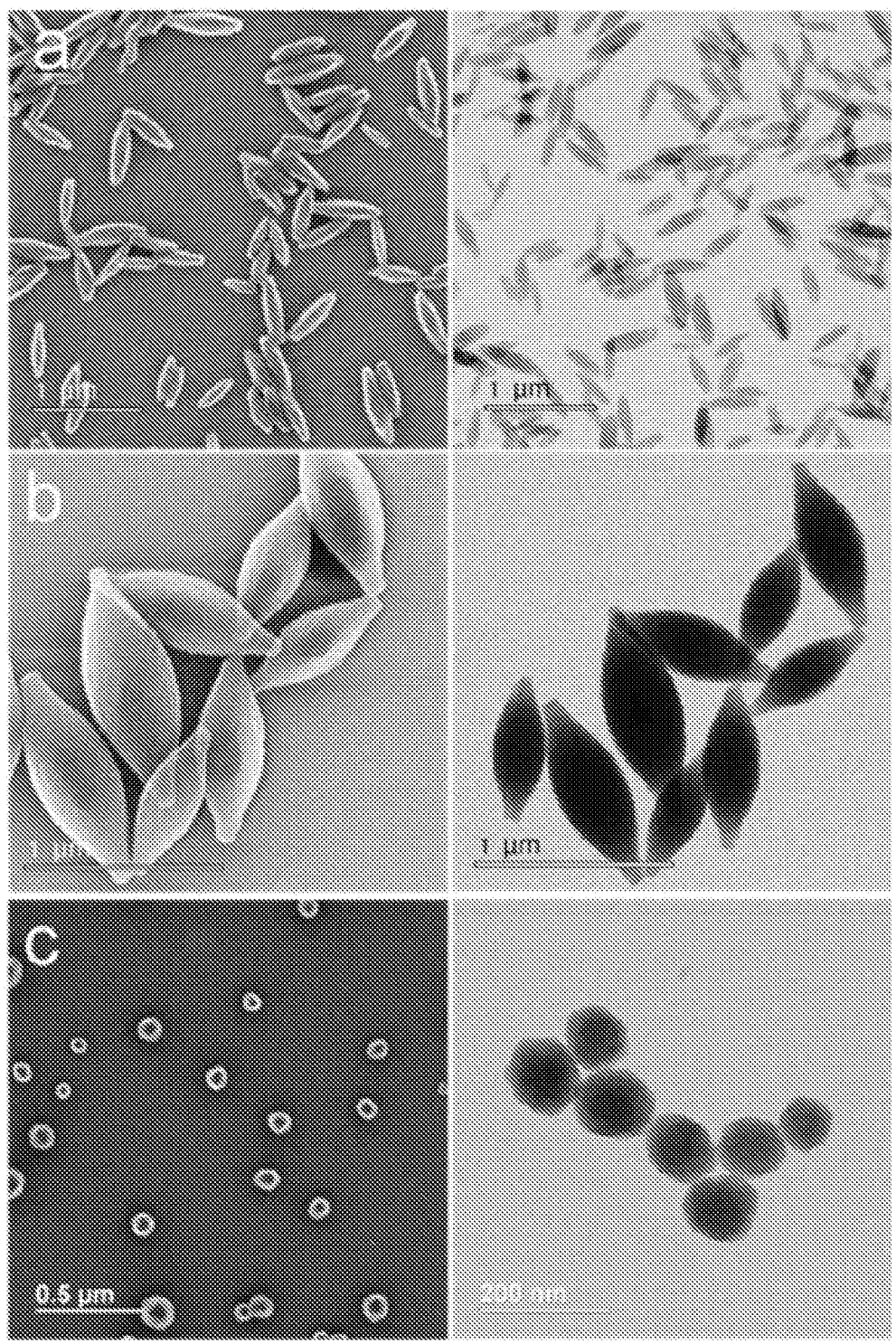
FIG. 8 shows SEM and TEM images of (a) PCN-222 (195×48 nm); (b) PCN-223 (538×48 nm); and (c) PCN-224 (110±24 nm).
Figure 9:
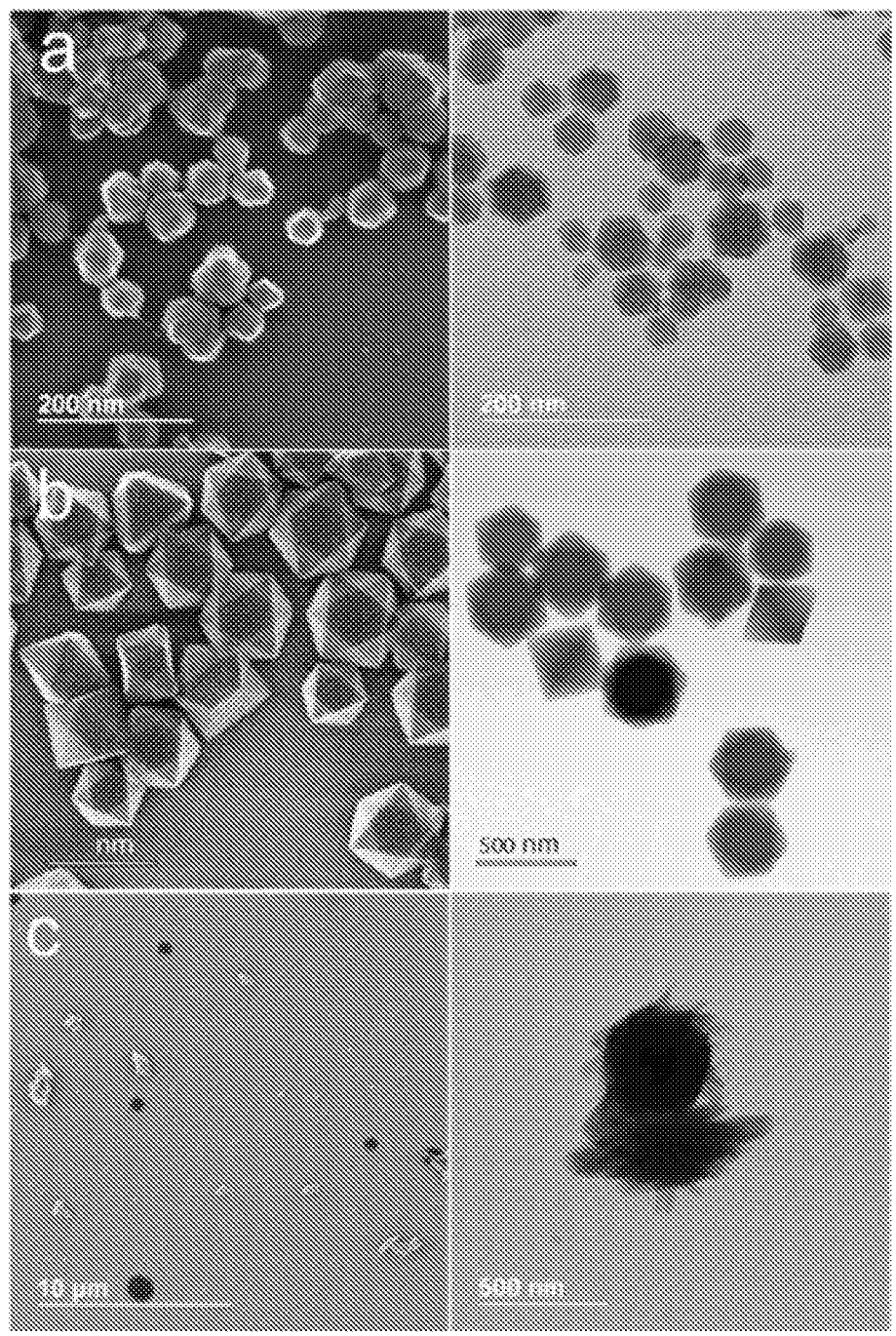
FIG. 9 shows SEM and TEM images of (a) MIL-101(Cr) (78±16 nm); (b) MIL-101(Fe) (470±57 nm); and (c) MIL-101(Al) (434±86 nm).

To evaluate the generality of this approach, nine distinct MOF architectures containing different metals and organic linkers were chosen, including UiO-66, UiO-67-bpy (2,2'-bipyridine-5',5'-dicarboxylic acid), UiO-68-N3/PCN-58, PCN-222/MOF-545, PCN-223, PCN-224, MIL-101 (Al), MIL-101 (Fe), and MIL101 (Cr), representing four distinct metal nodes, four distinct organic linkers, and five different topologies (FIG. 3). In addition to their high chemical stability, these MOFs show promise in nanomedicine.[25,26] MOF nanoparticle synthesis, characterization, and surface functionalization and quantification were carried out analogously to that described (FIGS. 4-9), following literature reports. In comparing these different MOFs, how SBU density, SBU coordination number, and metal-oxygen bond dissociation energy affect surface functionalization was tested.

It was hypothesized that DNA surface coverage would correlate with the density of SBUs present on the nanoparticle surface. To test this, three isoreticular Zr-based frameworks with the same underlying topology were synthesized, namely UiO-66, UiO-67-bpy, and UiO-68-$N_3$. Within this family, the density of surface metal nodes decreases as a function of increasing organic linker length, with the Zr oxide cluster SBU surface density (assuming (100) facet is exposed) estimated to be 0.27, 0.16, and 0.11 nm-2 for UiO-66, UiO-67-bpy, and UiO-68-$N_3$, respectively. As shown in FIG. 3a, by plotting the DNA surface coverage as a function of Zr SBU density on each MOF surface, a linear relationship was observed, where the ratio of DNA to Zr SBU is essentially constant: structures with more surface Zr have more DNA. This was the first demonstration of a quantitative correlation between DNA functionalization and surface SBU density on different MOFs, providing a way to select for MOF structures with the appropriate DNA surface loading for an intended use. Higher DNA loading density can significantly impact nanomaterial colloidal stability and certain biological applications where high DNA-loading is correlated with particle probe performance.

To test that MOFs with high SBU coordination numbers will result in higher DNA functionalization densities (due to more solvent-bound CUS on the nanoparticle surface), three Zr-based porphyrinic MOFs, PCN-222, PCN-223, and PCN-224, were synthesized from an identical tetracarboxyphenyl porphyrin linker (H$_2$TCPP). This resulted in structures that share different net topologies because of different SBU connectivity (FIG. 3b). Specifically, three different octahedral Zr$_6$ SBUs with coordination numbers of 8-, 12-, and 6- define each of these frameworks, and yield comparable surface SBU densities of 0.28, 0.25, and 0.28 nm$^{-2}$, respectively. As shown in FIG. 3b, a trend was seen where DNA surface coverage increases with SBU coordination number for three MOFs with comparable surface SBU density. This was because highly coordinated metal clusters expose higher degrees of surface defects due to coordination unsaturation,[27] which favors subsequent phosphate-DNA adsorption.

Whether the formation of stronger metal-phosphate bonds will facilitate greater extents of DNA adsorption was next tested (FIG. 3C). Three isostructural MIL-101 frameworks were synthesized: MIL-101 (Cr), MIL-101 (Fe), and MIL-101 (Al). Because identical structures are found in all three MOFs, the importance of phosphate-metal bond strength (postadsorption) on determining DNA surface coverage could be evaluated. Metal. oxygen bond dissociation energies (BDE) of 409, 477, and 512 kJ/mol for the Fe—O, Cr—O, and Al—O bonds, respectively, have been reported.[28] An increase in DNA surface coverage as a function of BDE was observed (FIG. 3C).

Finally, with an understanding of the stability and density of the oligonucleotides at the DNA-MOF nanoparticle conjugate surface, the hybridization and assembly properties of such structures with different DNA-NP sizes, shapes, and compositions was studied. In particular, DNA-MOF nanoparticles and archetypical inorganic gold nanoparticle (AuNP) SNA conjugates were used to synthesize hybrid core-satellite nanoclusters. In a typical experiment, AuNPs of different sizes were functionalized with a DNA sequence complementary to those on the MOF nanoparticles to facilitate assembly, the complements were mixed, salt-aged, and the resulting core-satellite hybrid architectures were isolated by low speed centrifugation. To confirm the morphology of the assembled nanoclusters, a developed silica encapsulation protocol for stabilizing DNA-nanoparticle assemblies was used, as shown in FIG. 10a.[29] Importantly, no MOF-AuNP nanoclusters form upon mixing of noncomplementary DNA-functionalized particles.

Figure 10:
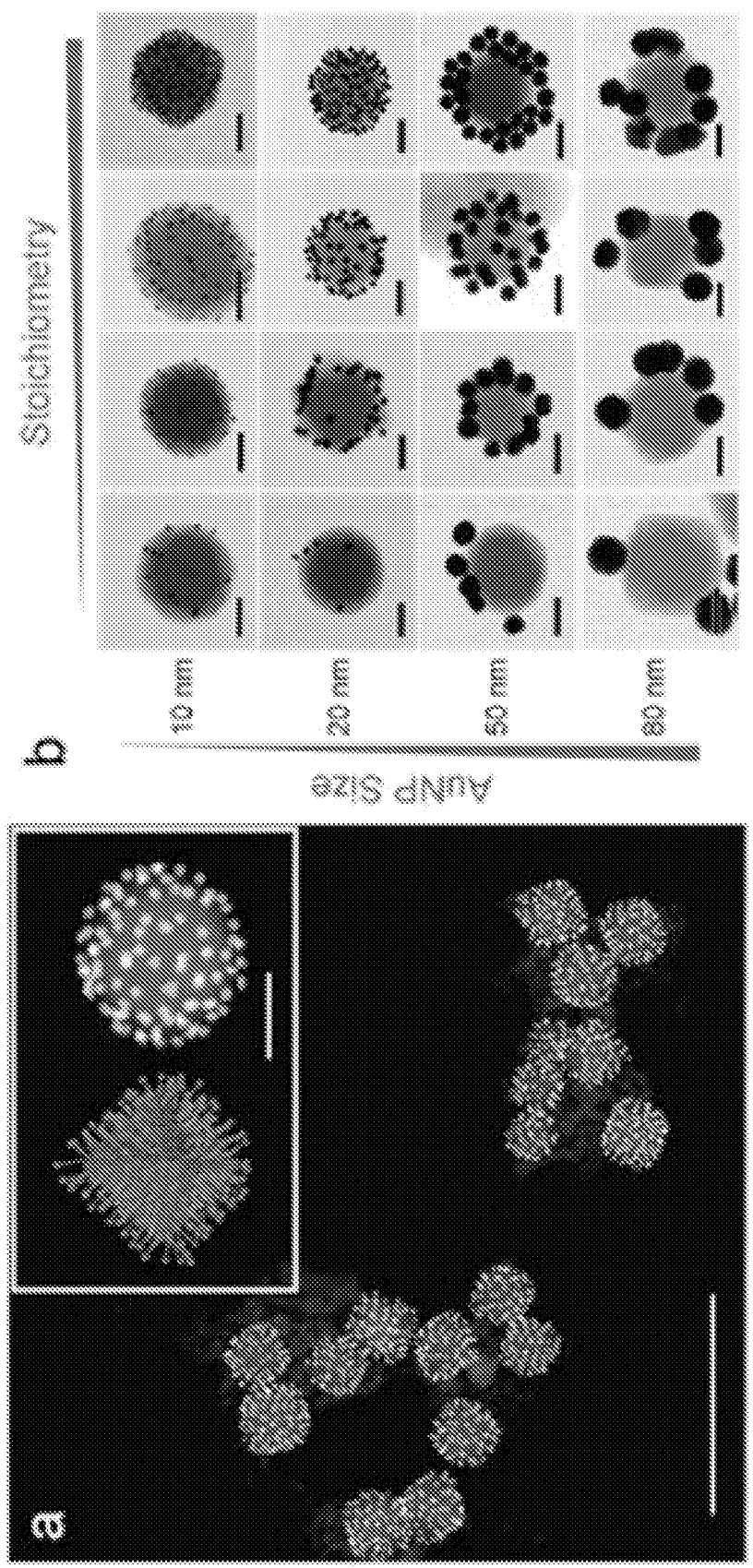
FIG. 10 shows TEM and EDX characterization of DNA interconnected MOF NP-Au NP assemblies. (a) Representative HAADF image of nanoclusters formed from complementary 225 nm DNA-UiO-66 MOF NPs and 20 nm DNA-Au NPs. Inset: schematic illustration of a MOF NP-AuNP cluster, and a single nanocluster. (b) TEM images of nanocluster assemblies demonstrating how the programmable DNA ligands on MOF NPs and AuNPs provide control over the structural makeup of the assemblies (Au NP size and MOF-to-Au NP stoichiometry). All scale bars are 100 nm, except for in panel a, where it is 1 μm.
Figure 11:
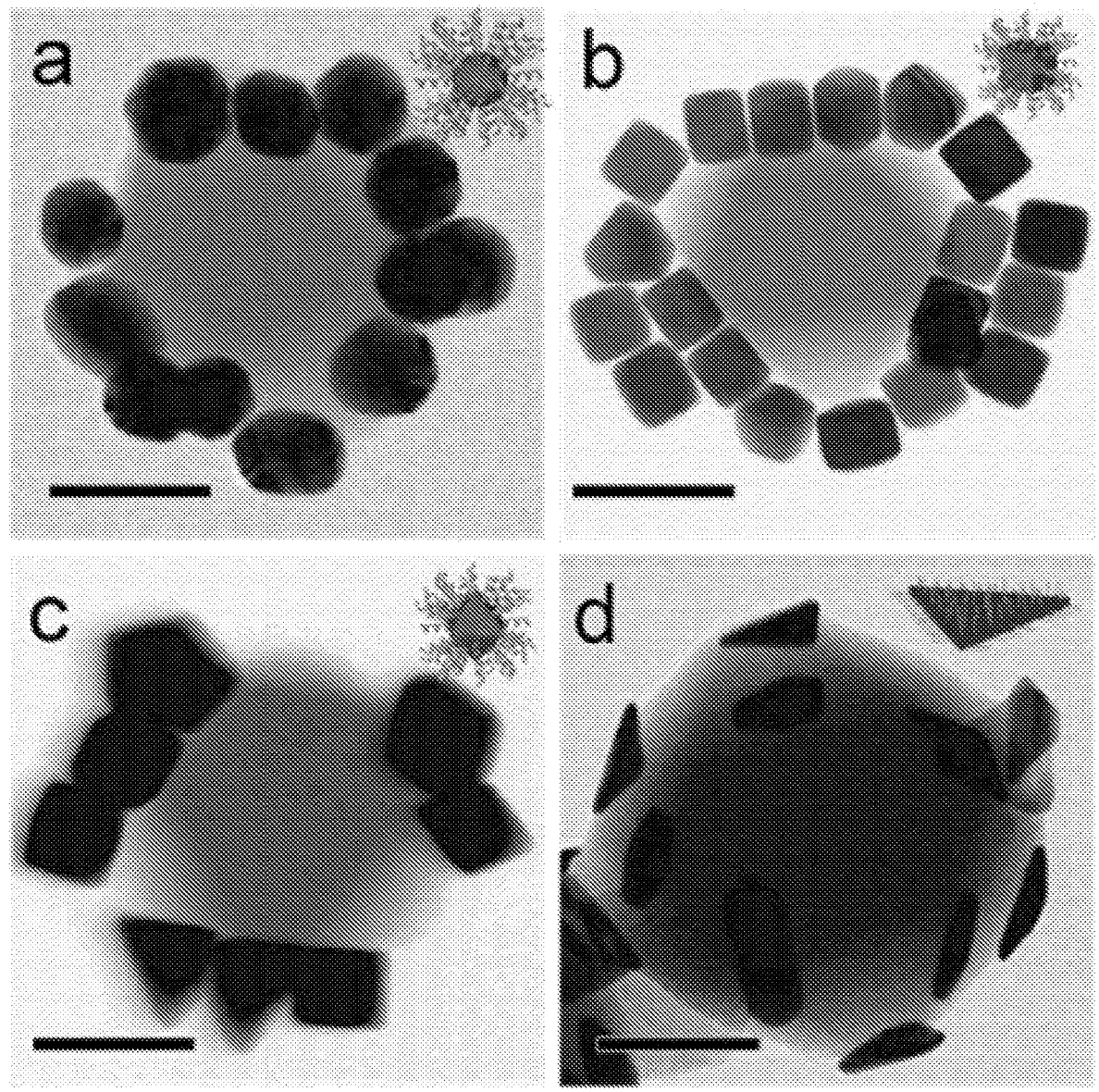
FIG. 11 shows TEM images of 225 nm DNA modified MOF NP core assembled with complementary DNA-modified AuNPs of various shapes: (a) spherical AuNPs (inset), (b) Au nano cubes (inset), (c) octahedral AuNPs (inset), (d) Au nanoprisms (inset). All scale bars are 100 nm.
Figure 12:
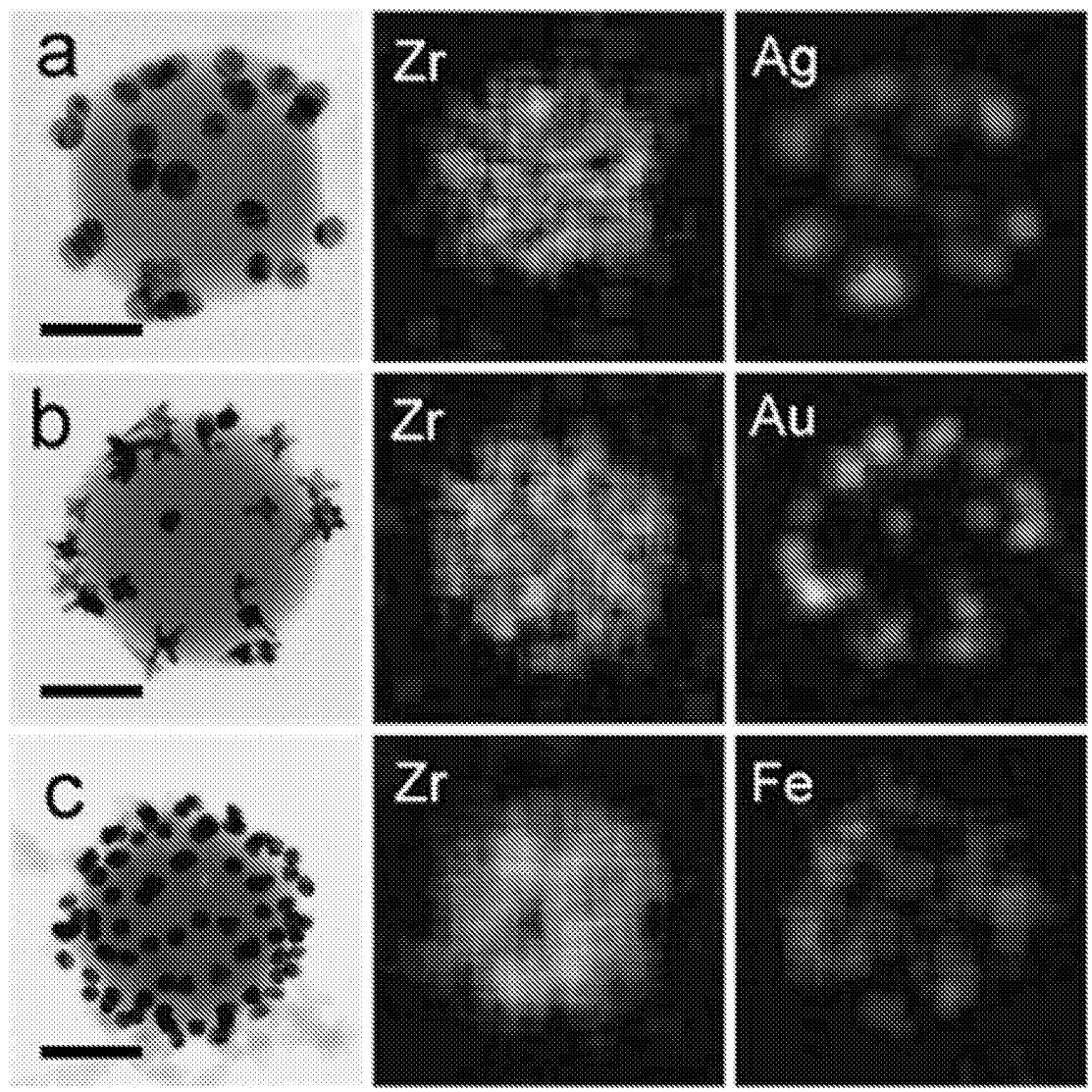
FIG. 12 depicts an exploration of the assembly of DNA-modified metal NPs (AgNP, AuNS, $Fe_3O_4$). EDS elemental mapping showing DNA-modified silver nanoparticles assembled around the complementary DNA-UiO-66 MOF NP (a), DNA-modified gold nanostars assembled around the complementary DNA-UiO-66 MOF NP (b), and DNA-modified iron oxide nanoparticles assembled around the complementary DNA-UiO-66 MOF NPs (c). All scale bars are 100 nm.
Figure 14:
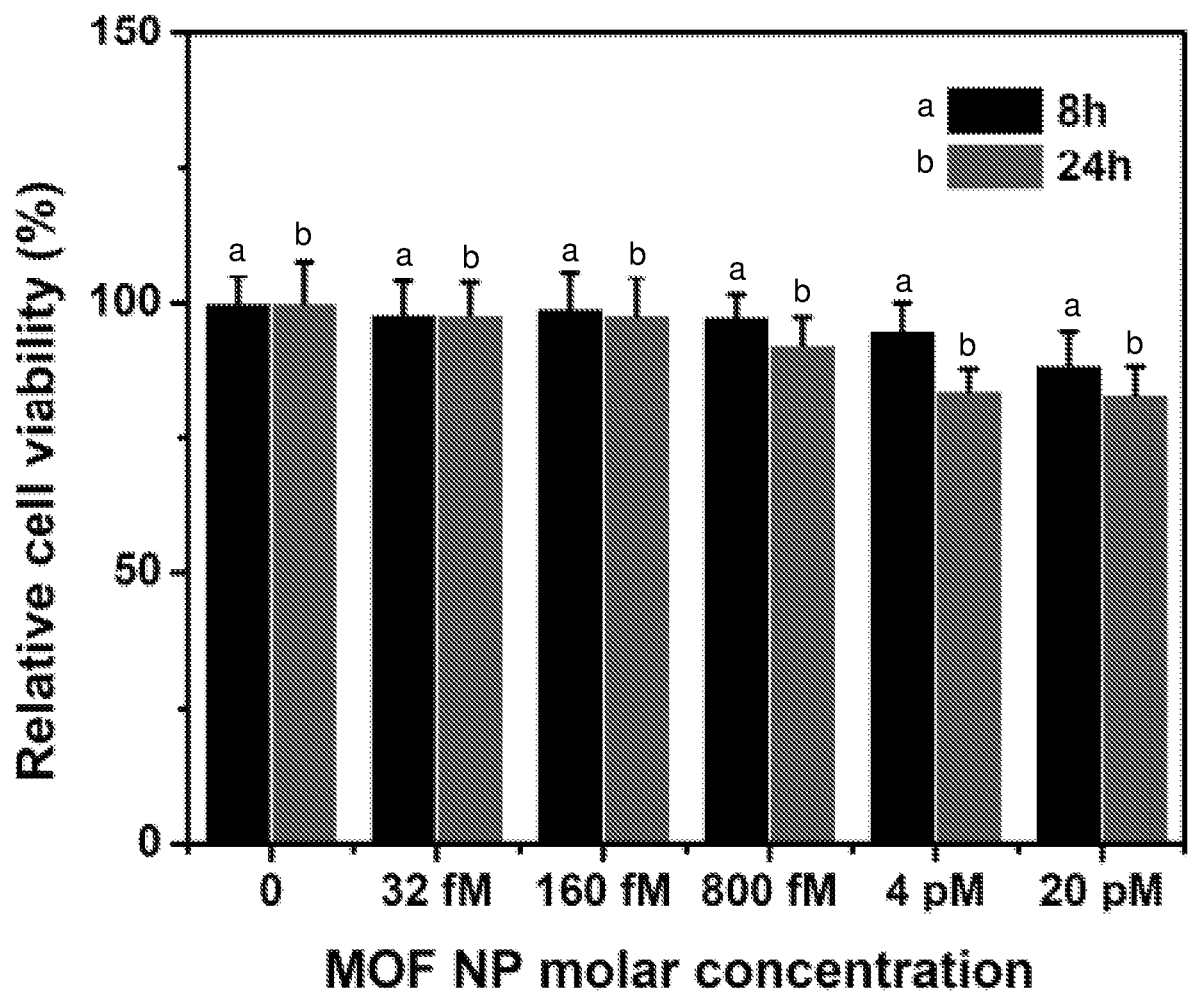
FIG. 14 shows results of an MTT assay verifying negligible cytotoxicity or anti-proliferative effects induced by MOF-NP nanoclusters.
Figure 19:
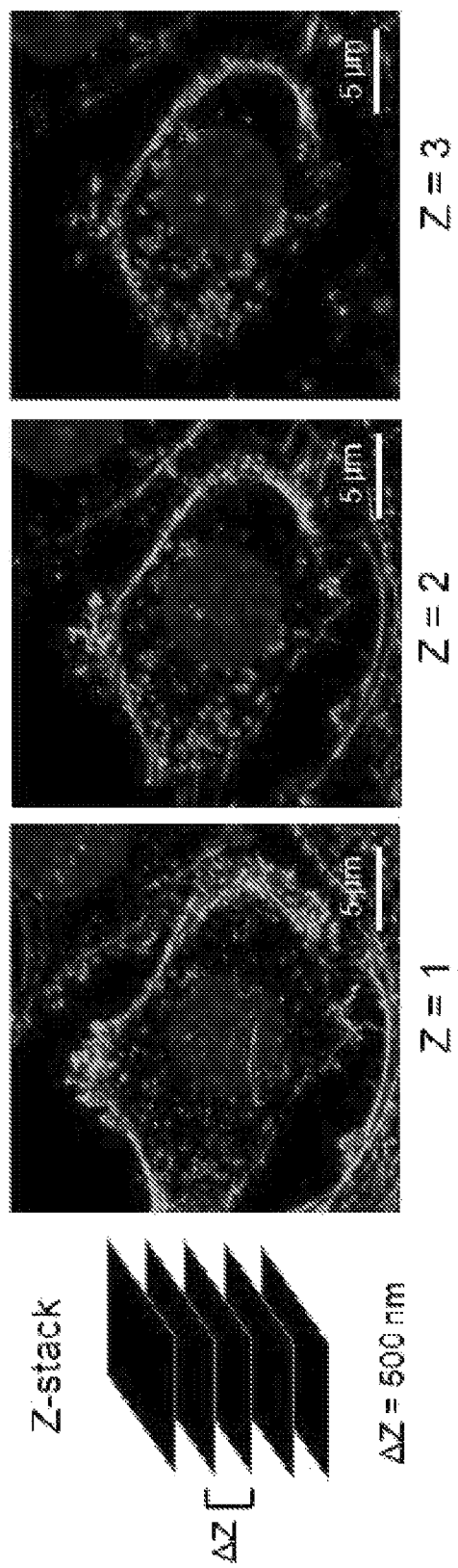
FIG. 19 shows confocal Z-stack images of hybridized nanoclusters, confirming cellular uptake.

By modifying the stoichiometry of the DNA-mediated hybridization reaction (by varying MOF NP:AuNP ratio from 1:20 to 1:2000), the loading of metal NPs on the central MOF particle could be controlled (FIG. 10b). The formation of MOF-NP nanocluster satellite structures was favored over polymeric structures at high AuNP:MOF ratios; once they formed, they exposed only identical noncomplementary DNA on the nanocluster periphery which inhibited the formation of extended networks via intercluster hybridization. To further explore the generality of this DNA-mediated approach, satellite structures were systematically assembled with MOF particle cores with a variety of DNA-functionalized NP building blocks, including gold nanostars, cubes, octahedra, and triangular prisms, silver spheres, and $Fe_3O_4$ spheres. TEM and energy-dispersive X-ray spectroscopy (EDX) mapping of the resulting structures show their clean formation (FIGS. 11 and 12). The cellular cytotoxicity and uptake properties of MOF-NP hybrid nanoclusters were also assessed. The enrichment of MOF-AuNP nanocluster in cellular vesicles over time was demonstrated by confocal laser scanning microscopy (FIGS. 13 and 19), where strong accumulation of the nanocluster in cellular vesicle was observed as compared to an equivalent amount of single strand dye-labeled DNA, with no appreciable cytotoxicity (FIG. 14). Together, the structures realized illustrate the versatility and potential utility of these new DNA-modified MOF NPs for programmable assembly and in applications where designer oligonucleotide interactions are relevant.

Figure 16:
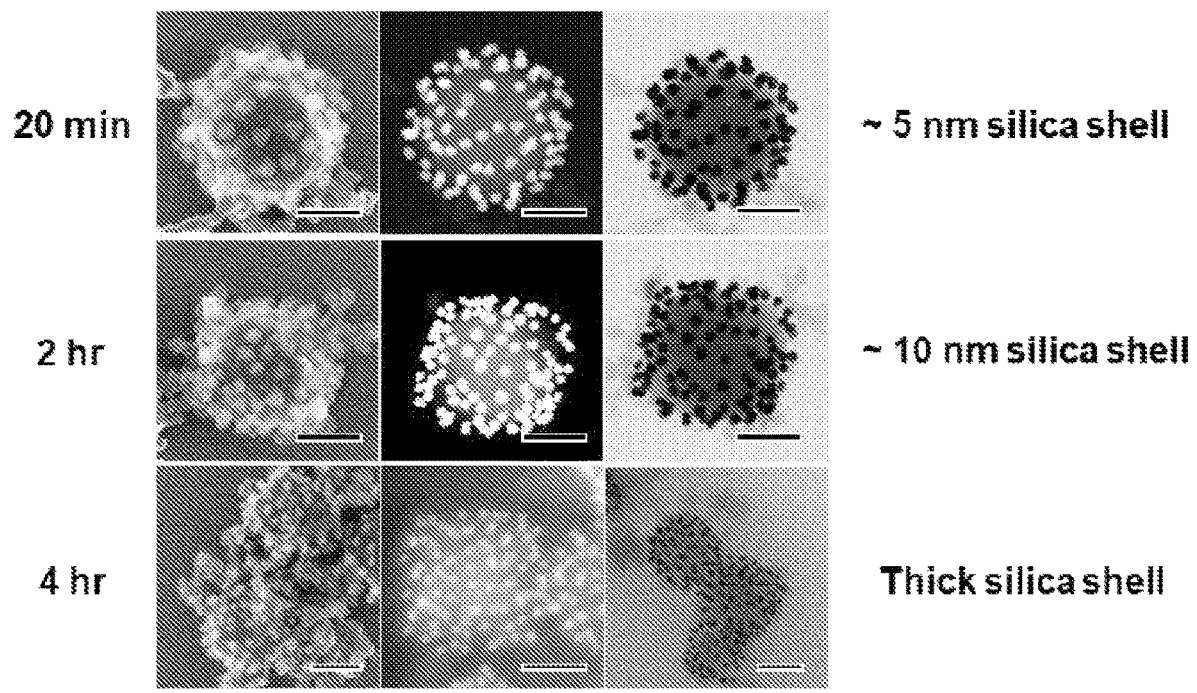
FIG. 16 shows cryo-TEM images confirming the formation of MOF-AuNP nanoclusters in solution.
Figure 17:
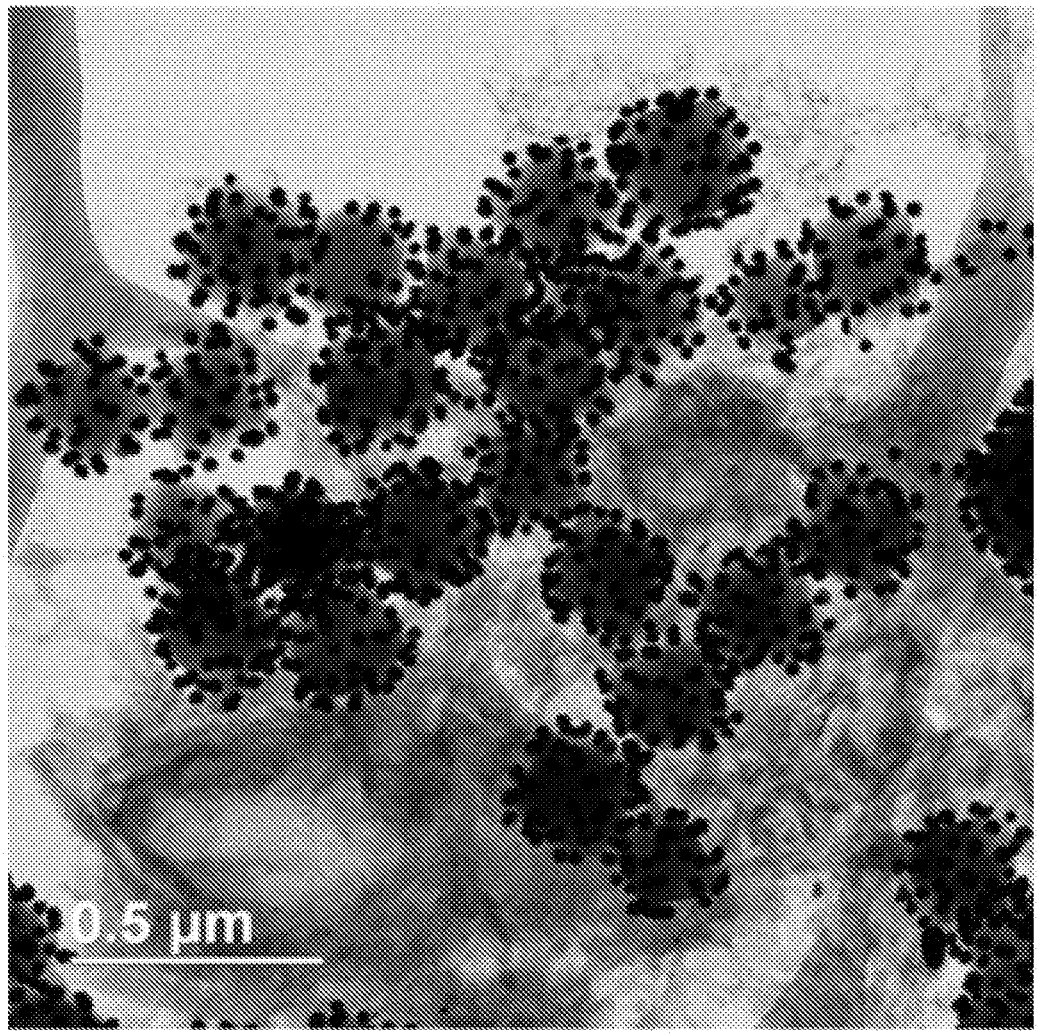
FIG. 17 shows a cryo-TEM image confirming the formation of MOF-AuNP nanoclusters in solution.
Figure 18:
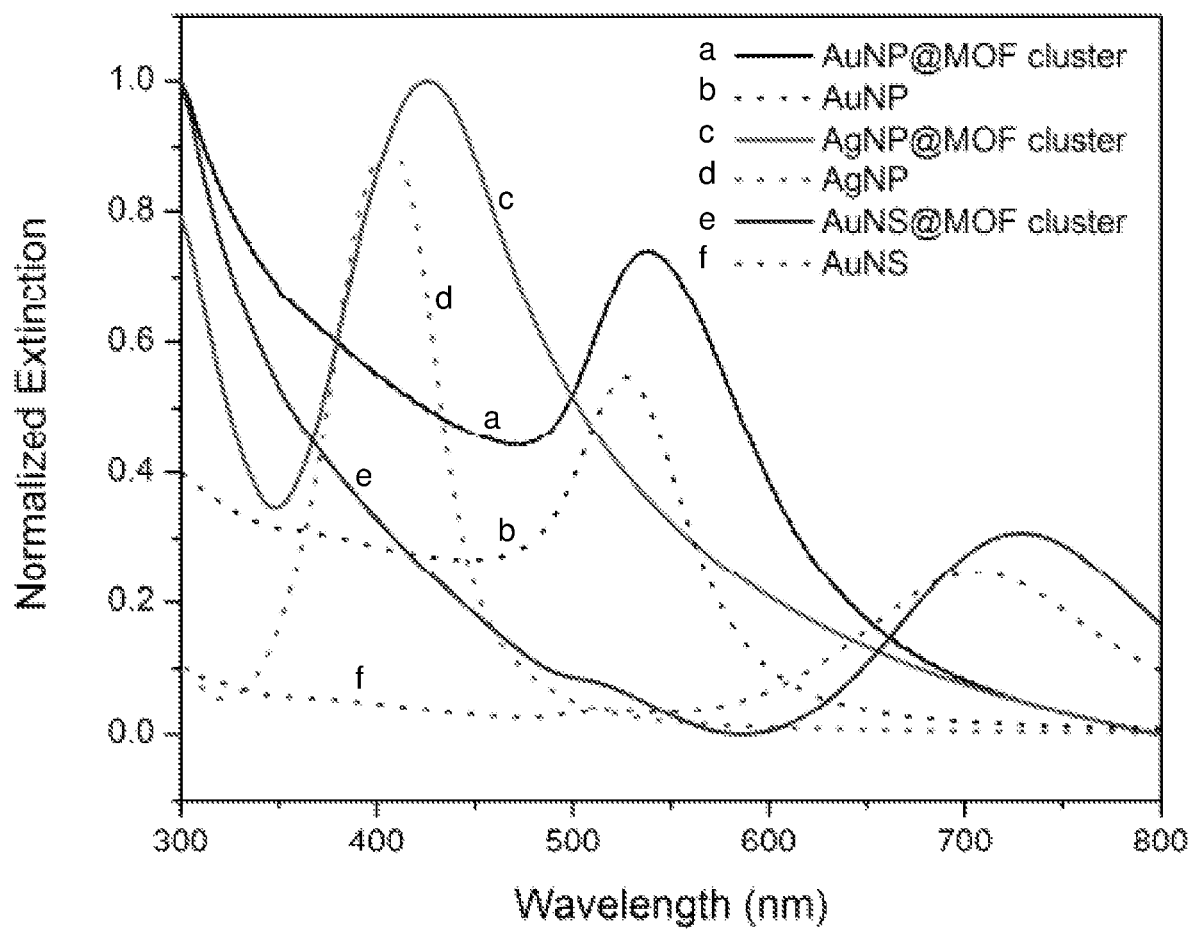
FIG. 18 shows results of experiments in which UV-vis spectroscopy was used to compare the extinction of the free colloidal nanoparticles with the assembled MOF-nanoparticle aggregates.

Cryogenic-transmission electron microscopy (Cryo-TEM) images confirmed the formation of MOF-AuNP nanoclusters in solution (FIGS. 16 and 17). Optical properties of MOF-NP core-satellite nanoclusters was also determined to compare the extinction of the free colloidal nanoparticles with the assembled MOF-nanoparticle aggregates. In all cases the extinction maximum is red-shifted from the free particle LSPR by about 20 nm, a well-known effect from assembling plasmonic nanoparticles (FIG. 18).

This example showed several advantages to the technology disclosed herein. First, it provides an approach to the synthesis of DNA-modified MOFs, independent of the choices of organic linkers and broadly applicable to a variety of metal clusters. Second, the structures realized are stable, have many of the original MOF characteristics, and can be programmably assembled with complementary DNA-modified NP building blocks. Third, design rules for modifying MOF NPs with DNA are emerging through this work. Most notably, it was shown herein that DNA surface coverage directly correlates with MOF nanoparticle surface SBU density, coordination number, and metal-phosphate bond strength. Finally, the experiments described herein provide a route to a broad class of NP building blocks with tunable properties that can be used to prepare designer materials with properties that are useful in biology,[30] catalysis,[31] and optics.[32]

Example 2

Materials

All reagents unless otherwise stated were obtained from commercial sources and were used without further purification. Human recombinant insulin (molecular formula: $C_{257}H_{383}N_{65}O_{77}S_6$, molecular weight: 5807.57, catalog number: 91077C-100MG) was purchased from Sigma-Aldrich, USA. Insulin, Alexa fluor 647 labeled Insulin (human) was purchased from NanoCS, USA. ELISA kit was purchased from Fisher Scientific, USA. All oligonucleotides used in this work were synthesized on a solid-support MM12 synthesizer with reagents purchased from Glen Research. The water used in all experiments was ultrapure deionized (DI) grade (18.2 MΩ·cm resistivity), obtained from a Milli-Q Biocel system (Millipore, Billerica, Mass., USA).

MOF NP Syntheses

Synthesis of 150 nm NU-1000 MOF NPs. 8 mg (34.3 nmol) of zirconium chloride and 2 mg (3 nmol) of 1,3,6,8-tetrakis(p-benzoic acid)pyrene (H4TBAPy) ligand were dissolved in 2.0 mL of N,N-Dimethylformamide (DMF), 0.4 ml acetic acid and 0.2 ml DI water was also added to the mixture solution resulting in a translucent yellow solution. Ten sample vials were prepared under the same conditions at once and were placed into an oven at 90° C. for 30 minutes, during which time a light yellow suspension was formed. After cooling down to room temperature, the 10 vials were combined and the nanocrystals were collected by centrifugation (15000 rpm, 30 minutes), followed by solvent exchange with DMF and acetone three times, then subsequently activated with HCl.

Synthesis of 10 μm NU-1000 MOF particles. The synthesis of 10 μm NU-1000 particle was based on a literature reported method.[43] Briefly, 70 mg of ZrCl4 (0.30 mmol) and 2700 mg (22 mmol) of benzoic acid were mixed in 8 mL of N,N-Diethylformamide (DEF) (in a 6-dram vial) and ultrasonically dissolved. The clear solution was incubated in an oven at 80° C. for 1 hour. After cooling down to room temperature, 40 mg (0.06 mmol) of $H_4TBAPy$ was added to this solution and the mixture was sonicated for 20 minutes. The yellow suspension was heated in an oven at 120° C. for 48 hours. After cooling down to room temperature, yellow single crystals were present on the vial walls. The sample was washed with DMF and acetone and subsequently activated with HCl.

Figure 20:
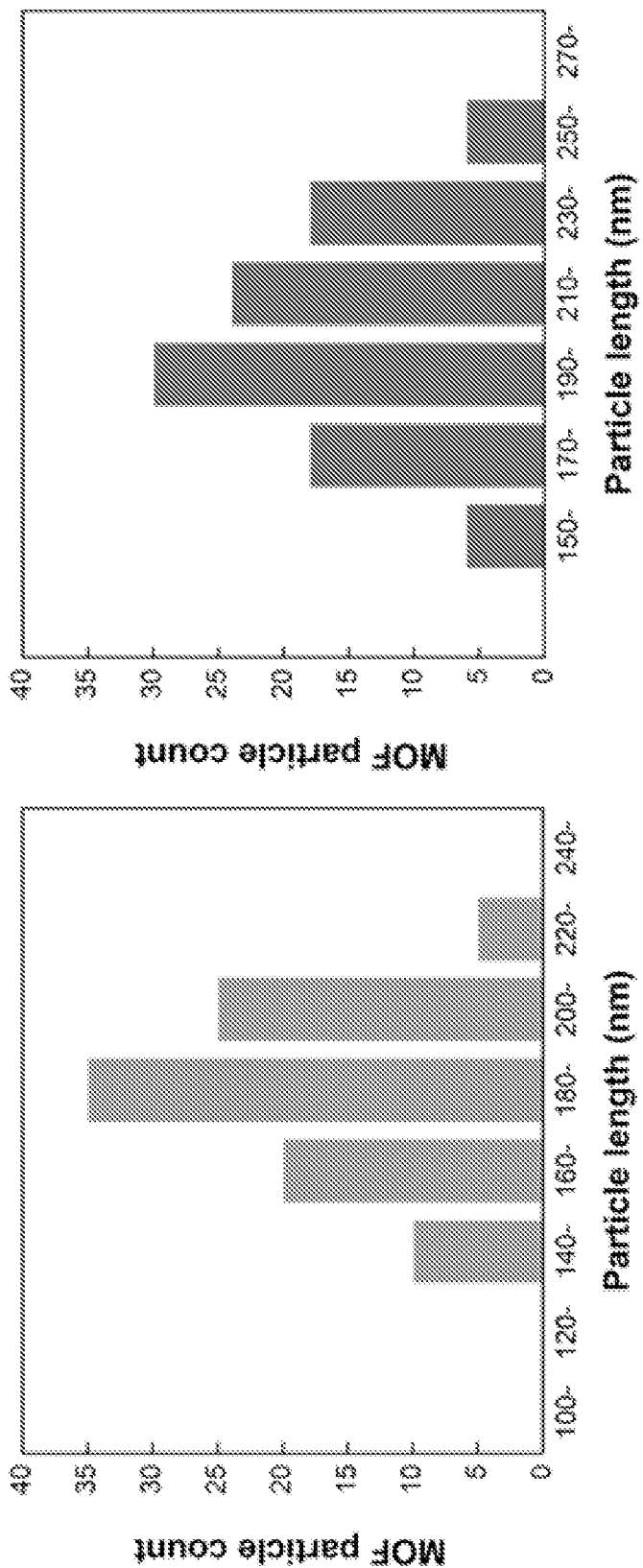
FIG. 20 depicts the size analyses of NU-1000 (left) and PCN-222 (right) NPs.

Synthesis of PCN-222 MOF NPs. The synthesis of 200 nm PCN-222/MOF-545 nanocrystal was based on a literature reported method with minor modifications.[44] Zirconyl chloride octahydrate (37.5 mg, 0.116 mmol) and tetrakis(4-carboxyphenyl)-porphyrin (6.5 mg, 0.0082 mmol) were dissolved in DMF (16.25 mL) in a 22 mL borosilicate vial with a Teflon-lined cap. Dichloroacetic acid (0.25 mL, 3.0 mmol) was added, and the resulting solution was heated at 130° C. for 18 hours to afford dark purple rod-shaped nanocrystals and a yellow mother liquor. The nanocrystals were collected by centrifugation (15000 rpm, 5 minutes), followed by solvent exchange with DMF. Size analyses of the resultant nanoparticles was performed (FIG. 20).

Figure 21:
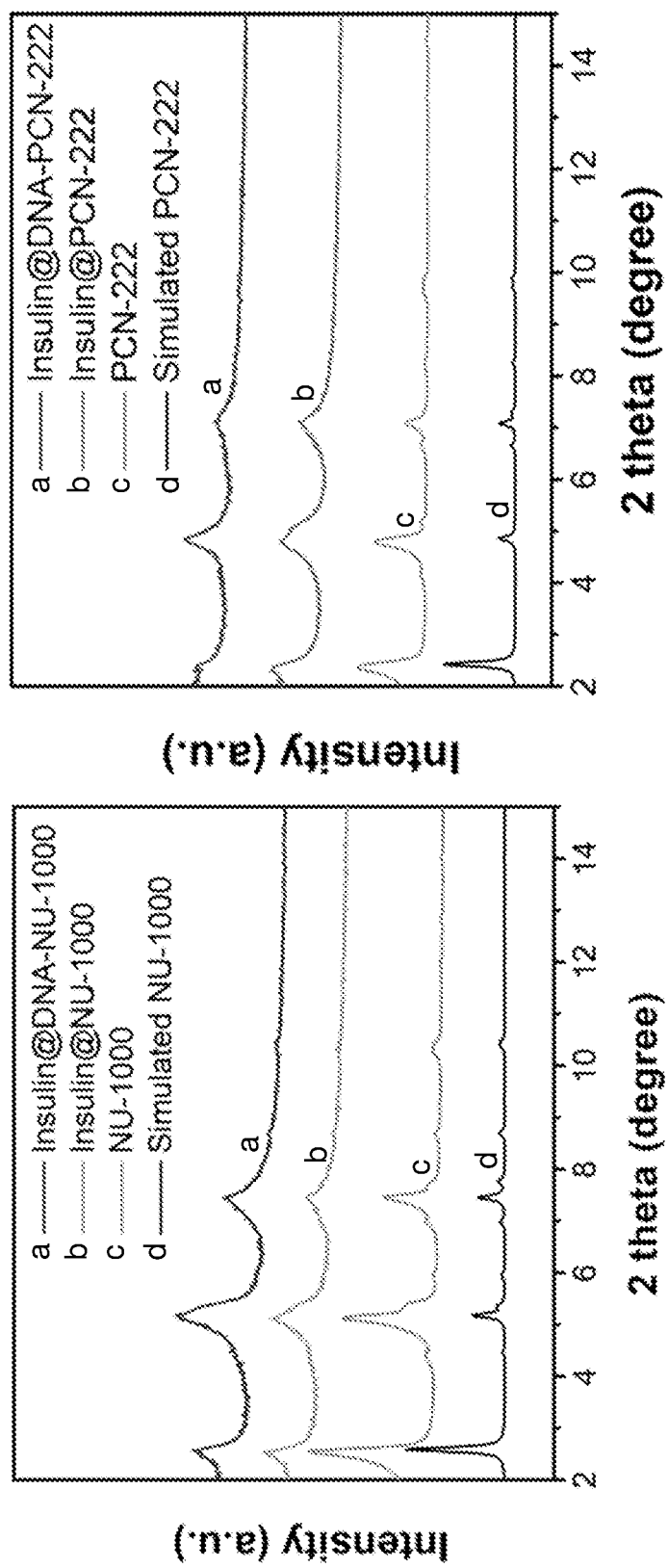
FIG. 21 shows PXRD spectra of as-synthesized, insulin encapsulated, and DNA-MOF conjugates for NU-1000 and PCN-222 NPs.

Powder X-ray diffraction. The crystallinity of the MOF nanoparticles (as-synthesized, insulin encapsulated, and insulin encapsulated DNA-MOF conjugates) were confirmed by powder X-ray diffraction (PXRD). Powder X-ray diffraction (PXRD) data (FIG. 21) were collected on a Rigaku model ATX-G diffractometer equipped with a Cu rotating anode X-ray source.

Insulin encapsulation. Activated MOF nanoparticles (3 mg) were treated with an insulin solution (in DI water, 0.4 mg/mL) for 1 hour at room temperature to encapsulate insulin. Insulin loading was measured by Inductively coupled plasma-optical emission spectroscopy (ICP-OES) and thermogravimetric analyses (TGA) based on literature reported methods.[45] To remove the insulin attached to the surface of MOF NPs, the supernatant was decanted and the solid sample was then washed with DI water for three times to remove the insulin molecules attached to the surface of the crystals.

DNA Synthesis and Functionalization

Synthesis of oligonucleotides. Oligonucleotides (Table 2) were synthesized using a Mermaid MM12 DNA synthesizer (Bio Automation) on a standard CPG solid phase support. All oligonucleotides were deprotected under conditions recommended by the manufacturer and purified by reverse phase high performance liquid chromatography (HPLC). Characterization and determination of concentrations were determined by matrix assisted laser desorption ionization (MALDI-TOF) mass spectrometry and UV-Vis spectroscopy, respectively.

TABLE 2

DNA sequences used in this example.

| # | Sequence Name | Sequence |
|---|---|---|
| 13 | polyG | 5'-(dGGT)$_{10}$-phosphate-3' |
| 214 | polyG-dye | 5'-(Tamra-dT)-(dGGT)$_{10}$-phosphate-3' |

3' Phosphate refers to 3-(4,4'-Dimethoxytrityloxy)-2,2-(dicarboxymethylamido)propyl-1-O-succinoyl-long chain alkylamino-CPG (3'-CPR II CPG).
Tamra-dT refers to 5'-Dimethoxytrityloxy-5-[N-((tetramethylrhodaminyl)-aminohexyl)-3-acrylimido]-2'-deoxyUridine-3'-[(2-cyanoethyl)-(N,N-diisopropyl)]-phosphoramidite (Tamra-dT).

Figure 22:
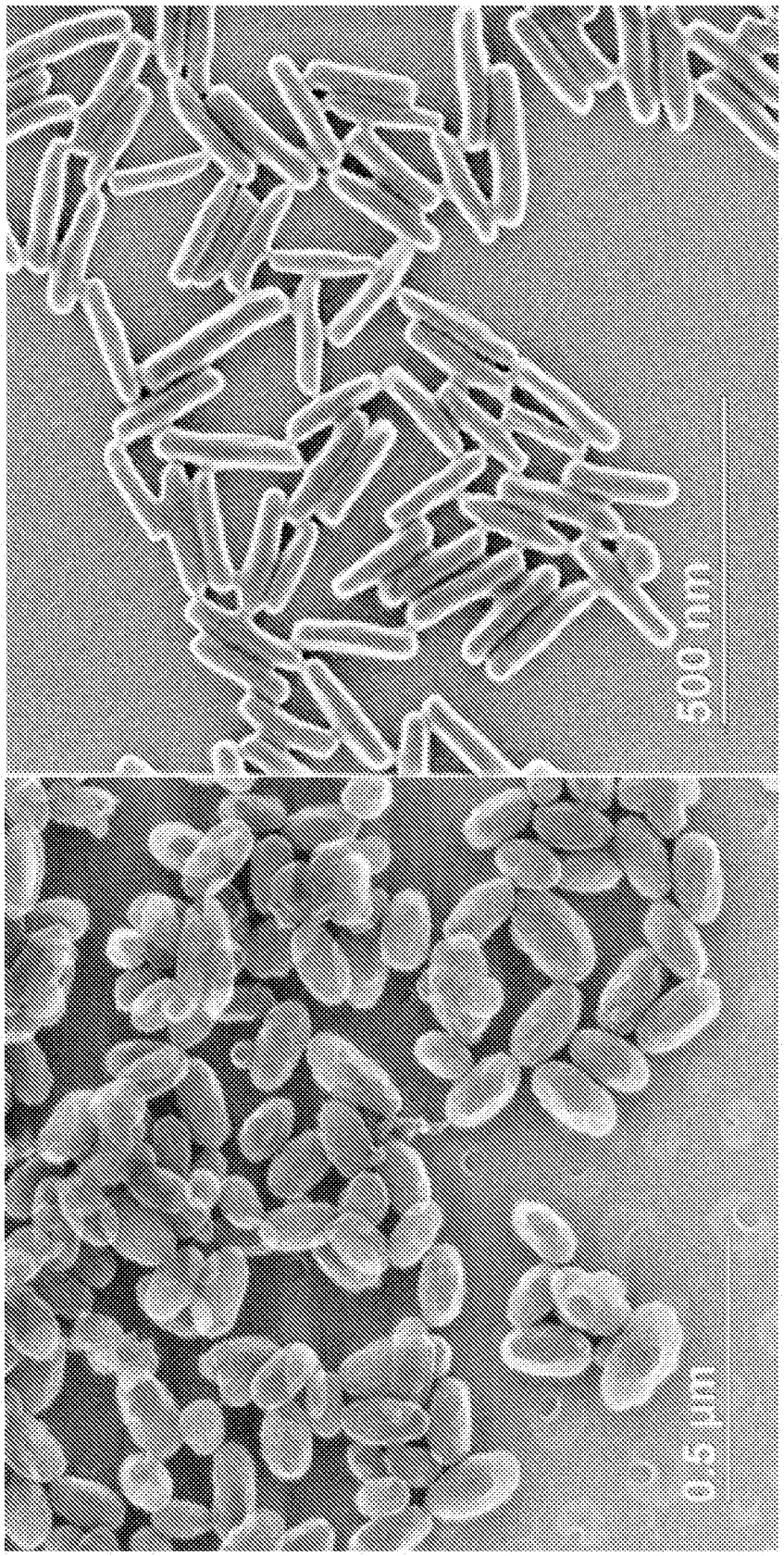
FIG. 22 shows SEM images that verify that the morphologies of DNA-NU-1000 (left) and DNA-PCN-222 (right) NPs are maintained post-DNA functionalization.
Figure 23:
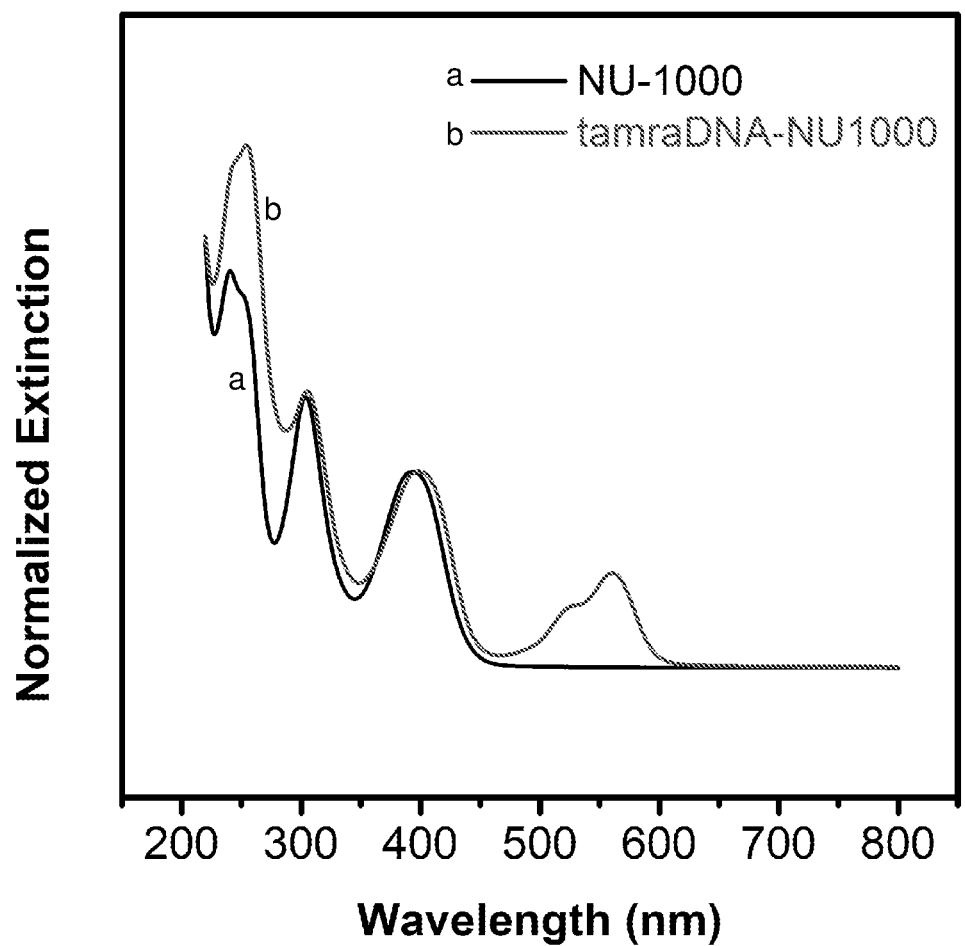
FIG. 23 depicts typical UV-vis spectra of Tamra-DNA-NU-1000 NP (red) and NU-1000 NP (black).

DNA functionalization. DNA functionalization of MOF NPs were conducted based on a previously reported method with minor modifications.[46] In a typical DNA functionalization experiment, excess phosphate terminated nucleic acid (approximately 100 nmol) was added to MOF NP colloids (approximately 2 mg), and then left on a shaker to incubate for 4 hours. Excess oligonucleotides were removed by centrifugation (3×10000 rpm, 15 minutes), and followed by resuspension in water. SEM images verified that the morphologies of DNA-NU-1000 and DNA-PCN-222 nanoparticles (NPs) were maintained post-DNA functionalization (FIG. 22). UV-vis spectra of Tamra-DNA-NU-1000 NP and NU-1000 NP were also obtained (FIG. 23).

Degradation Profiles of DNA-NU-1000 and DNA-PCN-222

Degradation profile in simulated extracellular matrices. To simulate intravascular and interstitial fluid, MOF NPs were incubated with DMEM buffer+blood serum (pH=7.0) at 37° C. with gentle shaking (400 rpm). Specifically, approximately 50 µg of DNA-NU-1000 and DNA-PCN-222 were first dispersed in 200 µL water to form the stock solution (0.25 mg/mL). Next, 7 identical samples containing 20 µL of the stock solution and 980 µL (DMEM buffer+blood serum solution) (pH=7.0) were prepared and incubated on a thermal shaker for 0.5, 1.5, 6, 12, 24, 48, and 72 hours, respectively. At each time point, one sample was collected and centrifuged (15000 rpm, 15 minutes) to remove remaining MOF NPs. The UV-vis absorbance of supernatant was measured and the percentage of linker release over time was calculated based on the standard curves.

Degradation profile in simulated intracellular matrices. A similar procedure was followed to measure the degradation profiles of DNA-NU-1000 and DNA-PCN-222 in 1×PBS solution to simulate their degradation in intracellular matrices (pH=7.0, 100 mM NaCl).

Figure 24:
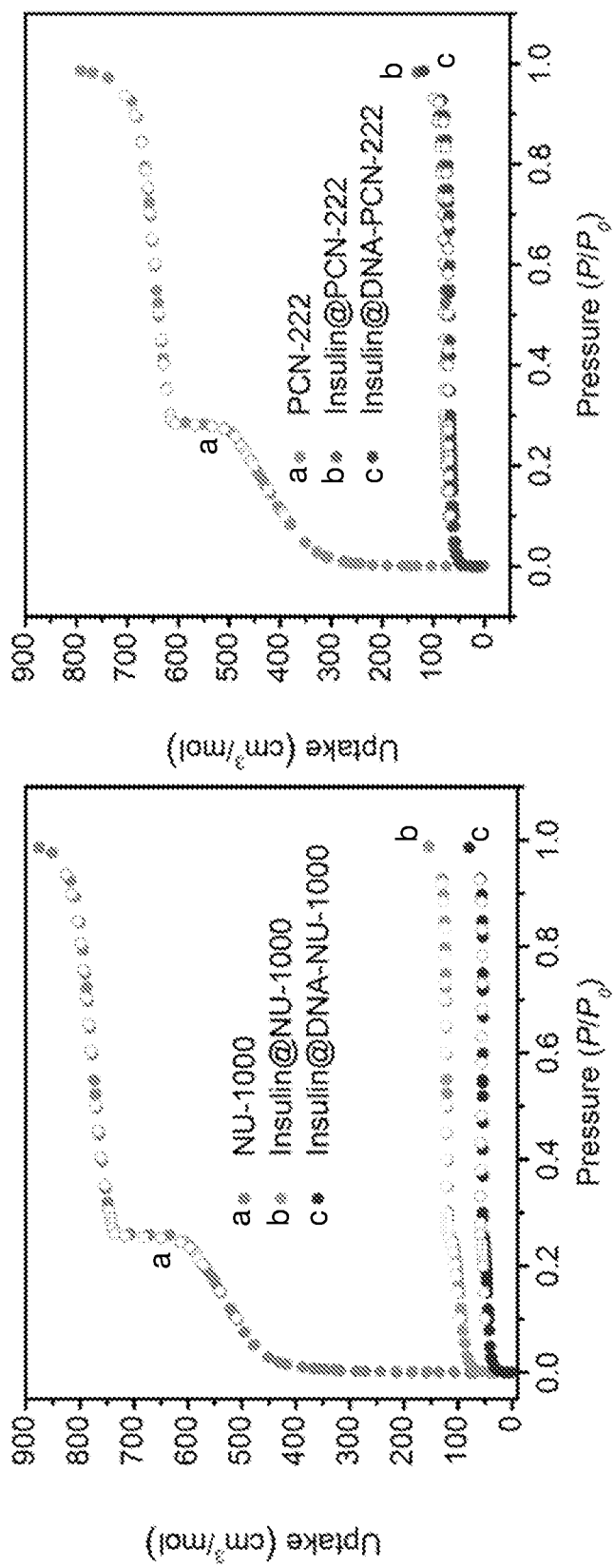
FIG. 24 shows N$_2$ adsorption-desorption isotherms that reveal significant surface area reduction after encapsulation of insulin and DNA functionalization.
Figure 25:
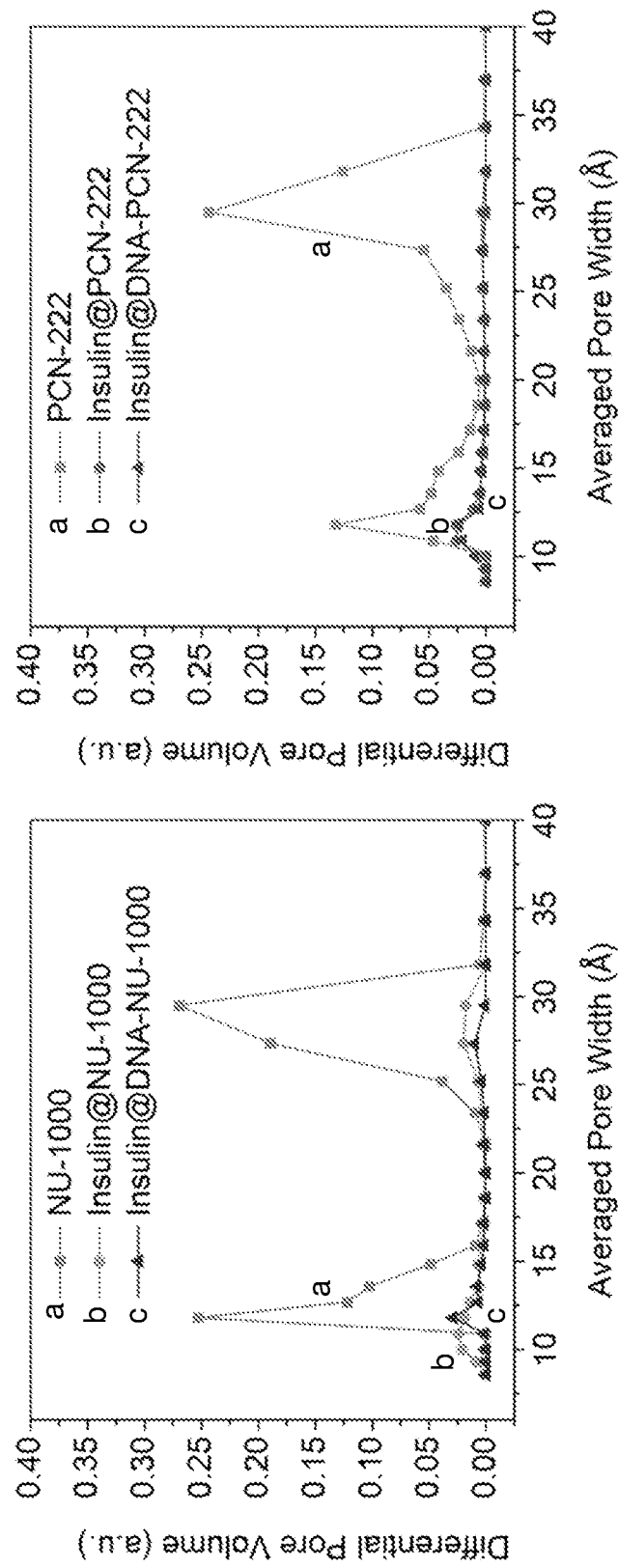
FIG. 25 shows DFT pore size distributions of NU-1000 and PCN-222 that suggest insulin occupies both the mesopores and micropores.

Nitrogen sorption isotherm measurements. $N_2$ sorption isotherm measurements were performed on a Micromeritics Tristar II3020 (Micromeritics, Norcross, Ga.) at 77K. Between 20 and 30 mg of material was used for each measurement. Surface areas were estimated by applying the Brunauer-Emmett-Teller (BET) equation. T-plot internal and external surface area were determined by Harkins and Jura equation in the second linear regions of $N_2$ isotherms (0.26 $P/P_0$ to 1.0 $P/P_0$) (FIG. 24). DFT pore size distributions of NU-1000 and PCN-222 suggested insulin occupies both the mesopores and micropores (FIG. 25).

Cell Uptake Experiments and Cytotoxicity Evaluation

Cell culture and incubation. Human ovarian cancer cells SK-OV-3(ATCC® HTB-77™) and mice melanoma cells B16-F10 (ATCC® CRL-6475) were incubated in incubators with 5% $CO_2$ at 37° C. Medium for these two cell lines was McCoy's 5A medium (ATCC® 30-2007™) and Dulbecco's Modified Eagle's Medium (DMEM) (ATCC® 30-2002™) representatively, containing 10% fetal bovine serum (FBS) and 1% antibiotics. Cells were passed every 2 or 3 days to get the acceptable confluence.

Cell imaging by confocal fluorescence microscopy. Confocal fluorescence microscopy was performed on confocal laser microscope (Zeiss LSM 800) system to verify that insulin@DNA-MOF NPs were internalized by the cells. SKOV-3 cells were plated in flourishes with 5×10$^4$ confluence. Insulin-encapsulated MOFs and free insulin were then incubated with cells (Table 3). After 6 hours, particles in medium were washed out and cells were fixed with 4% formaldehyde. Cell skeleton actin (F-actin) was stained with AlexaFluor 488 Phalloidin (ThermoFisher A12379).

TABLE 3

DNA and insulin concentration for sequences used in this study.

| # | Description | DNA concentration | Insulin concentration |
|---|---|---|---|
| 1 | AF647Insulin@tamra-DNA-NU-1000 | 100 nM | ~180 nM |
| 2 | AF647Insulin@tamra-DNA-PCN-222 | 100 nM | ~140 nM |
|   | Tamra-DNA | 100 nM |  |
| 3 | AF647Insulin |  | 160 nM |

Cellular Uptake by flow cytometry. LSR-II flow cytometry machine is used to identify the cellular uptake of both oligonucleotide and insulin. Skov-3 cells were first incubated in flow tubes with $5 \times 10^5$ concentration. Then insulin@DNA-MOFs, and control (free insulin+free DNA) were then incubated with cells (Table 3). After 15 minutes or 2 hours, particles were washed out and cells were fixed with 4% formaldehyde. Flow data were first gated by SSA and FSA parameter and positive gating in each channel is based on negative controls.

MTT assay. The anti-proliferative effects of insulin@DNA-MOF constructs were evaluated by MTT assay. Specifically, B16-F10 cells were seeded in a 96-well cell culture plate in DMEM medium at a density of $5 \times 10^4$ cells/mL with 10% fetal bovine serum (FBS) and 5% $CO_2$ at 37° C. for 24 hours. Next, the culture medium was replaced by 200 μL of DMEM medium containing samples at different concentrations (with non-labeled DNA and insulin) and cultured for 72 hours. Then, 10 μL of 5 mg/mL MTT solution (10% SDS) was added to each cell well. The cells were further incubated for 4 hours, followed by removal of the culture medium with MTT. Finally, 100 μL of 10% SDS was added and incubated overnight at 37° C. The absorbance of MTT at 492 nm was measured on an automatic ELISA analyzer (SPR-960), with a reference absorbance at 977 nm. Each experiment was conducted 3 times and the averaged data were presented.

Results/Discussion

Due to their aqueous-stability and mesoporous channel structures, two zirconium mesoporous MOFs, NU-1000 and PCN-222/MOF-545,[89-91] were synthesized as nanoparticles to encapsulate insulin as the model enzyme (FIG. 26b).[92-93] Next, these insulin@MOF NPs were surface functionalized with terminal phosphate-modified DNA to yield insulin@DNA-MOF (FIG. 26c), where the 3D oligonucleotide shell creates a steric and electrostatic barrier to stabilize MOF NPs in high dielectric media and render them functional with respect to cellular entry.77 This strategy can be generalized to MOFs of different pore sizes, and to create a library of nucleic acid-MOF-based delivery vehicles for transporting functional enzymes across cellular membranes with high payload.

Figure 27:
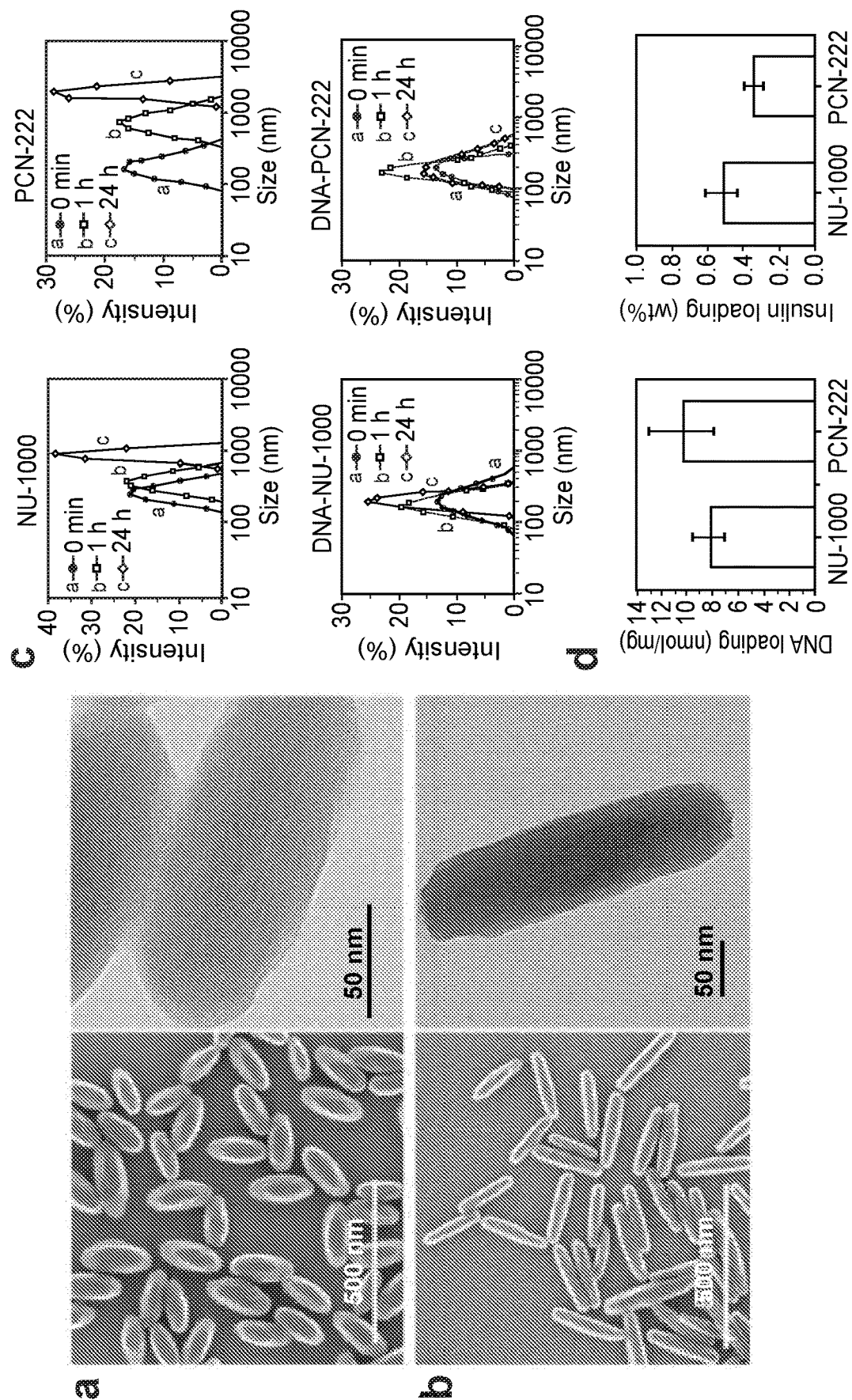
FIG. 27 shows (a) Scanning electron microscopy images (left) and transmission electron microscopy (right) images of the as-synthesized NU-1000 NPs. (b) SEM (left) and TEM (right) images of the as-synthesized PCN-222 NPs. (c) Colloidal stability of NU-1000 and PCN-222 in cell medium measured by DLS for the as-synthesized NPs (top) and DNA functionalized NPs (bottom). (d) DNA loading and insulin encapsulation density for NU-1000 and PCN-222 MOF NPs.

MOF NP syntheses and insulin encapsulations were realized following literature reports.[94-95] Briefly, NU-1000 MOF NPs (180(20)×70(10) nm) were synthesized via a solvothermal reaction of zirconium chloride ($ZrCl_4$), (4,4', 4'',4'''-(porphine-5,10,15,20-tetrayl)tetrakis(benzoic acid) ($H_4TBAPy$), and acetic acid in DMF at 90° C. (FIG. 27a). PCN-222 NPs (210(30)×50(10) nm) were synthesized via a solvothermal reaction of zirconyl chloride octahydrate ($ZrOCl_2 \cdot 8H_2O$), tetrakis(4-carboxyphenyl)porphyrin (TCPP), dichloroacetic acid in N,N-Dimethylformamide (DMF) at 130° C. (FIG. 27b). Next, the activated crystals of NU-1000 were treated with a bis-tris-propane buffer (BTP, pH=7) solution containing insulin. The encapsulation efficiency of insulin by MOF NPs were determined by inductively coupled plasma-optical emission spectroscopy (ICP-OES), and a maximum loading of 39 and 34 wt % were determined for NU-1000 and PCN-222 NP, respectively (FIG. 27d). Excess insulin in the supernatant and those adsorbed on the particle external surface were removed by sequential steps of washing with DI water and trypsin solution.

To functionalize insulin@MOF NPs with nucleic acids, the dense coordinatively unsaturated Zr was chemically addressed on NU-1000 and PCN-222 NP surface, using terminal phosphate-modified oligonucleotides.[96] Phosphate modified nucleic acids were synthesized on a DNA synthesizer, employing 3' phosphate modified phosphoramidites. The sequence used here, 5' $(dGGT)_{10}$-phosphate 3', was chosen based on previous work that showed enhanced cellular uptake of SNAs with a G-rich shell, relative to poly dT shells.[97] In a typical DNA functionalization experiment, excess oligonucleotides were added to a colloidal dispersion of MOF NPs and incubated for 4 hours (as described herein). Quantification of DNA coverage of both MOF NPs was achieved by ICP-OES based on the P to Zr ratio, where DNA loading of 8±1 nmol/mg and 10±1 nmol/mg were measured for NU-1000 and PCN-222 NPs, respectively (FIG. 27d). Powder X-ray diffraction (PXRD) and scanning electron microscopy (SEM) verified the crystallinity and morphologies of MOF NPs were preserved post-DNA functionalization (FIG. 22). Importantly, dynamic light scattering (DLS) verified that DNA surface functionalization significantly increases MOF NP colloidal stability in bio-relevant media. As shown in FIG. 27c, DNA functionalized NU-1000 and PCN-222 NPs are colloidally stable in cellular medium (90% DMEM buffer+10% fetal bovine serum) for at least 24 hours, whereas unfunctionalized NU-1000 aggregated in less than one hour, hampering their further in vitro applications.

Figure 28:
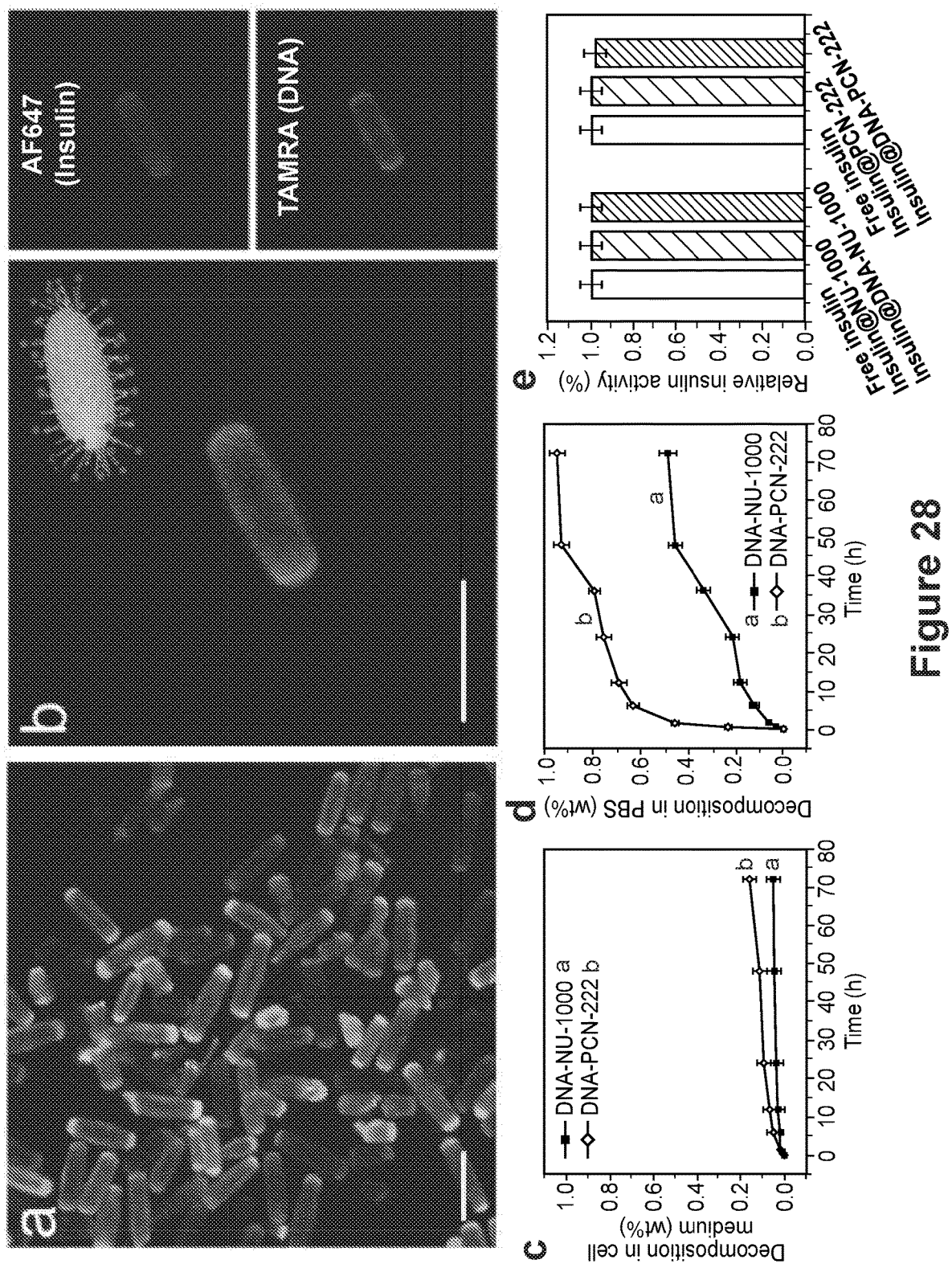
FIG. 28 shows (a) Representative confocal fluorescence micrographs of 10 μm insulin@DNA-NU-1000 particles verified the colocalization of insulin (AF647 channel) and DNA (TAMRA channel). (b) Z-stack image of a single 10 μm insulin@DNA-NU-1000 crystal. (c) Degradation profiles of DNA-NU-1000 NPs and DNA-PCN-222 NPs incubated with extracellular medium (90% DMEM medium+ 10% serum) at 37° C. with 400 rpm shaking. (d) Degradation profiles of DNA-NU-1000 NPs and DNA-PCN-222 NPs incubated in simulated intracellular medium (1×PBS, pH=7.0) at 37° C. with 400 rpm shaking. (e) Insulin activity assay as measured by ELISA for native insulin (red), insulin@MOF NPs (orange for NU-1000, pink for PCN-222), and insulin@DNA-MOF NPs (brown for NU-1000, purple for PCN-222).

In addition to colloidal stability, another desirable design consideration for intracellular protein delivery vehicles is their stability in serum/extracellular matrices and degradability inside cells to release protein cargo. Under physiological conditions, intracellular fluid exhibits significantly higher inorganic phosphate concentration (approximately 10 mM) as compared to that of serum (approximately 1 mM).[98-99] Therefore, the degradation profiles of insulin@DNA-NU-1000 and insulin@DNA-PCN-222 were evaluated by exposing them to solutions designed to emulate both extracellular and intracellular conditions (as described herein). To simulate serum fluid, MOF NPs are incubated with 90% DMEM buffer+10% blood serum (pH=7.0) at 37° C. with gentle shaking (400 rpm), where less than 5% of degradation occurred within 12 hours for both vehicles, and less than 20% within 96 hours, suggesting DNA-MOF exhibit excellent stability for circulation (FIG. 28a,b). In contrast, when MOF NPs were incubated in intracellular medium simulant (1× phosphate buffered saline, pH=7.0) at 37° C. with gentle shaking, vehicles started to degrade at much faster rates (FIG. 28c,d). Interestingly, DNA-PCN-222 exhibited much faster degradation (half-life=1 hour) as compared to that of DNA-NU-1000 (half-life=40 hours), suggesting that the deliberate choice of organic linkers could have a profound influence on the framework stability, and thus the protein release kinetics. These results are promising because DNA-MOF NPs are stable under extracellular conditions and have tunable intracellular degradation kinetics.

To directly visualize the immobilization of nucleic acids on the MOF NP surface, confocal microscopy was employed to image insulin@DNA-NU-1000 MOF NPs. Due to the resolution limit of confocal microscopy, 2.8 μm×10 μm NU-1000 particles were encapsulated with AlexaFluor 647 dye (AF647) labeled insulin, and was further functionalized with terminal TAMRA-labeled DNA, as described previously. In a representative image, the colocalization of AF647 and TAMRA signals verifies the successful encapsulation of insulin followed by functionalization of DNA (FIG. 28a). To obtain detailed information regarding relative distribution of insulin and DNA, Z-stack images of a single MOF particle were taken, where TAMRA signal (DNA) was observed to preferentially occupy the periphery while AF647 (insulin) was present throughout the particle (FIG. 28b). The observed AF647 signal at both ends of the particle increased, as compared to the center section of the MOF, indicated that proteins travel along the 1D channels, a diffusion-driven mechanism that has been studied previously.[93] Due to the large diameter of the MOF pores (3.2 nm for NU-1000 and 3.7 nm for PCN-222),[91] it is expected that the single stranded DNA penetrated through the MOF pores and functionalized the internal surface, leading to fluorescence signal inside the particles. As verified by $N_2$ adsorption isotherm, reduced $N_2$ uptake capacity was observed post-insulin encapsulation for both MOFs, and further loss of porosity was observed post-DNA functionalization (FIGS. 24 and 25). Pore size distribution analyses verified that insulin occupied both mesopores and micropores. An important question for the generality of the strategy was to determine if insulin leaked from the MOF NP pores or lost catalytic activity during the DNA functionalization process. To test this question, an enzyme-linked immunosorbent assay (ELISA) was employed to determine the encapsulation efficacy of insulin@DNA-NU-1000 and insulin@DNA-PCN-222 constructs. In both cases, no insulin activity loss was observed, suggesting the DNA functionalization does not cause protein leaching from the vehicle (FIG. 28e).

Figure 29:
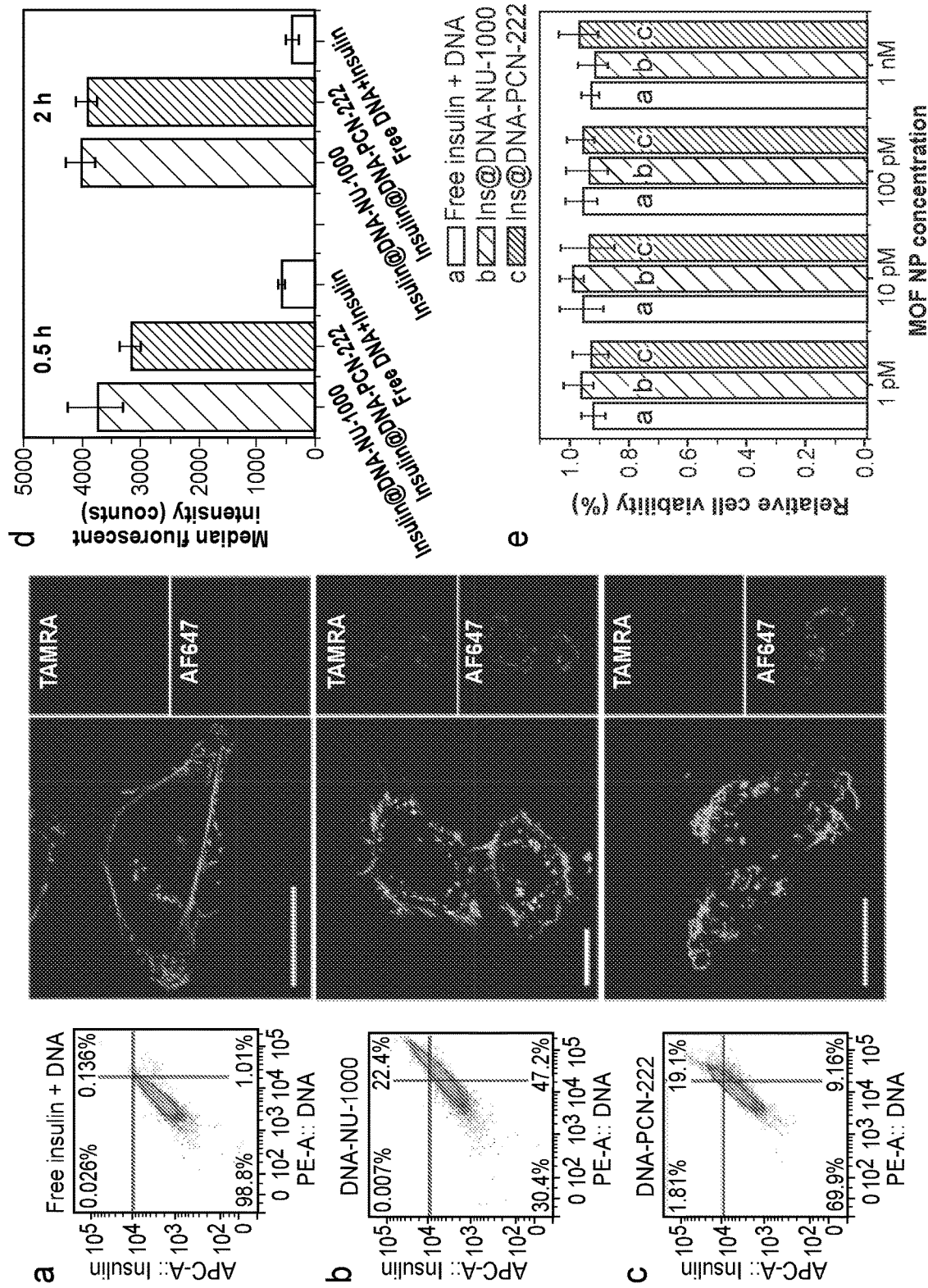
FIG. 29 shows (a-c) Flow cytometry plots and confocal fluorescence micrographs of SK-OV cells after 6 hour treatment with free insulin+DNA (a), insulin@DNA-NU-1000 (b), and insulin@DNA-PCN-222 (c). (d) Cellular uptake of insulin delivered in different constructs as determined by flow cytometry. Fluorescence at 647 nm was measured in SK-OV cells after treatment with insulin at various incubation time (0.5 hour and 2 hours). (e) MTT assay verifies no appreciable cytotoxicity induced by insulin@DNA-PCN-222 and insulin@DNA-NU-1000 NPs. Scale bar=10 μm.

As previously stated, a key characteristic of SNA-nanoparticle conjugates is their ability to effectively enter cells. Therefore, whether insulin@DNA-MOF demonstrated enhanced cellular uptake was tested. Specifically, NU-1000 and PCN-222 NPs were encapsulated with AF647 labeled insulin and functionalized with TAMRA labeled DNA and incubated with human ovarian adenocarcinoma cells, SKOV-3, for 0.5 hour, 2 hours, 6 hours, and 24 hours (as described herein). As the control group, a mixture of free TAMRA-labeled DNA and AF-647 labeled insulin was incubated with cells at the same concentration. The enrichment of insulin in cellular vesicles was demonstrated by confocal laser scanning microscopy, where strong colocalization of AF647 dye and TAMRA signals in cellular vesicles were observed (FIGS. 29a-c). The Z-stack images verified that insulin@DNA-MOF NPs were internalized by cells, as opposed to attached to the cell membrane. After 2 hours of treatment, flow cytometry was carried out and demonstrated a 10-fold increase in fluorescence in cells treated with insulin@DNA-MOF as compared to those treated with the free insulin+DNA control group (FIG. 29d). The insulin@DNA-MOF exhibits similar levels of enhancement in cellular uptake, as compared to that of conventional forms, of SNA-NP conjugates. Finally, after demonstrating DNA functionalized MOF NPs effectively enter cells without the need of transfection reagents, the in vitro cytotoxicity of both architectures evaluated by the MTT assay with negligible cytotoxicity or anti-proliferative effects observed (FIG. 29e).

In summary, a synthetic strategy to prepare protein encapsulated nucleic-MOF NP conjugates is disclosed herein, and the use of these structures to efficiently deliver proteins across cell membranes at high payload and negligible cytotoxicity has been demonstrated. It is shown herein that the surface nucleic acid functionalization significantly enhances the colloidal stability and intracellular delivery efficiency of protein encapsulated MOF NPs, all with retention of protein activity. The examples highlight the critical role of MOF surface nanostructures in enabling these highly modular materials to be useful in biological applications. It is also contemplated that the compositions and methods of the disclosure allow various proteins to be encapsulated by tuning the MOF pore sizes,[93,100-101] and also allow one to co-deliver protein and nucleic acid targets that are important for diverse purposes, such as in vivo imaging,[48] gene regulation,[78] therapeutics,[51] and studying fundamental cellular processes.[50]

REFERENCES (1) Mirkin, C. A.; Letsinger, R. L.; Mucic, R. C.; Storhoff, J. J. Nature 1996, 382, 607.
(2) Alivisatos, A. P.; Johnsson, K. P.; Peng, X. G.; Wilson, T. E.; Loweth, C. J.; Bruchez, M. P.; Schultz, P. G. Nature 1996, 382, 609.
(3) Jones, M. R.; Seeman, N. C.; Mirkin, C. A. Science 2015, 347, 1260901.
(4) Cutler, J. I.; Auyeung, E.; Mirkin, C. A. J. Am. Chem. Soc. 2012, 134, 1376.
(5) Seferos, D. S.; Giljohann, D. A.; Hill, H. D.; Prigodich, A. E.; Mirkin, C. A. J. Am. Chem. Soc. 2007, 129, 15477.
(6) Rosi, N. L.; Giljohann, D. A.; Thaxton, C. S.; Lytton-Jean, A. K. R.; Han, M. S.; Mirkin, C. A. Science 2006, 312, 1027.
(7) Park, S. Y.; Lytton-Jean, A. K. R.; Lee, B.; Weigand, S.; Schatz, G. C.; Mirkin, C. A. Nature 2008, 451, 553.
(8) Nykypanchuk, D.; Maye, M. M.; van der Lelie, D.; Gang, O. Nature 2008, 451, 549.
(9) Macfarlane, R. J.; Lee, B.; Jones, M. R.; Harris, N.; Schatz, G. C.; Mirkin, C. A. Science 2011, 334, 204.
(10) Cai, H.; Xu, Y.; Zhu, N. N.; He, P. G.; Fang, Y. Z. Analyst 2002, 127, 803.
(11) Grancharov, S. G.; Zeng, H.; Sun, S. H.; Wang, S. X.; O'Brien, S.; Murray, C. B.; Kirtley, J. R.; Held, G. A. J. Phys. Chem. B 2005, 109, 13030.
(12) Zhang, C.; Macfarlane, R. J.; Young, K. L.; Choi, C. H. J.; Hao, L. L.; Auyeung, E.; Liu, G. L.; Zhou, X. Z.; Mirkin, C. A. Nat. Mater. 2013, 12, 741.
(13) Zhang, H. T.; Zhang, J. W.; Huang, G.; Du, Z. Y.; Jiang, H. L. Chem. Commun. 2014, 50, 12069.
(14) He, C. B.; Lu, K. D.; Liu, D. M.; Lin, W. B. J. Am. Chem. Soc. 2014, 136, 5181.
(15) Morris, W.; Briley, W. E.; Auyeung, E.; Cabezas, M. D.; Mirkin, C. A. J. Am. Chem. Soc. 2014, 136, 7261.
(16) Kahn, J. S.; Freage, L.; Enkin, N.; Garcia, M. A. A.; Willner, I. Adv. Mater. 2017, 29, 1602782.
(17) Hwang, Y. K.; Hong, D. Y.; Chang, J. S.; Jhung, S. H.; Seo, Y. K.; Kim, J.; Vimont, A.; Daturi, M.; Serre, C.; Ferey, G. Angew. Chem., Int. Ed. 2008, 47, 4144.
(18) Wang, S. Z.; Morris, W.; Liu, Y. Y.; McGuirk, C. M.; Zhou, Y.; Hupp, J. T.; Farha, O. K.; Mirkin, C. A. Angew. Chem., Int. Ed. 2015, 54, 14738.
(19) Roder, R.; Preiss, T.; Hirschle, P.; Steinborn, B.; Zimpel, A.; Hohn, M.; Radler, J. O.; Bein, T.; Wagner, E.; Wuttke, S.; Lachelt, U. J. Am. Chem. Soc. 2017, 139, 2359.
(20) McGuire, C. V.; Forgan, R. S. Chem. Commun. 2015, 51, 5199.

(21) Doonan, C.; Ricco, R.; Liang, K.; Bradshaw, D.; Falcaro, P. Acc. Chem. Res. 2017, 50, 1423.
(22) Cavka, J. H.; Jakobsen, S.; Olsbye, U.; Guillou, N.; Lamberti, C.; Bordiga, S.; Lillerud, K. P. J. Am. Chem. Soc. 2008, 130, 13850.
(23) Nakayama, H.; Eguchi, T.; Nakamura, N.; Yamaguchi, S.; Danjyo, M.; Tsuhako, M. J. Mater. Chem. 1997, 7, 1063.
(24) Nonglaton, G.; Benitez, I. O.; Guisle, I.; Pipelier, M.; Leger, J.; Dubreuil, D.; Tellier, C.; Talham, D. R.; Bujoli, B. J. Am. Chem. Soc. 2004, 126, 1497.
(25) Horcajada, P.; Chalati, T.; Serre, C.; Gillet, B.; Sebrie, C.; Baati, T.; Eubank, J. F.; Heurtaux, D.; Clayette, P.; Kreuz, C.; Chang, J. S.; Hwang, Y. K.; Marsaud, V.; Bories, P. N.; Cynober, L.; Gil, S.; Ferey, G.; Couvreur, P.; Gref, R. Nat. Mater. 2010, 9, 172.
(26) He, C. B.; Liu, D. M.; Lin, W. B. Chem. Rev. 2015, 115, 11079.
(27) Shearer, G. C.; Chavan, S.; Bordiga, S.; Svelle, S.; Olsbye, U.; Lillerud, K. P. Chem. Mater. 2016, 28, 3749.
(28) Cottrell, T. L. The strengths of chemical bonds; Butterworth Scientific Publications: London, 1954; p 310.
(29) Auyeung, E.; Macfarlane, R. J.; Choi, C. H. J.; Cutler, J. I.; Mirkin, C. A. Adv. Mater. 2012, 24, 5181.
(30) Langer, R.; Tirrell, D. A. Nature 2004, 428, 487.
(31) Brodin, J. D.; Auyeung, E.; Mirkin, C. A. Proc. Natl. Acad. Sci. U.S.A. 2015, 112, 4564.
(32) Bergman, D. J.; Stockman, M. I. Phys. Rev. Lett. 2003, 90, 90.
(33) Jiang, H. L.; Feng, D. W.; Liu, T. F.; Li, J. R.; Zhou, H. C. J. Am. Chem. Soc. 2012, 134, 14690-14693.
(34) Kelty, M. L.; Morris, W.; Gallagher, A. T.; Anderson, J. S.; Brown, K. A.; Mirkin, C. A.; Harris, T. D. Chem. Commun. 2016, 52, 7854-7857.
(35) Park, J.; Jiang, Q.; Feng, D. W.; Mao, L. Q.; Zhou, H. C. J. Am. Chem. Soc. 2016, 138, 3518-3525.
(36) Jiang, D. M.; Burrows, A. D.; Edler, K. J. Crystengcomm 2011, 13, 6916-6919.
(37) Taylor-Pashow, K. M. L.; Della Rocca, J.; Xie, Z. G.; Tran, S.; Lin, W. B. J. Am. Chem. Soc. 2009, 131, 14261-+.
(38) O'Brien, M. N.; Jones, M. R.; Brown, K. A.; Mirkin, C. A. J. Am. Chem. Soc. 2014, 136, 7603-7606.
(39) Kumar, P. S.; Pastoriza-Santos, I.; Rodriguez-Gonzalez, B.; Garcia de Abajo, F. J.; LizMarzan, L. M. Nanotechnology 2008, 19.
(40) Hurst, S. J.; Lytton-Jean, A. K. R.; Mirkin, C. A. Anal. Chem. 2006, 78, 8313-8318.
(41) Zhang, C.; Macfarlane, R. J.; Young, K. L.; Choi, C. H. J.; Hao, L. L.; Auyeung, E.; Liu, G. L.; Zhou, X. Z.; Mirkin, C. A. Nat. Mater. 2013, 12, 741-746.
(42) Auyeung, E.; Macfarlane, R. J.; Choi, C. H. J.; Cutler, J. I.; Mirkin, C. A. Adv. Mater. 2012, 24, 5181-5186.
(43) Li, P.; Klet, R. C.; Moon, S. Y.; Wang, T. C.; Deria, P.; Peters, A. W.; Klahr, B. M.; Park, H. J.; Al-Juaid, S. S.; Hupp, J. T.; Farha, O. K. Chem. Commun. 2015, 51, 10925.
(44) Kelty, M. L.; Morris, W.; Gallagher, A. T.; Anderson, J. S.; Brown, K. A.; Mirkin, C. A.; Harris, T. D. Chem. Commun. 2016, 52, 7854.
(45) Chen, Y.; Li, P.; Modica, J. A.; Drout, R. J.; Farha, O. K. J Am Chem Soc 2018, 140, 5678.
(46) Wang, S. Z.; McGuirk, C. M.; Ross, M. B.; Wang, S. Y.; Chen, P. C.; Xing, H.; Liu, Y.; Mirkin, C. A. J. Am. Chem. Soc. 2017, 139, 9827.
(47) D'Astolfo, D. S.; Pagliero, R. J.; Pras, A.; Karthaus, W. R.; Clevers, H.; Prasad, V.; Lebbink, R. J.; Rehmann, H.; Geijsen, N. Cell 2015, 161, 674-690.
(48) Hoffman, R. M. Lancet Oncol. 2002, 3, 546-556.
(49) Torchilin, V. Drug Discovery Today: Technol. 2008, 5, e95-e103.
(50) Desnick, R. J.; Schuchman, E. H. Nat. Rev. Genet. 2002, 3, 954-966.
(51) Leader, B.; Baca, Q. J.; Golan, D. E. Nat. Rev. Drug Discovery 2008, 7, 21-39.
(52) Petros, R. A.; DeSimone, J. M. Nat. Rev. Drug Discovery 2010, 9, 615-627.
(53) Ghosh, P.; Yang, X. C.; Arvizo, R.; Zhu, Z. J.; Agasti, S. S.; Mo, Z. H.; Rotello, V. M. J. Am. Chem. Soc. 2010, 132, 2642-2645.
(54) Gu, Z.; Biswas, A.; Zhao, M.; Tang, Y. Chem. Soc. Rev. 2011, 40, 3638-3655.
(55) Xu, X. M.; Costa, A.; Burgess, D. J. Pharm. Res. 2012, 29, 1919-1931.
(56) Schwarze, S. R.; Ho, A.; Vocero-Akbani, A.; Dowdy, S. F. Science 1999, 285, 1569-1572.
(57) Lawrence, M. S.; Phillips, K. J.; Liu, D. R. J. Am. Chem. Soc. 2007, 129, 10110-+.
(58) Cronican, J. J.; Thompson, D. B.; Beier, K. T.; McNaughton, B. R.; Cepko, C. L.; Liu, D. R. ACS Chem. Biol. 2010, 5, 747-752.
(59) Brodin, J. D.; Sprangers, A. J.; McMillan, J. R.; Mirkin, C. A. J. Am. Chem. Soc. 2015, 137, 14838-14841.
(60) Fu, A. L.; Tang, R.; Hardie, J.; Farkas, M. E.; Rotello, V. M. Bioconjugate Chem. 2014, 25, 1602-1608.
(61) Lykourinou, V.; Chen, Y.; Wang, X. S.; Meng, L.; Hoang, T.; Ming, L. J.; Musselman, R. L.; Ma, S. Q. J. Am. Chem. Soc. 2011, 133, 10382-10385.
(62) Shih, Y. H.; Lo, S. H.; Yang, N. S.; Singco, B.; Cheng, Y. J.; Wu, C. Y.; Chang, I. H.; Huang, H. Y.; Lin, C. H. Chempluschem 2012, 77, 982-986.
(63) Liang, K.; Ricco, R.; Doherty, C. M.; Styles, M. J.; Bell, S.; Kirby, N.; Mudie, S.; Haylock, D.; Hill, A. J.; Doonan, C. J.; Falcaro, P. Nat. Commun. 2015, 6, 7240.
(64) Li, P.; Moon, S. Y.; Guelta, M. A.; Harvey, S. P.; Hupp, J. T.; Farha, O. K. J. Am. Chem. Soc. 2016, 138, 8052-8055.
(65) Doonan, C.; Riccò, R.; Liang, K.; Bradshaw, D.; Falcaro, P. Acc. Chem. Res. 2017, 50, 1423-1432.
(66) Lian, X. Z.; Fang, Y.; Joseph, E.; Wang, Q.; Li, J. L.; Banerjee, S.; Lollar, C.; Wang, X.; Zhou, H. C. Chem. Soc. Rev. 2017, 46, 3386-3401.
(67) Gkaniatsou, E.; Sicard, C.; Ricoux, R.; Mahy, J. P.; Steunou, N.; Serre, C. Mater. Horiz. 2017, 4, 55-63.
(68) Liu, W. L.; Lo, S. H.; Singco, B.; Yang, C. C.; Huang, H. Y.; Lin, C. H. J. Mater. Chem. B 2013, 1, 928-932.
(69) Cao, Y.; Wu, Z. F.; Wang, T.; Xiao, Y.; Huo, Q. S.; Liu, Y. L. Dalton Trans. 2016, 45, 6998-7003.
(70) Lian, X. Z.; Erazo-Oliveras, A.; Pellois, J. P.; Zhou, H. C. Nat. Commun. 2017, 8.
(71) Sindoro, M.; Yanai, N.; Jee, A. Y.; Granick, S. Acc. Chem. Res. 2014, 47, 459-469.
(72) Morris, W.; Wang, S. Z.; Cho, D.; Auyeung, E.; Li, P.; Farha, O. K.; Mirkin, C. A. ACS Appl. Mater. Interfaces 2017.
(73) Frohlich, E. Int. J. Nanomed. 2012, 7, 5577-5591.
(74) Baati, T.; Njim, L.; Neffati, F.; Kerkeni, A.; Bouttemi, M.; Gref, R.; Najjar, M. F.; Zakhama, A.; Couvreur, P.; Serre, C.; Horcajada, P. Chem. Sci. 2013, 4, 1597-1607.
(75) He, C. B.; Liu, D. M.; Lin, W. B. Chem. Rev. 2015, 115, 11079-11108.

(76) Ruyra, A.; Yazdi, A.; Espin, J.; Carne-Sanchez, A.; Roher, N.; Lorenzo, J.; Imaz, I.; Maspoch, D. Chem.—Eur. J. 2015, 21, 2508-2518.
(77) Morris, W.; Briley, W. E.; Auyeung, E.; Cabezas, M. D.; Mirkin, C. A. J. Am. Chem. Soc. 2014, 136, 7261-7264.
(78) He, C. B.; Lu, K. D.; Liu, D. M.; Lin, W. B. J. Am. Chem. Soc. 2014, 136, 5181-5184.
(79) Mirkin, C. A.; Letsinger, R. L.; Mucic, R. C.; Storhoff, J. J. Nature 1996, 382, 607-609.
(80) Cutler, J. I.; Auyeung, E.; Mirkin, C. A. J. Am. Chem. Soc. 2012, 134, 1376-1391.
(81) Patel, P. C.; Giljohann, D. A.; Daniel, W. L.; Zheng, D.; Prigodich, A. E.; Mirkin, C. A.
Bioconjugate Chem. 2010, 21, 2250-2256.
(82) Choi, C. H. J.; Hao, L. L.; Narayan, S. P.; Auyeung, E.; Mirkin, C. A. Proc. Natl. Acad. Sci.
U.S.A 2013, 110, 7625-7630.
(83) Young, K. L.; Scott, A. W.; Hao, L. L.; Mirkin, S. E.; Liu, G. L.; Mirkin, C. A. Nano Lett. 2012, 12, 3867-3871.
(84) Banga, R. J.; Chernyak, N.; Narayan, S. P.; Nguyen, S. T.; Mirkin, C. A. J. Am. Chem. Soc. 2014, 136, 9866-9869.
(85) Calabrese, C. M.; Merkel, T. J.; Briley, W. E.; Randeria, P. S.; Narayan, S. P.; Rouge, J. L.; Walker, D. A.; Scott, A. W.; Mirkin, C. A. Angew. Chem., Int. Ed. 2015, 54, 476-480.
(86) Rosi, N. L.; Mirkin, C. A. Chem. Rev. 2005, 105, 1547-1562.
(87) Rosi, N. L.; Giljohann, D. A.; Thaxton, C. S.; Lytton-Jean, A. K. R.; Han, M. S.; Mirkin, C. A. Science 2006, 312, 1027-1030.
(88) Radovic-Moreno, A. F.; Chernyak, N.; Mader, C. C.; Nallagatla, S.; Kang, R. S.; Hao, L. L.; Walker, D. A.; Halo, T. L.; Merkel, T. J.; Rische, C. H.; Anantatmula, S.; Burkhart, M.; Mirkin, C. A.; Gryaznov, S. M. Proc. Natl. Acad. Sci. U.S.A 2015, 112, 3892-3897.
(89) Mondloch, J. E.; Bury, W.; Fairen-Jimenez, D.; Kwon, S.; DeMarco, E. J.; Weston, M. H.; Sarjeant, A. A.; Nguyen, S. T.; Stair, P. C.; Snurr, R. Q.; Farha, O. K.; Hupp, J. T. J. Am. Chem. Soc. 2013, 135, 10294-10297.
(90) Morris, W.; Volosskiy, B.; Demir, S.; Gandara, F.; McGrier, P. L.; Furukawa, H.; Cascio, D.; Stoddart, J. F.; Yaghi, O. M. Inorg. Chem. 2012, 51, 6443-6445.
(91) Feng, D. W.; Gu, Z. Y.; Li, J. R.; Jiang, H. L.; Wei, Z. W.; Zhou, H. C. Angew. Chem., Int. Ed. 2012, 51, 10307-10310.
(92) Chen, Y.; Li, P.; Modica, J. A.; Drout, R. J.; Farha, O. K. J. Am. Chem. Soc. 2018, 140, 5678-5681.
(93) Li, P.; Modica, J. A.; Howarth, A. J.; Vargas, E. L.; Moghadam, P. Z.; Snurr, R. Q.; Mrksich, M.; Hupp, J. T.; Farha, O. K. Chem 2016, 1, 154-169.
(94) Li, P.; Klet, R. C.; Moon, S. Y.; Wang, T. C.; Deria, P.; Peters, A. W.; Klahr, B. M.; Park, H. J.; Al-Juaid, S. S.; Hupp, J. T.; Farha, O. K. Chem. Commun. 2015, 51, 10925-10928.
(95) Kelty, M. L.; Morris, W.; Gallagher, A. T.; Anderson, J. S.; Brown, K. A.; Mirkin, C. A.; Harris, T. D. Chem. Commun. 2016, 52, 7854-7857.
(96) Wang, S. Z.; McGuirk, C. M.; Ross, M. B.; Wang, S. Y.; Chen, P. C.; Xing, H.; Liu, Y.; Mirkin, C. A. J. Am. Chem. Soc. 2017, 139, 9827-9830.
(97) Narayan, S. P.; Choi, C. H. J.; Hao, L. L.; Calabrese, C. M.; Auyeung, E.; Zhang, C.; Goor, O. J. G. M.; Mirkin, C. A. Small 2015, 11, 4173-4182.
(98) Libanati, C. M.; Tandler, C. J. J. Cell Biol. 1969, 42, 754-765.
(99) Bansal, V. K., Serum Inorganic Phosphorus. In Clinical Methods: The History, Physical, and Laboratory Examinations, rd; Walker, H. K.; Hall, W. D.; Hurst, J. W., Eds. Boston, 1990.
(100) Feng, D. W.; Liu, T. F.; Su, J.; Bosch, M.; Wei, Z. W.; Wan, W.; Yuan, D. Q.; Chen, Y. P.; Wang, X.; Wang, K. C.; Lian, X. Z.; Gu, Z. Y.; Park, J.; Zou, X. D.; Zhou, H. C. Nat. Commun. 2015, 6.
(101) Li, P.; Chen, Q.; Wang, T. C.; Vermeulen, N. A.; Mehdi, B. L.; Dohnalkova, A.; Browning, N. D.; Shen, D.; Anderson, R.; Gomez-Gualdron, D. A.; Cetin, F. M.; Jagiello, J.; Asiri, A. M.; Stoddart, J. F.; Farha, O. K. Chem 2018, 4, 1022-1034.

What is claimed is:

1. An oligonucleotide-functionalized metal-organic framework (MOF) nanoparticle, wherein the oligonucleotide is a terminal phosphate-modified oligonucleotide and the phosphate forms a metal-phosphate bond with the metal ion of the MOF nanoparticle, wherein the terminal phosphate-modified oligonucleotide comprises a (GGT)$_n$ nucleotide sequence, wherein n is 2-20.

2. The nanoparticle of claim 1, wherein the MOF nanoparticle comprises zirconium (Zr), chromium (Cr), iron (Fe), and/or aluminum (Al).

3. The nanoparticle of claim 1, wherein the terminal phosphate-modified oligonucleotide has a phosphate group on its 3' end.

4. The nanoparticle of claim 1, wherein the terminal phosphate-modified oligonucleotide has a phosphate group on its 5' end.

5. The nanoparticle of claim 1, further comprising an agent selected from the group consisting of a peptide, a protein, a nanoparticle, an antibody, a small molecule, and a combination thereof, wherein the agent is encapsulated in the nanoparticle.

6. The nanoparticle of claim 1, wherein the MOF nanoparticle comprises a plurality of terminal phosphate-modified oligonucleotides on its surface and at least one oligonucleotide regulates gene expression.

7. A method of making an oligonucleotide-functionalized metal-organic framework (MOF) nanoparticle, comprising:
  (a) mixing a metal ion and a multi-dentate ligand to form the MOF nanoparticle; and
  (b) contacting the MOF nanoparticle with a plurality of terminal phosphate-modified oligonucleotides, wherein one or more of the plurality of terminal phosphate-modified oligonucleotides comprises a (GGT)$_n$ nucleotide sequence, wherein n is 2-20, thereby producing the oligonucleotide-functionalized MOF nanoparticle, such that the phosphate groups of the terminal phosphate-modified oligonucleotides associate with coordinatively unsaturated metal sites (CUS) on the MOF nanoparticle surface via a metal-phosphate bond.

8. The method of claim 7, wherein the multi-dentate ligand comprises 2, 3, or 4 coordinating functional groups.

9. The method of claim 7, wherein the multi-dentate ligand is a bi-dentate ligand.

10. The method of claim 7, wherein the multi-dentate ligand is a tri-dentate ligand.

11. The method of claim 7, wherein the metal ion comprises a 12-connect Zr$_3$ cluster, a 6-connect Zr$_3$ cluster, a 8-connect Zr$_3$ cluster, a Cr$_3$ cluster, a Fe$_3$ cluster, a Al$_3$ cluster, or a combination thereof.

12. The method of claim 7, further comprising step (d): adding a salt solution to the oligonucleotide-functionalized MOF nanoparticle, wherein step (d) is after step (c).

13. The method of claim 12, wherein the salt solution is added to a final concentration of 0.5 M.

14. The method of claim 12, further comprising step (e): contacting the oligonucleotide-functionalized MOF nanoparticle with one or more nanoparticles, wherein each of the one or more nanoparticles comprises an oligonucleotide that is sufficiently complementary to hybridize to the oligonucleotide on the surface of the oligonucleotide-functionalized MOF nanoparticle, and wherein step (e) is after step (d).

15. A method of inhibiting expression of a gene product comprising hybridizing a target polynucleotide encoding the gene with one or more oligonucleotides complementary to all or a portion of the target polynucleotide, the oligonucleotide being the terminal phosphate-modified oligonucleotide of the nanoparticle of claim 1, wherein hybridizing between the target polynucleotide and the terminal phosphate-modified oligonucleotide occurs over a length of the target polynucleotide with a degree of complementarity sufficient to inhibit expression of the gene product.

16. A method for up-regulating activity of a toll-like receptor (TLR) comprising contacting a cell having the TLR with the nanoparticle of claim 1.

17. The method of claim 16 wherein the terminal phosphate-modified oligonucleotide comprises a TLR agonist.

18. The nanoparticle of claim 2, wherein the MOF nanoparticle comprises UiO-66, UiO-67-bpy, UiO68-N3/PCN-58, PCN-222/MOF-545, PCN-223, PCN-224, MIL-101 (Al), MIL-101 (Fe), or MIL-101(Cr).

19. The nanoparticle of claim 1, wherein the MOF nanoparticle comprises a plurality of terminal phosphate-modified oligonucleotides and density of the plurality of terminal phosphate-modified oligonucleotides on the surface of the MOF nanoparticle is from about 2 pmol/cm$^2$ to about 24 pmol/cm$^2$.

20. The nanoparticle of claim 6, wherein the at least one terminal phosphate-modified oligonucleotide is an antisense oligonucleotide.

21. The nanoparticle of claim 1, wherein the terminal phosphate-modified oligonucleotide is RNA.

22. The nanoparticle of claim 21, wherein the RNA is small interfering RNA (siRNA).

23. The method of claim 7, wherein the multi-dentate ligand comprises at least one carboxylate functional group.

24. The method of claim 7, wherein the multi-dentate ligand comprises at least one heterocyclic group having at least one ring nitrogen.

25. The method of claim 7, wherein the multi-dentate ligand comprises formic acid, acetic acid, oxalic acid, propanoic acid, butanedioic acid, (E)-butenedioic acid, benzene-1, 4-dicarboxylic acid, benzene-1,3-dicarboxylic acid, benzene-1,3,5-tricarboxylic acid, 2-amino-1,4-benzenedicarboxylic acid, 2-bromo-1,4-benzenedicarboxylic acid, biphenyl-4,4'-dicarboxylic acid, biphenyl-3,3',5,5'-tetracarboxylic acid, biphenyl-3,4',5-tricarboxylic acid, 2,5-dihydroxy-1,4-benzenedicarboxylic acid, 1,3,5-tris(4-carboxyphenyl)benzene, (2E,4E)-hexa-2,4-dienedioic acid, 1,4-naphthalenedicarboxylic acid, pyrene-2,7-dicarboxylic acid, 4,5,9,10-tetrahydropyrene-2,7-dicarboxylic acid, aspartic acid, glutamic acid, adenine, 4,4'-bypiridine, pyrimidine, pyrazine, pyridine-4-carboxylic acid, pyridine-3-carboxylic acid, imidazole, 1 H-benzimidazole, 2-methyl-1 H-imidazole, or a mixture thereof.

26. The method of claim 7, wherein the multi-dentate ligand comprises terephthalic acid (H2BDC), 2,2'-bipyridine-5,5'-dicarboxylic acid (H2BPY), 2',5'-bis(azidomethyl)-[1,1':4',1"-terphenyl]-4,4"-dicarboxylic acid, (H2TPDC-N3), 4,4',4",4'''-porphyrin tetrabenzoic acid (H2TCPP), or a combination thereof.

27. The method of claim 7, wherein the MOF nanoparticle further comprises an agent selected from the group consisting of a peptide, a protein, a nanoparticle, an antibody, a small molecule, and a combination thereof, wherein the agent is encapsulated in the nanoparticle.

28. The method of claim 27, further comprising the step, prior to step (b), of contacting the MOF nanoparticle with the agent thereby encapsulating the agent in the nanoparticle.

29. The method of claim 15 wherein expression of the gene product is inhibited in vivo.

30. The method of claim 15 wherein expression of the gene product is inhibited in vitro.

31. The method of claim 16 wherein the TLR is chosen from the group consisting of toll-like receptor 1 (TLR1), toll-like receptor 2 (TLR2), toll-like receptor 3 (TLR3), toll-like receptor 4 (TLR4), toll-like receptor 5 (TLR5), toll-like receptor 6 (TLR6), toll-like receptor 7 (TLR7), toll-like receptor 8 (TLR8), toll-like receptor 9 (TLR9), toll-like receptor 10 (TLR10), toll-like receptor 11 (TLR11), toll-like receptor 12 (TLR12), and toll-like receptor 13 (TLR13).

32. The method of claim 16 which is performed in vitro.

33. The method of claim 16 which is performed in vivo.

34. The method of claim 7, wherein the MOF nanoparticle comprises zirconium (Zr), chromium (Cr), iron (Fe), and/or aluminum (Al).

* * * * *